US005527677A

United States Patent [19]
Deguchi et al.

[11] Patent Number: 5,527,677
[45] Date of Patent: Jun. 18, 1996

[54] METHODS AND KITS FOR IDENTIFYING HUMAN ARYLAMINE N-ACETYLTRANSFERASE GENES

[75] Inventors: Takeo Deguchi, Hachiouji; Moritoshi Kinoshita, Itano-gun; Kiyonori Katsuragi, Tokushima; Sadahito Shin, Itano-gun, all of Japan

[73] Assignees: Tokyo Metropolitan Institute for Neuroscience; Otsuka Pharmaceutical Co., Ltd., both of Tokyo, Japan

[21] Appl. No.: 321,478

[22] Filed: Oct. 11, 1994

Related U.S. Application Data

[63] Continuation of Ser. No. 38,667, Mar. 23, 1993, abandoned.

[30] Foreign Application Priority Data

Mar. 23, 1992 [JP] Japan .................................. 4-064669

[51] Int. Cl.$^6$ ............................ C12Q 1/68; C12P 19/34; C07H 21/04
[52] U.S. Cl. ...................... 435/6; 435/91.2; 536/24.31; 536/24.33
[58] Field of Search .................... 435/6, 91.2; 536/23.2, 536/23.5, 24.1, 24.3, 24.31, 24.33; 935/78

[56] References Cited

U.S. PATENT DOCUMENTS 4,683,202  7/1987  Mullis .................................... 435/91.2

FOREIGN PATENT DOCUMENTS 0463395  1/1992  European Pat. Off. .

OTHER PUBLICATIONS

Deguchi et al., *J. Biol. Chem.* 265(22), 12757–12760 (1990).
Grant et al., *Nucleic Acids Res.* 17(10), 3978 (1989).
Blum et al., *DNA and Cell Biol.* 9(3), 193–203 (1990).
Blum et al., *Proc. Natl. Acad. Sci. USA* 88, 5237–5241 (1991).
The Journal of Biological Chemistry, vol. 263, No. 16, pp. 7534–7538, "Arylamine N-Acetyltransferase from Chicken Liver", (1988) Ohsako et al. (1988).
The Journal of Biological Chemistry, vol. 265, No. 8, pp. 4630–4634, "Cloning and Expression of cDNAs for Polymorphic and Monomorphic Arylamine N-Acetyltransferases from Human Liver", (1990) Ohsako et al. (1990).
Biochemical and Biophysical Research Communications, vol. 177, No. 3, pp. 1252–1257, "Structure and Restriction Fragment Length Polymorphism of Genes for Human Liver Arylamine N-Acetyltransferases", (1991) Ebisawa et al.

*Primary Examiner*—W. Gary Jones
*Assistant Examiner*—Kenneth R. Horlick
*Attorney, Agent, or Firm*—Sughrue, Mion, Zinn, Macpeak & Seas

[57] ABSTRACT

The invention provides polymorphic human arylamine N-acetyltransferase (NAT) genes, more precisely a type 1 NAT gene containing the 5'-noncoding region base sequence of SEQ ID NO:1 and the coding region-containing base sequence of SEQ ID NO:2, a type 2 NAT gene containing the sequences of SEQ ID NO:3 and SEQ ID NO:4 and a type 3 NAT gene containing the sequences of SEQ ID NO:5 and SEQ ID NO:6, as well as a method of detecting these polymorphic genes and a method of diagnosing an adverse effect or effects to be caused by an amino-containing aromatic substance.

5 Claims, 18 Drawing Sheets

FIG. 10A

Site O1

| | 1 | 2 | 3 | 4 | 5 | 6 | 7 | 8 | 9 | 10 | 11 | 12 | 13 |
|---|---|---|---|---|---|---|---|---|---|---|---|---|---|
| 501, 489 | — | | | | | | | | | | | | |
| 404 | — | | | | | | | | | | | | |
| 331 | — | | | | | | | | | | | | |
| 242 | — | | | | | | | | | | | | |
| 190 | — | | | | | | | | | | | | |
| 147 | — | — | — | — | — | — | — | — | — | — | — | — | — |
| 111, 110 | | | | | | | | | | | | | |
| 67 | — | = | = | = | = | = | = | = | = | = | = | = | = |
| 34 | — | | | | | | | | | | | | |

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
  ( A ) LENGTH: 2768 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: exon
  ( B ) LOCATION: 2220..2320

( x i ) SEQUENCE DESCRIPTION: SEQ ID NO:1:

```
GGATCCTTGA   CTCTGGTCTT   ACTCTCCCTT   AGTCACAAGT   CTCCTCATCT   CATAGTTTCC        60
```

| | | | | | |
|---|---|---|---|---|---|
| CATGACGGTT | CTTGCTGGAC | ATCCTCAAGG | ATCTCTGTCA | AACTGACAAT | AATTAGAGGC | 120 |
| AATCTCAGAA | TTACGCATGT | GCCAATCTGG | ATTGCAACAT | TTTAATTCCA | GGTGTCAGGT | 180 |
| TTCCAACAAT | CAAGGAGAAA | AATGACCATA | ATCCATTGAC | AATTCCTCTC | CCACACTCAG | 240 |
| TCAAAAATGG | TCCAGATCAC | AGTCCTACAT | GCTGGAATTA | TTTCCTCTGC | TTCTCTCTCA | 300 |
| CCCCACCTTG | GCCAAAGATT | TTCTAGCAAG | ATCTGAATTT | TAATCCATCT | CTCTTCGCCT | 360 |
| GTGTGTCCCG | ACTAATTTGG | CAGAAGGAAT | TCTTTCTTAA | ACCTTGCCAT | TTAATTCACA | 420 |
| AATGGAAATG | TGAAGGGTCA | ATAGGTATGT | GAAGAACCTA | TTCACCCGTA | TTCACTGGGA | 480 |
| ATCAGAGAAG | TGAAAATGGA | AAAGAACACT | GAGCTATCAT | CTTAGATACA | CAAAACTGTC | 540 |
| AAACATTTGA | AGGTGGCTAA | CACCAAATGT | CAATCAGGAT | ATGAGGAAAG | TAGGAATTCT | 600 |
| TCTATACAAG | AGGACAGAAA | TCTGGCAGTG | CCAAAAGAAA | AACTACATCT | ATGATCTGCC | 660 |
| CCTCCGCAGA | TCCCATTCCT | AATACATATA | TCCCAGCGAG | TTCTGCTAAT | CTGCAGAGGA | 720 |
| TGTCTAGAAA | CGCATTCATC | ACATCAGTGT | TTATAATAAC | CAGGAGTAGG | AGGCAATCAA | 780 |
| ATGTCCTTCA | CAAGTGGAAC | TGGTAAGTTA | AAGAGACTTA | GGTTGGGTTT | CTCTAAAACC | 840 |
| AGGCCACAAG | ACAAAGATTT | GTATTCCAGT | GGCTTATTTT | GATTTAGGAG | ATGATTTAAG | 900 |
| GAATCACCAG | TGCGGGAGGT | ATAACAGTGA | ACCCAAGACA | CCTTGAGATC | AATAAAAGG | 960 |
| TGCATTGTTG | GCAGGCTGCC | TGCAAAGAAG | GGAGCATATC | CAGTAGACAC | ACCAGGAGGC | 1020 |
| AGTTTGTACA | TGCCTAAGAG | TAATCCCACC | TTAGCTGTAG | AACACAAGGA | TATTCAGTCT | 1080 |
| CCAGTTCCCA | TCATGTGGGC | TGAGTGGTGG | TCCCAGGTGC | TTTAATTTGT | AGTCCATCTG | 1140 |
| CCCAAGCACA | GGCCAAAAGA | AAGCCTTCCC | ACAGAGTCCC | GAGTTCATGT | GGCAGCATGC | 1200 |
| CAGAGGTATG | TACTGGAACA | GTAGGTGCGA | AAGGCAACAA | TTACATCATG | AAAACTGCAC | 1260 |
| ATCTCACTCA | TATGTGGAAT | CTAAAGTAAT | TTAGCTCATA | GAAGTTAAGA | GTAGAATAGT | 1320 |
| TAGAGTAGTA | GAAAGTTAAG | AGTTGTTACT | GGAGAGAAAA | GAGGGTATGA | AGCTAGGAAA | 1380 |
| AAAGCTAGAA | GGAAGGATTT | TGAATGTTCT | CATGACAAAG | AGATGATAAA | TGTTTGAGGT | 1440 |
| GACAGACATG | CTAATTACCA | TGATTTGATC | TTTACACAAT | GTCTGCATGT | ATCAGAACAT | 1500 |
| CACACACTAC | CAAATAAATA | TATACAATTG | TTATGTGTCA | AAAAACATTA | TATACAATGT | 1560 |
| TTATATTTTA | TATTAATATT | AATGTAAATA | AAAATTTACA | CAAATCTTTT | CATTAAATAT | 1620 |
| GGTGTGGATA | ATTATATTAT | CTGATGATAC | CCATGCCACA | GGCTAGGAGA | AATAAAAATT | 1680 |
| TACATTAATG | TTAATGTCAA | AAAAGCAGAA | ACAAAGCCAT | ATGATACATG | TGACACTTAT | 1740 |
| ACCACATGCA | TAGAGTTATT | TCAGACACAT | TGTGTGTTAC | CTTTGGGTAG | AGAAGTGAAT | 1800 |
| GAGAGTGAGG | ATGAGAGATG | AAAAGAGGCA | GAAGAAAAAA | GAGAGGCCTT | ATAGGAAGTG | 1860 |
| ATGAAAGTGT | GCCATAAACT | GAGAGTATGA | CTAAAACCTT | TCATCTTCCT | CTTCTGCCGC | 1920 |
| TTCTAAGTTA | TTGGTTCTGC | TGTTCCTTGA | CCTGTTTCAA | GCTCTCACCT | TCTATATCAC | 1980 |
| ACATGGGAAG | TCTGGCATCA | GACTTCCAGA | GAGCAAGAAC | TAGGTGAAAT | ACAAGGGCAC | 2040 |
| AGCTCTCCTA | GCCTGTGGCA | TGGGTATCAT | CAGATAATAT | AATTATCCAC | ACCATTTTA | 2100 |
| ACGAAAAGAT | TTGCGTAAGA | GATTCGCAGA | GGCAACCTGA | GGCCCTGCAA | CTACATTTCC | 2160 |
| CAGAGATCCC | TGAGGTGATC | CTAACTAGAC | TCTGGTGTCA | GGGTGATACG | GAATTCCAGT | 2220 |
| GAGATCACTT | CCCTTGCAGA | CTTTGGAAGG | GAGAGCACTT | TATTACAGAC | CTTGGAAGCA | 2280 |
| AGAGGATTGC | ATTCAGCCTA | GTTCCTGGTT | GCTGGCCAAA | GTAAGTAGAA | CTTTGTAAGT | 2340 |
| AATTTGCAGT | GTACTTTGAA | AGTGGGGTAT | AAATTAAAAA | TAAAATCAAG | TCCCCCTACT | 2400 |
| GACTGAATGG | ATCCCCTCTT | GTCCTAGGCG | ACCCCAGAGA | AACCTGGAAA | ACTAAATTCC | 2460 |

| | | | | | |
|---|---|---|---|---|---|
| AGGCCATAAT | GGAAAGGGAG | GTCAGACACG | CCTCATTATA | CACACTCCCT | TTTGGAGTTC | 2520 |
| AGGCACAACT | GACCAGCATT | AACATTGAAA | CAGTGATCAT | AAGACTGTCA | AAATGGACTG | 2580 |
| TTTGTGGGAA | TAAGATACCA | AATTCCAATC | TGACTCTGGT | TTAGCATCAC | ATGACAATAG | 2640 |
| CAGACCCTGA | AGGAAATCAA | TATATTTAAT | CCCAAAATAT | ATTTCTTTGA | CACATATTGA | 2700 |
| ATGGTCTTGC | AAACCATCTT | TATGGGAATT | TGCTGGTTTC | TGGCTCTGCT | CTGATTGAGG | 2760 |
| AGAGATAA | | | | | | 2768 |

( 2 ) INFORMATION FOR SEQ ID NO:2:

( i ) SEQUENCE CHARACTERISTICS:
        ( A ) LENGTH: 6464 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 723..1595

( i x ) FEATURE:
        ( A ) NAME/KEY: exon
        ( B ) LOCATION: 717..1936

( i x ) FEATURE:
        ( A ) NAME/KEY: polyA_signal
        ( B ) LOCATION: 1794..1799

( i x ) FEATURE:
        ( A ) NAME/KEY: polyA_signal
        ( B ) LOCATION: 1800..1805

( x i ) SEQUENCE DESCRIPTION: SEQ ID NO:2:

| | | | | | |
|---|---|---|---|---|---|
| GAATTCAGTG | TCTCTCCCTG | TGCACCCACT | AACCCTCTT | TTTGTTTTCA | CCAGGCACTT | 60 |
| ACCACAATCT | AACAGACTGC | ATGTTTTATC | CATTTATTCA | GTTTCCTATT | TGTGTCCCTT | 120 |
| CAACTCCCAT | TAAAATATAA | TATTTTTGAG | GGCAAGCAAG | TACTAGAACA | ATAGGAAACA | 180 |
| CATCAAGAGT | ATTCTGTAAA | CTATTTCTTG | AATCAATCAG | TGAATGAATG | AATTAATCAA | 240 |
| TATATTTTTT | GAGTGAGGAG | CTTTGTGTTA | GGTACAGCTA | AATGGGAAAT | CAAGTGGGTC | 300 |
| ATGTACCATG | AATACCATAT | ACTCTACTGT | ATAATTCTCC | TGCTTATATC | AGAAACTGTT | 360 |
| TATAAGCCTA | TTATAATTGA | TACCAATTGG | AATCTCTTTT | TTACTCATCA | CCAAGAACAC | 420 |
| CACAAACAAG | TTGTTTACCA | TTTGGCTCCT | TATTTAATCT | GGATTTCCAA | CTCCTCATGC | 480 |
| TTAAAAGACG | GAAGATACAA | TAATACTTTC | CTTACAGGGT | TCTGAGACTA | CTAAGAGAAC | 540 |
| TTATGCATGT | AAAAGGGATT | CATGCAGTAG | AAATACTAAC | AAAAGAATTA | CTATGACAGA | 600 |
| TACTTATAAC | CATTGTGTTT | TTACGTATTT | AAAATACGTT | ATACCTATAA | TTAGTCACAC | 660 |
| GAGGAAATCA | AATGCTAAAG | TATGATATGT | TTTTATGTTT | TGTTTTCTT | GCTTAGGGGA | 720 |

| | | | | | | | | | | | | | | | | |
|---|---|---|---|---|---|---|---|---|---|---|---|---|---|---|---|---|
| TC | ATG | GAC | ATT | GAA | GCA | TAT | TTT | GAA | AGA | ATT | GGC | TAT | AAG | AAC | TCT | 767 |
| | Met | Asp | Ile | Glu | Ala | Tyr | Phe | Glu | Arg | Ile | Gly | Tyr | Lys | Asn | Ser | |
| | 1 | | | 5 | | | | | 10 | | | | | 15 | | |
| AGG | AAC | AAA | TTG | GAC | TTG | GAA | ACA | TTA | ACT | GAC | ATT | CTT | GAG | CAC | CAG | 815 |
| Arg | Asn | Lys | Leu | Asp | Leu | Glu | Thr | Leu | Thr | Asp | Ile | Leu | Glu | His | Gln | |
| | | 20 | | | | 25 | | | | | 30 | | | | | |
| ATC | CGG | GCT | GTT | CCC | TTT | GAG | AAC | CTT | AAC | ATG | CAT | TGT | GGG | CAA | GCC | 863 |
| Ile | Arg | Ala | Val | Pro | Phe | Glu | Asn | Leu | Asn | Met | His | Cys | Gly | Gln | Ala | |
| | 35 | | | | 40 | | | | | 45 | | | | | | |
| ATG | GAG | TTG | GGC | TTA | GAG | GCT | ATT | TTT | GAT | CAC | ATT | GTA | AGA | AGA | AAC | 911 |
| Met | Glu | Leu | Gly | Leu | Glu | Ala | Ile | Phe | Asp | His | Ile | Val | Arg | Arg | Asn | |

```
        50                             55                             60
CGG GGT GGG TGG TGT CTC CAG GTC AAT CAA CTT CTG TAC TGG GCT CTG         959
Arg Gly Gly Trp Cys Leu Gln Val Asn Gln Leu Leu Tyr Trp Ala Leu
         65                      70                      75

ACC ACA ATC GGT TTT CAG ACC ACA ATG TTA GGA GGG TAT TTT TAC ATC        1007
Thr Thr Ile Gly Phe Gln Thr Thr Met Leu Gly Gly Tyr Phe Tyr Ile
 80                      85                      90                      95

CCT CCA GTT AAC AAA TAC AGC ACT GGC ATG GTT CAC CTT CTC CTG CAG        1055
Pro Pro Val Asn Lys Tyr Ser Thr Gly Met Val His Leu Leu Leu Gln
                    100                     105                     110

GTG ACC ATT GAC GGC AGG AAT TAC ATT GTC GAT GCT GGG TCT GGA AGC        1103
Val Thr Ile Asp Gly Arg Asn Tyr Ile Val Asp Ala Gly Ser Gly Ser
                115                     120                     125

TCC TCC CAG ATG TGG CAG CCT CTA GAA TTA ATT TCT GGG AAG GAT CAG        1151
Ser Ser Gln Met Trp Gln Pro Leu Glu Leu Ile Ser Gly Lys Asp Gln
            130                     135                     140

CCT CAG GTG CCT TGC ATT TTC TGC TTG ACA GAA GAG AGA GGA ATC TGG        1199
Pro Gln Val Pro Cys Ile Phe Cys Leu Thr Glu Glu Arg Gly Ile Trp
        145                     150                     155

TAC CTG GAC CAA ATC AGG AGA GAG CAG TAT ATT ACA AAC AAA GAA TTT        1247
Tyr Leu Asp Gln Ile Arg Arg Glu Gln Tyr Ile Thr Asn Lys Glu Phe
160                     165                     170                     175

CTT AAT TCT CAT CTC CTG CCA AAG AAG AAA CAC CAA AAA ATA TAC TTA        1295
Leu Asn Ser His Leu Leu Pro Lys Lys Lys His Gln Lys Ile Tyr Leu
                    180                     185                     190

TTT ACG CTT GAA CCT CGA ACA ATT GAA GAT TTT GAG TCT ATG AAT ACA        1343
Phe Thr Leu Glu Pro Arg Thr Ile Glu Asp Phe Glu Ser Met Asn Thr
                195                     200                     205

TAC CTG CAG ACG TCT CCA ACA TCT TCA TTT ATA ACC ACA TCA TTT TGT        1391
Tyr Leu Gln Thr Ser Pro Thr Ser Ser Phe Ile Thr Thr Ser Phe Cys
            210                     215                     220

TCC TTG CAG ACC CCA GAA GGG GTT TAC TGT TTG GTG GGC TTC ATC CTC        1439
Ser Leu Gln Thr Pro Glu Gly Val Tyr Cys Leu Val Gly Phe Ile Leu
        225                     230                     235

ACC TAT AGA AAA TTC AAT TAT AAA GAC AAT ACA GAT CTG GTC GAG TTT        1487
Thr Tyr Arg Lys Phe Asn Tyr Lys Asp Asn Thr Asp Leu Val Glu Phe
240                     245                     250                     255

AAA ACT CTC ACT GAG GAA GAG GTT GAA GAA GTG CTG AAA AAT ATA TTT        1535
Lys Thr Leu Thr Glu Glu Glu Val Glu Glu Val Leu Lys Asn Ile Phe
                    260                     265                     270

AAG ATT TCC TTG GGG AGA AAT CTC GTG CCC AAA CCT GGT GAT GGA TCC        1583
Lys Ile Ser Leu Gly Arg Asn Leu Val Pro Lys Pro Gly Asp Gly Ser
                275                     280                     285

CTT ACT ATT TAGAATAAGG AACAAAATAA ACCCTTGTGT ATGTATCACC                 1632
Leu Thr Ile
        290

CAACTCACTA ATTATCAACT TATGTGCTAT CAGATATCCT CTCTACCCTC ACGTTATTTT       1692

GAAGAAAATC CTAAACATCA AATACTTTCA TCCATAAAAA TGTCAGCATT TATTAAAAAA       1752

CAATAACTTT TTAAAGAAAC ATAAGGACAC ATTTTCAAAT TAATAAAAAT AAAGGCATTT       1812

TAAGGATGGC CTGTGATTAT CTTGGGAAGC AGAGTGATTC ATGCTAGAAA ACATTTAATA       1872

TTGATTTATT GTTGAATTCA TAGTAAATTT TTACTGGTAA ATGAATAAAG AATATTGTGG       1932

AAAACTCACT GTCTCTAAAG TTTATGAAAA CATTGTTGGC TAATATATTG TGAATCAAAG       1992

TTTTTCTTTA GACGACTTAG GATATTATGG GGCTAGGCAT TTTTTCCTCA ATAGAGTCTT       2052

CCTCTCATCC TCTTTCTTGT CTCCTAGTTA CATTCTTTTA CTTCCATCCA TACTTTGCCA       2112

CAAGAGAAGG AACATGAGCT TTATTGTGTA GATCTGATTT GAAATCCTGT GGACACGGGG       2172
```

| | | | | |
|---|---|---|---|---|
| TGAATTACTT | TTAAAATCTG | TGGCTCTGAT | TCCTCAAAGA | TAAAATGCAA ATAATATTTA 2232 |
| TATAATTCAC | TGCCAGATAT | AAATTTTCAA | AACTATTTGT | TATATGGATG AATAACATCA 2292 |
| TTAATATTGT | GGTTGCTGGG | CCAGCATTTG | CCAAAAGTTC | TCCTTCCATT TTGCTTTATT 2352 |
| TTCCTGTAAC | TTGAAATTCT | GGTCCTACTG | TCATCTGCCT | GCTTCTTCCT TAATTAAATA 2412 |
| TTGATAGGAT | ATCAGATGTC | TCGGATCTGA | GAGTGTGCCT | TGTGATTCAA AATCTGAATC 2472 |
| TTTACTTATC | CATAACTCAG | ATTTTCTGTT | TGTAAATTCC | AGTATCAGGG CTATAGTTTA 2532 |
| AACTGCAGAT | TTGTTCTTAA | CACTATTCTC | CCTCTTCGAC | TCGTGATGAC TATAATAATC 2592 |
| TTAAGAGAAA | AGCAGACATT | AGAATGAATA | AATATTCATT | AGGAGAATAA ATTACATTGA 2652 |
| AGCATCAGTA | TTTTAGGCAG | CAGTGTAATA | GTTGGGAGAT | ACTGGTGAGT GTAGATATCC 2712 |
| TAGGAAGAGG | TGGATAGGAG | ATCTGGCCTC | AGTGGGAAGG | ACAAATGAAA GACATATAGC 2772 |
| AATATTTGAG | AGCTTGTCAT | CTTTCTTACC | TATTAGCCTT | GTTCAGCTCT CCTGCTATCT 2832 |
| TGTTGCAATG | CCAGGTCACC | ACTGGTGCTC | CTAGGCAGAC | CCAAGTTTCT CACATTCTGA 2892 |
| GCAAGATCAC | ATCACAGGAG | GATGTGGTGG | CAAAAAACAA | AATGAAAAC AAAACAATCA 2952 |
| AACAAAAAAC | CAGATAAAAA | TGTGGCTCAA | GTATGAGATA | CAGTTGTATC AATGAATCAA 3012 |
| GTAAATTATA | TTGCACACGA | GTATCTGAAC | CTAATTCAGT | TGTTTGTTCT TGATTATATA 3072 |
| TATGTACATA | TGGAAAAAGC | AAAAATATGT | TCAGAGAGAT | TCAGAAATAC ACAATTTCGC 3132 |
| TTCCAGGTTG | AAGCCTTCTG | CCCTTATTAT | GCAATGTTAC | CTTTTCTCTA ATGAAATCTA 3192 |
| AATGAGTGAA | GAAGAATCTC | ACCAATTGAT | TTGGCCAGAG | ATTTTAAGGT GCCTCTTAAT 3252 |
| TGTTTGTGTT | TGTCCAAACC | CATGTCTCTG | TTTTTGGTGG | CCCCCTGGAG ACTAGGATGT 3312 |
| GGCATATCTT | GGTAGAACTC | TGAGATAAGT | AAGGTAGAAA | CCAAACCTTC TAGACGTAAC 3372 |
| TGGGAAGGTA | GGATCTTGGA | TGTATATTCC | AGTTCTTCTA | TTTTCAAGGT GAAGCTGAGT 3432 |
| GTGTGTTTTT | ATCTGCCACT | CTCTCTGCTG | AAAGCCAGGG | AGATTATATG GGGCAAGTAC 3492 |
| CCATACTGGT | GTTCAGGCGG | CAGCCTCTGA | TCCTAGGAGA | TACCTATTGA AGTAAGCCTA 3552 |
| CGTCATATCC | ACCTATTTGT | TTTTTGTGGC | CTAGGGACAT | TCAGGAATGG AAAGCCCCAC 3612 |
| TGATTCCCAG | AGCTAGTTCA | TTAAGAAGAC | AGTGCCTTTG | GTGGGAGCTA TAAGTTGT 3672 |
| GGCTCTTGGT | GTGTGAACTA | ACTCCTTCAA | GGTAAATGAA | TAGGCCTAGA TTTATTACTG 3732 |
| GGGTGAGCTG | GAAGAAAGGC | TCAGGAAGTG | CCAAGCTGTG | GCTCAGGTTA CTGGAGGGCT 3792 |
| ACTATTGCT | CACCAATGCA | AATGTATTAG | AAGCAAGCTT | GTCAAATAGT CATGGAAAGA 3852 |
| ATGTGCAGGA | AAATCCTTCT | GGAGGGAAAA | ATGGGAGCTG | TGCATTCCAG AATTTTTCT 3912 |
| GCACTGCACC | CAGAGGATGT | AGCCCCTGGA | AGTACTTAGA | TGCCCATTGA AAACCACCTC 3972 |
| TTTGTCCTAT | AATCTAGAGA | GACTCACATG | TGCCTTCTTC | CGTTCTTTGA GCTAGAAGGT 4032 |
| ATTAGGATT | CAGTTAATCG | TGGTTGCTAT | AAAAGTTGCA | GCACCTAATG TATGGCATAA 4092 |
| ATAAATCCTT | TCTGGGAAGA | ACACGGAGC | TGCATTTTTA | GAGTTCCTTC TCCACACTCC 4152 |
| TCCCATAGTA | TGAAGTCTGT | GGAAGTGCAT | GCAGGCTCAT | ATAACTGCCT TTTCCTGTGG 4212 |
| CCTAGAGAGA | CTTGCATACA | CCTAGTCCCC | TCTACCCCAG | AGTTGGGAGG TTTAGGATGC 4272 |
| AGTCCTAAGA | GTGGAAAGAG | TGGACAAACT | CTTTTCAGGT | CGGATTAATA GACCTGCAAT 4332 |
| TATCACTGGG | GTTAGGGGAG | AAAGCACGGG | AAGAGACAAT | CTCCTTCTCA GGCTGCTAGT 4392 |
| GGGATATTTG | TCTCCTTTCT | CCCCAGTGCA | TGTTGGAAAC | CAGGCCACCA AGTAGCCACT 4452 |
| GGAACAGTGT | GCCATAAACC | CATTCCGGAG | GAAGTGACAG | ACAGCTGCAT TTTAAAGCCC 4512 |
| CTTCTGTACA | TTGCTACTGG | GGGATAAGGC | TCCTGGAAAT | GCTATGCACC TGTATAAAAT 4572 |

| | | | | | |
|---|---|---|---|---|---|
| CACCTTTTTC | CTGTGGTCTA | GAGAGACTTG | CATATGTCTA | ATTCCCTCTA | CTTCAAGAGG | 4632
| TAGGAGGTTG | AGGATGTAGT | CTTAGGTGGA | AGCTGTAATA | GTGGGATGCT | CATCATGTGG | 4692
| ACAAACTCTA | GGAGGAATCA | GTAGACACAA | AATTATAGCT | GACTAGATTG | GGAGAGGCAG | 4752
| TTGTCTCATC | TAACATACAG | AAACTAACAC | AGAAAGTCAA | AGAAAATGAT | GAAACAGAGA | 4812
| TATATATTCC | AATTAAAAAA | CAAATAAAT | TTCCGAAACT | GTACCCAAGT | GATGTGGAGA | 4872
| TATGCAATTT | ACCTGACAGG | GAATTAGAAT | AAGGTCATAA | AGATGCTCTC | TGATCAGGTG | 4932
| ACCAATGTAG | GAACAAAACT | GTGAATTTCA | ACAAGAGAT | TTTTAAAGT | TTTTAAAACA | 4992
| CCAGACGAAA | TTATAGAACT | GAAAATACT | CTGACTAAAA | AATCTAATAG | AGATGTTCAA | 5052
| CAGCAGGCTA | CATCAAACAG | AAGAAAGAAT | CAGGGAACTC | AAGAACAGG | TCATTGAAAG | 5112
| TTATCAAGTT | TCTGTTTCAA | GAACCAGAAA | TACCATTTGA | CCCAGCAATC | CATTACTGGG | 5172
| TATATACACA | AAGGAATATA | AATCATTCTG | TTCTAAAGAC | ACATACATGG | GTATGTTCAC | 5232
| TGCAGCACTA | TTCGCAATAG | CAGAGATGTG | GAATCAATCT | AAATGCCCAT | CAATGATACA | 5292
| CTGGATAAAG | AAAATGTGGT | ACATATACAC | CATGGAATAC | TATGCAGCTA | TAAGAAAGAA | 5352
| TGAGATCATG | TCCTTTGCAG | AAACATGGAT | GAAGCTGGAG | GCCATTATCC | TTAGCAAACC | 5412
| AATGCAGAAA | CAGAAAACCA | AATACCACAT | GTTCTTACTT | GTAAGTGGGA | GCTAAATGAT | 5472
| GAGAACACAT | GGACACATAG | AGGGGAACAA | CTCACACTGG | GGCCTACTGG | GGTGAAGAGT | 5532
| AGGAGGAGAG | AGAGAAGCAG | AAAAAATAAA | TAATGCGTAC | TAGGCTTACT | ACCTGCGTGA | 5592
| CAAAGTTAAT | CTGCAAAACA | ACCCCATGAC | ACGAGTTTAT | CTATATAACA | AACCTGCACA | 5652
| TGTTAGCCCC | TGAACTTAAA | ATAAAAATTA | AATTTAAAAA | ATAAGATTAA | TATCTGCATA | 5712
| CAAATCTTTG | TTTACAGCTT | GTTATATACT | GAATTATGTC | TGCTCCCCCA | ACATTCATAT | 5772
| GTTAAAGCCC | AAAGTTATTG | TGTTTGGAAA | TAGGGCTTTT | AGGAGATATT | TAAGGTTAAA | 5832
| TAAGGTTATA | AACGTGGAGT | CTTAATCTGA | TAGGATTGGT | GGCTTTATAA | GAAAAGAAA | 5892
| AGAGATTGCT | CTCTCCCCAG | TGCAGTTACC | AAGGAAAGGC | CATGTGAGAA | CATAGCAGGA | 5952
| AGGGCAGCCA | TCTGTAACCT | AAGGAAAGAG | ATCTGTCAAA | GGACAAAACT | ACAACAAATG | 6012
| TAAAGATCTC | AATTGGCTTT | ATCTGCGATT | CTGGAATCAG | GCAATACTCC | ATTTCATAAA | 6072
| ACAGAACTAG | TGCTCCAATG | AGCTGAGCAA | AAGGGGTTGT | TAGTTTTATA | GACAGAGAAG | 6132
| GACGGAAGAA | AGCAGAAATA | ACGAATGGAA | AGTAGATTGG | TCAAATTTAC | TTTCCTTTTA | 6192
| AGGCAGAAAA | ATAGAACAAT | AACTATTCAA | GTAATCTTAA | GGTTACTTCA | GGTTAAGGGT | 6252
| TAAAAACAGA | AGGAATTTTA | TCATCATGCT | TATTGAAGAT | TCAAACTGGC | CTGTTTAAGA | 6312
| AATTGGCTGT | TATCTCTTTC | TATCTTTTAT | TTTAAGAGGC | TTCCTCAGAT | ACCATGCTGG | 6372
| TGGAAGAAGG | GGAGTGCCAC | CTTTCTACGG | CCAGGTGGAC | ATAAATATCC | AAGTTCCCCA | 6432
| TTCAATCTCC | TTGCCATTCA | AGGCAAGGTA | CC | | | 6464

( 2 ) INFORMATION FOR SEQ ID NO:3:

( i ) SEQUENCE CHARACTERISTICS:
        ( A ) LENGTH: 2768 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 2220..2320

( x i ) SEQUENCE DESCRIPTION: SEQ ID NO:3:

```
GGATCCTTGA CTCTGGTCTT ACTCTCCCTT AGTCACAAGT CTCCTCATCT CATAGTTTCC    60
CATGACGGTT CTTGCTGGAC ATCCTCAAGG ATCTCTGTCA AACTGACAAT AATTAGAGGC   120
AATCTCAGAA TTACGCATGT GCCAATCTGG ATTGCAACAT TTAATTCCA  GGTGTCAGGT   180
TTCCAACAAT CAAGGAGAAA AATGACCATA ATCCATTGAC AATTCCTCTC CCACACTCAG   240
TCAAAAATGG TCCAGATCAC AGTCCTACAT GCTGGAATTA TTTCCTCTGC TTCTCTCTCA   300
CCCCACCTTG GCCAAAGATT TTCTAGCAAG ATCTGAATTT TAATCCATCT CTCTTCGCCT   360
GTGTGTCCCG ACTAATTTGG CAGAAGGAAT TCTTTCTTAA ACCTTGCCAT TTAATTCACA   420
AATGGAAATG TGAAGGGTCA ATAGGTATGT GAAGAACCTA TTCACCCGTA TTCACTGGGA   480
ATCAGAGAAG TGAAAATGGA AAGAACACT  GAGCTATCAT CTTAGATACA CAAAACTGTC   540
AAACATTTGA AGGTGGCTAA CACCAAATGT CAATCAGGAT ATGAGGAAAG TAGGAATTCT   600
TCTATACAAG AGGACAGAAA TCTGGCAGTG CCAAAAGAAA AACTACATCT ATGATCTGCC   660
CCTCCGCAGA TCCCATTCCT AATACATATA TCCCAGCGAG TTCTGCTAAT CTGCAGAGGA   720
TGTCTAGAAA CGCATTCATC ACATCAGTGT TTATAATAAC CAGGAGTAGG AGGCAATCAA   780
ATGTCCTTCA CAAGTGGAAC TGGTAAGTTA AAGAGACTTA GGTTGGGTTT CTCTAAAACC   840
AGGCCACAAG ACAAAGATTT GTATTCCAGT GGCTTATTTT GATTTAGGAG ATGATTTAAG   900
GAATCACCAG TGCGGGAGGT ATAACAGTGA ACCCAAGACA CCTTGAGATC AATAAAAAGG   960
TGCATTGTTG GCAGGCTGCC TGCAAGAAG  GGAGCATATC CAGTAGACAC ACCAGGAGGC  1020
AGTTTGTACA TGCCTAAGAG TAATCCCACC TTAGCTGTAG AACACAAGGA TATTTAGTCT  1080
CCAGTTCCCA TCATGTGGGC TGAGTGGTGG TCCCAGGTGC TTTAATTTGT AGTCCATCTG  1140
CCCAAGCACA GGCCAAAAGA AAGCCTTCCC ACAGAGTCCC GAGTTCATGT GGCAGCATGC  1200
CAGAGGTATG TACTGGAACA GTAGGTGCGA AAGGCAACAA TTACATCATG AAAACTGCAC  1260
ATCTCACTCA TATGTGGAAT CTAAAGTAAT TTAGCTCATA GAAGTTAAGA GTAGAATAGT  1320
TAGAGTAGTA GAAAGTTAAG AGTTGTTACT GGAGAGAAAA GAGGGTATGA AGCTAGAAAA  1380
AAAGCTAGAA GGAAGGATTT TGAATGTTCT CATGACAAAG AGATGATAAA TGTTTGAGGT  1440
GACAGACATG CTAATTACCA TGATTTGATC TTTACACAAT GTCTGCATGT ATCAGAACAT  1500
CACACACTAC CAAATAAATA TATACAATTG TTATGTGTCA AAAAACATTA TATACAATGT  1560
TTATATTTTA TATTAATATT AATGTAAATA AAAATTTACA CAAATCTTTT CATTAAATAT  1620
GGTGTGGATA ATTATATTAT CTGATGATAC CCATGCCACA GGCTAGGAGA AGTAAATATT  1680
TACATTAATG TTAATGTCAA AAAAGCAGAA ACAAAGCCAT ATGATACATG TCACACTTAT  1740
ACCACATGCA TAGAGTTATT TCAGACACAT TGTGTGTTAC CTTTGGGTAG AGAAGTGAAT  1800
GAGAGTGAGG ATGAGAGATG AAAAGAGGCA GAAGAAAAA  GAGAGGCCTT ATAGGAAGTG  1860
ATGAAAGTGT GCCATAAACT GAGAGTATGA CTAAAACCTT TCATCTTCCT CTTCTGCCGC  1920
TTCTAAGTTA TTGGTTCTGC TGTTCCTTGA CCTGTTTCAA GCTCTCACCT TCTATATCAC  1980
ACATGGGAAG TCTGGCATCA GACTTCCAGA GAGCAAGAAC TAGGTGAAAT ACAAGGGCAC  2040
AGCTCTCCTA GCCTGTGGCA TGGGTATCAT CAGATAATAT AATTATCCAC ACCATTTTTA  2100
ACGAAAAGAT TTGCGTAAGA GATTCACAGA GGCAACCTGA GGCCCTGCAA CTACATTTCC  2160
CAGAGATCCC TGAGGTGATC CTAACTAGAC TCTGGTGTCA GGGTGATACG GAATTCCAGT  2220
GAGATCACTT CCCTTGCAGA CTTTGGAAGG GAGAGCACTT TATTACAGAC CTTGGAAGCA  2280
AGAGGATTGC ATTCAGCCTA GTTCCTGGTT GCTGGCCAAA GTAAGTAGAA CTTTGTAAGT  2340
AATTTGCAGT GTACTTTGAA AGTGGGGTAT AAATTAAAAA TAAAATCAAG TCCCCCTACT  2400
```

5,527,677

37                                                                                      38

-continued

| GACTGAATGG | ATCCCCTCTT | GTCCTAGGCG | ACCCCAGAGA | AACCTGGAAA | ACTAAATTCC | 2460 |
| AGGCCATAAT | GGAAAGGGAG | GTCAGACACG | CCTCATTATA | CACACTCCCT | TTTGGAGTTC | 2520 |
| AGGCACAACT | GACCAGCATT | AACATTGAAA | CAGTGATCAT | AAGACTGTCA | AAATGGACTG | 2580 |
| TTTGTGGGAA | TAAGATACCA | AATTCCAATC | TGACTCTGGT | TTAGCATCAC | ATGACAATAG | 2640 |
| CAGACCCTGA | AGGAAATCAA | TATATTTAAT | CCCAAAATAT | ATTTCTTTGA | CACATATTGA | 2700 |
| ATGGTCTTGC | AAACCATCTT | TATGGGAATT | TGCTGGTTTC | TGGCTCTGCT | CTGATTGAGG | 2760 |
| AGAGATAA   |            |            |            |            |            | 2768 |

( 2 ) INFORMATION FOR SEQ ID NO:4:

( i ) SEQUENCE CHARACTERISTICS:
    ( A ) LENGTH: 6464 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 723..1595

( i x ) FEATURE:
    ( A ) NAME/KEY: exon
    ( B ) LOCATION: 717..1936

( i x ) FEATURE:
    ( A ) NAME/KEY: polyA_signal
    ( B ) LOCATION: 1794..1799

( i x ) FEATURE:
    ( A ) NAME/KEY: polyA_signal
    ( B ) LOCATION: 1800..1805

( x i ) SEQUENCE DESCRIPTION: SEQ ID NO:4:

| GAATTCAGTG | TCTCTCCCTG | TGCACCCACT | AACCCCTCTT | TTTGTTTTCA | CCAGGCACTT | 60 |
| ACCACAATCT | AACAGACTGC | ATGTTTTATC | CATTTATTCA | GTTCCTATT  | TGTGTCCCTT | 120 |
| CAACTCCCAT | TAAAATATAA | TATTTTTGAG | GGCAAGCAAG | TACTAGAACA | ATAGGAAACA | 180 |
| CATCAAGAGT | ATTCTGTAAA | CTATTTCTTG | AATCAATCAG | TGAATGAATG | AATTAATCAA | 240 |
| TATATTTTTT | GAGTGAGGAG | CTTTGTGTTA | GGTACAGCTA | AATGGGAAAT | CAAGTGGGTC | 300 |
| ATGTACCATG | AATACCATAT | ACTCTACTGT | ATAATTCTCC | TGCTTATATC | AGAAACTGTT | 360 |
| TATAAGCCTA | TTATAATTGA | TACCAATTGG | AATCTCTTTT | TTACTCATCA | CCAAGAACAC | 420 |
| CACAAACAAG | TTGTTTACCA | TTTGGCTCCT | TATTTAATCT | GGATTCCAA  | CTCCTCATGC | 480 |
| TTAAAAGACG | GAAGATACAA | TAATACTTTC | CTTACAGGGT | TCTGAGACTA | CTAAGAGAAC | 540 |
| TTATGCATGT | AAAAGGGATT | CATGCAGTAG | AAATACTAAC | AAAAGAATTA | CTATGACAGA | 600 |
| TACTTATAAC | CATTGTGTTT | TTACGTATTT | AAAATACGTT | ATACCTATAA | TTAGTCACAC | 660 |
| GAGGAAATCA | AATGCTAAAG | TATGATATGT | TTTTATGTTT | TGTTTTCTT  | GCTTAGGGGA | 720 |

```
TC ATG GAC ATT GAA GCA TAT TTT GAA AGA ATT GGC TAT AAG AAC TCT      767
   Met Asp Ile Glu Ala Tyr Phe Glu Arg Ile Gly Tyr Lys Asn Ser
   1               5                  10                  15

AGG AAC AAA TTG GAC TTG GAA ACA TTA ACT GAC ATT CTT GAG CAC CAG      815
Arg Asn Lys Leu Asp Leu Glu Thr Leu Thr Asp Ile Leu Glu His Gln
                20                  25                  30

ATC CGG GCT GTT CCC TTT GAG AAC CTT AAC ATG CAT TGT GGG CAA GCC      863
Ile Arg Ala Val Pro Phe Glu Asn Leu Asn Met His Cys Gly Gln Ala
            35                  40                  45
```

| | | |
|---|---|---|
| ATG GAG TTG GGC TTA GAG GCT ATT TTT GAT CAC ATT GTA AGA AGA AAC<br>Met Glu Leu Gly Leu Glu Ala Ile Phe Asp His Ile Val Arg Arg Asn<br>50 55 60 | | 911 |
| CGG GGT GGG TGG TGT CTC CAG GTC AAT CAA CTT CTG TAC TGG GCT CTG<br>Arg Gly Gly Trp Cys Leu Gln Val Asn Gln Leu Leu Tyr Trp Ala Leu<br>65 70 75 | | 959 |
| ACC ACA ATC GGT TTT CAG ACC ACA ATG TTA GGA GGG TAT TTT TAT ATC<br>Thr Thr Ile Gly Phe Gln Thr Thr Met Leu Gly Gly Tyr Phe Tyr Ile<br>80 85 90 95 | | 1007 |
| CCT CCA GTT AAC AAA TAC AGC ACT GGC ATG GTT CAC CTT CTC CTG CAG<br>Pro Pro Val Asn Lys Tyr Ser Thr Gly Met Val His Leu Leu Leu Gln<br>100 105 110 | | 1055 |
| GTG ACC ATT GAC GGC AGG AAT TAC ATT GTC GAT GCT GGG TCT GGA AGC<br>Val Thr Ile Asp Gly Arg Asn Tyr Ile Val Asp Ala Gly Ser Gly Ser<br>115 120 125 | | 1103 |
| TCC TCC CAG ATG TGG CAG CCT CTA GAA TTA ATT TCT GGG AAG GAT CAG<br>Ser Ser Gln Met Trp Gln Pro Leu Glu Leu Ile Ser Gly Lys Asp Gln<br>130 135 140 | | 1151 |
| CCT CAG GTG CCT TGC ATT TTC TGC TTG ACA GAA GAG AGA GGA ATC TGG<br>Pro Gln Val Pro Cys Ile Phe Cys Leu Thr Glu Glu Arg Gly Ile Trp<br>145 150 155 | | 1199 |
| TAC CTG GAC CAA ATC AGG AGA GAG CAG TAT ATT ACA AAC AAA GAA TTT<br>Tyr Leu Asp Gln Ile Arg Arg Glu Gln Tyr Ile Thr Asn Lys Glu Phe<br>160 165 170 175 | | 1247 |
| CTT AAT TCT CAT CTC CTG CCA AAG AAG AAA CAC CAA AAA ATA TAC TTA<br>Leu Asn Ser His Leu Leu Pro Lys Lys Lys His Gln Lys Ile Tyr Leu<br>180 185 190 | | 1295 |
| TTT ACG CTT GAA CCT CGA ACA ATT GAA GAT TTT GAG TCT ATG AAT ACA<br>Phe Thr Leu Glu Pro Arg Thr Ile Glu Asp Phe Glu Ser Met Asn Thr<br>195 200 205 | | 1343 |
| TAC CTG CAG ACG TCT CCA ACA TCT TCA TTT ATA ACC ACA TCA TTT TGT<br>Tyr Leu Gln Thr Ser Pro Thr Ser Ser Phe Ile Thr Thr Ser Phe Cys<br>210 215 220 | | 1391 |
| TCC TTG CAG ACC CCA GAA GGG GTT TAC TGT TTG GTG GGC TTC ATC CTC<br>Ser Leu Gln Thr Pro Glu Gly Val Tyr Cys Leu Val Gly Phe Ile Leu<br>225 230 235 | | 1439 |
| ACC TAT AGA AAA TTC AAT TAT AAA GAC AAT ACA GAT CTG GTC GAG TTT<br>Thr Tyr Arg Lys Phe Asn Tyr Lys Asp Asn Thr Asp Leu Val Glu Phe<br>240 245 250 255 | | 1487 |
| AAA ACT CTC ACT GAG GAA GAG GTT GAA GAA GTG CTG AAA AAT ATA TTT<br>Lys Thr Leu Thr Glu Glu Glu Val Glu Glu Val Leu Lys Asn Ile Phe<br>260 265 270 | | 1535 |
| AAG ATT TCC TTG GGG AGA AAT CTC GTG CCC AAA CCT GGT GAT GAA TCC<br>Lys Ile Ser Leu Gly Arg Asn Leu Val Pro Lys Pro Gly Asp Glu Ser<br>275 280 285 | | 1583 |
| CTT ACT ATT TAGAATAAGG AACAAAATAA ACCCTTGTGT ATGTATCACC<br>Leu Thr Ile<br>290 | | 1632 |
| CAACTCACTA ATTATCAACT TATGTGCTAT CAGATATCCT CTCTACCCTC ACGTTATTTT | | 1692 |
| GAAGAAAATC CTAAACATCA AATACTTTCA TCCATAAAAA TGTCAGCATT TATTAAAAAA | | 1752 |
| CAATAACTTT TTAAAGAAAC ATAAGGACAC ATTTTCAAAT TAATAAAAAT AAAGGCATTT | | 1812 |
| TAAGGATGGC CTGTGATTAT CTTGGGAAGC AGAGTGATTC ATGCTAGAAA ACATTTAATA | | 1872 |
| TTGATTTATT GTTGAATTCA TAGTAAATTT TTACTGGTAA ATGAATAAAG AATATTGTGG | | 1932 |
| AAAACTCACT GTCTCTAAAG TTTATGAAAA CATTGTTGGC TAATATATTG TGAATCAAAG | | 1992 |
| TTTTTCTTTA GACGACTTAG GATATTATGG GGCTAGGCAT TTTTTCCTCA ATAGAGTCTT | | 2052 |
| CCTCTCATCC TCTTTCTTGT CTCCTAGTTA CATTCTTTTA CTTCCATCCA TACTTTGCCA | | 2112 |

-continued

```
CAAGAGAAGG AACATGAGCT TTATTGTGTA GATCTGATTT GAAATCCTGT GGACATGGGG   2172
TGAATTACTT TTAAAATCTG TGGCTCTGAT TCCTCAAAGA TAAAATGCAA ATAATATTTA   2232
TATAATTCAC TGCCAGATAT AAATTTTCAA AACTATTTGT TATATGGATG AATAACATCA   2292
TTAATATTGT GGTTGCTGGG CCAGCATTTG CCAAAAGTTC TCCTTCCATT TTGCTTTATT   2352
TTCCTGTAAC TTGAAATTCT GGTCCTACTG TCATCTGCCT GCTTCTTCCT TAATTAAATA   2412
TTGATAGGAT ATCAGATGTC TCGGATCTGA GAGTGTGCCT TGTGATTCAA AATCTGAATC   2472
TTTACTTATC CATAACTCAG ATTTTCTGTT TGTAAATTCC AGTATCAGGG CTATAGTTTA   2532
AACTGCAGAT TTGTTCTTAA CACTATTCTC CCTCTTCGAC TCGTGATGAC TATAATAATC   2592
TTAAGAGAAA AGCAGACATT AGAATGAATA AATATTCATT AGGAGAATAA ATTACATTGA   2652
AGCATCAGTA TTTTAGGCAG CAGTGTAATA GTTGGGAGAT ACTGGTGAGT GTAGATATCC   2712
TAGGAAGAGG TGGATAGGAG ATCTGGCCTC AGTGGGAAGG ACAAATGAAA GACATATAGC   2772
AATATTTGAG AGCTTGTCAT CTTTCTTACC TATTAGCCTT GTTCAGCTCT CCTGCTATCT   2832
TGTTGCAATG CCAGGTCACC ACTGGTGCTC CTAGGCAGAC CCAAGTTTCT CACATTCTGA   2892
GCAAGATCAC ATCACAGGAG GATGTGGTGG CAAAAACAA AAATGAAAAC AAAACAATCA    2952
AACAAAAAAC CAGATAAAAA TGTGGCTCAA GTATGAGATA CAGTTGTATC AATGAATCAA   3012
GTAAATTATA TTGCACACGA GTATCTGAAC CTAATTCAGT TGTTTGTTCT TGATTATATA   3072
TATGTACATA TGGAAAAAGC AAAAATATGT TCAGAGAGAT TCAGAAATAC ACAATTTCGC   3132
TTCCAGGTTG AAGCCTTCTG CCCTTATTAT GCAATGTTAC CTTTTCTCTA ATGAAATCTA   3192
AATGAGTGAA GAAGAATCTC ACCAATTGAT TTGGCCAGAG ATTTTAAGGT GCCTCTTAAT   3252
TGTTTGTGTT TGTCCAAACC CATGTCTCTG TTTTTGGTGG CCCCCTGGAG ACTAGGATGT   3312
GGCATATCTT GGTAGAACTC TGAGATAAGT AAGGTAGAAA CCAAACCTTC TAGACGTAAC   3372
TGGGAAGGTA GGATCTTGGA TGTATATTCC AGTTCTTCTA TTTTCAAGGT GAAGCTGAGT   3432
GTGTGTGTTT ATCTGCCACT CTCTCTGCTG AAAGCCAGGG AGATTATATG GGGCAAGTAC   3492
CCATACTGGT GTTCAGGCGG CAGCCTCTGA TCCTAGGAGA TACCTATTGA AGTAAGCCTA   3552
CGTCATATCC ACCTATTTGT TTTTTGTGGC CTAGGGACAT TCAGGAATGG AAAGCCCCAC   3612
TGATTCCCAG AGCTAGTTCA TTAAGAAGAC AGTGCCTTTG GTGGGAGCTA TATAAGTTGT   3672
GGCTCTTGGT GTGTGAACTA ACTCCTTCAA GGTAAATGAA TAGGCCTAGA TTTATTACTG   3732
GGGTGAGCTG GAAGAAAGGC TCAGGAAGTG CCAAGCTGTG GCTCAGGTTA CTGGAGGGCT   3792
ACTGTTTGCT CACCAATGCA AATGTATTAG AAGCAAGCTT GTCAAATAGT CATGGAAAGA   3852
ATGTGCAGGA AAATCCTTCT GGAGGGAAAA ATGGGAGCTG TGCATTCCAG AATTTTTTCT   3912
GCACTGCACC CAGAGGATGT AGCCCCTGGA AGTACTTAGA TGCCCATTGA AAACCACCTC   3972
TTTGTCCTAT AATCTAGAGA GACTCACATG TGCCTTCTTC CGTTCTTTGA GCTAGAAGGT   4032
ATTTAGGATT CAGTTAATCG TGGTTGCTAT AAAAGTTGCA GCACCTAATG TATGGCATAA   4092
ATAAATCCTT TCTGGGAAGA AACACGGAGC TGCATTTTTA GAGTTCCTTC TCCACACTCC   4152
TCCCATAGTA TGAAGTCTGT GGAAGTGCAT GCAGGCTCAT ATAACTGCCT TTTCCTGTGG   4212
CCTAGAGAGA CTTGCATACA CCTAGTCCCC TCTACCCCAG AGTTGGGAGG TTTAGGATGC   4272
AGTCCTAAGA GTGGAAAGAG TGGACAAACT CTTTTCAGGT TGGATTAATA GACCTGCAAT   4332
TATCACTGGG GTTAGGGGAG AAAGCACGGG AAGAGACAAT CTCCTTCTCA GGCTGCTAGT   4392
GGGATATTTG TCTCCTTTCT CCCCAGTGCA TGTTGGAAAC CAGGCCACCA AGTAGCCACT   4452
GGAACAGTGT GCCATAAACC CATTCCGGAG GAAGTGACAG ACAGCTGCAT TTTAAAGCCC   4512
```

```
CTTCTGTACA  TTGCTCCTGG  GGGATAAGGC  TCCTGGAAAT  GCTATGCACC  TGTATAAAAT    4572
CACCTTTTTC  CTGTGGTCTA  GAGAGACTTG  CATATGTCTA  ATTCCCTCTA  CTTCAAGAGG    4632
TAGGAGGTTG  AGGATGTAGT  CTTAGGTGGA  AGCTGTAATA  GTGGGATGCT  CATCATGTGG    4692
ACAAACTCTA  GGAGGAATCA  GTAGACACAA  AATTATAGCT  GACTAGATTG  GGAGAGGCAG    4752
TTGTCTCATC  TAACATACAG  AAACTAACAC  AGAAAGTCAA  AGAAAATGAT  GAAACAGAGA    4812
TATATATTCC  AATTAAAAAA  CAAATAAAT   TTCCGAAACT  GTACCCAAGT  GATGTGGAGA    4872
TATGCAATTT  ACCTGACAGG  GAATTAGAAT  AAGGTCATAA  AGATGCTCTC  TGATCAGGTG    4932
ACCAATGTAG  GAACAAAACT  GTGAATTTCA  ACAAAGAGAT  TTTTAAAGT   TTTTAAAACA    4992
CCAGACGAAA  TTATAGAACT  GAAAATACT   CTGACTAAAA  AATCTAATAG  AGATGTTCAA    5052
CAGCAGGCTA  CATCAAACAG  AAGAAAGAAT  CAGGGAACTC  AAAGAACAGG  TCATTGAAAG    5112
TTATCAAGTT  TCTGTTTCAA  GAACCAGAAA  TACCATTTGA  CCCAGCAATC  CATTACTGGG    5172
TATATACACA  AAGGAATATA  AATCATTCTG  TTCTAAAGAC  ACATACATGG  GTATGTTCAC    5232
TGCAGCACTA  TTCGCAATAG  CAAAGATGTG  GAATCAATCT  AAATGCCCAT  CAATGATACA    5292
CTGGATAAAG  AAAATGTGGT  ACATATACAC  CATGGAATAC  TATGCAGCTA  TAAGAAAGAA    5352
TGAGATCATG  TCCTTTGCAG  AAACATGGAT  GAAGCTGGAG  GCCATTATCC  TTAGCAAACC    5412
AATGCAGAAA  CAGAAAACCA  AATACCACAT  GTTCTTACTT  GTAAGTGGGA  GCTAAATGAT    5472
GAGAACACAT  GGACACATAG  AGGGGAACAA  CTCACACTGG  GGCCTACTGG  GGTGAAGAGT    5532
AGGAGGAGAG  AGAGAAGCAG  AAAAAATAAA  TAATGCGTAC  TAGGCTTACT  ACCTGCGTGA    5592
CAAAGTTAAT  CTGCAAAACA  ACCCCATGAC  ACGAGTTTAT  CTATATAACA  AACCTGCACA    5652
TGTTAGCCCC  TGAACTTAAA  ATAAAAATTA  AATTTAAAAA  ATAAGATTAA  TATCTGCATA    5712
CAAATCTTTG  TTTACAGCTT  GTTATATACT  GAATTATGTC  TGCTCCCCCA  ACATTCATAT    5772
GTTAAAGCCC  AAAGTTATTG  TGTTTGGAAA  TAGGGCTTTT  AGGAGATATT  TAAGGTTAAA    5832
TAAGGTTATA  AACGTGGAGT  CTTAATCTGA  TAGGATTGGT  GGCTTTATAA  GAAAAAGAAA    5892
AGAGATTGCT  CTCTCCCCAG  TGCAGTTACC  AAGGAAAGGC  CATGTGAGAA  CATAGCAGGA    5952
AGGGCAGCCA  TCTGTAACCT  AAGGAAAGAG  ATCTGTCAAA  GGACAAAACT  ACAACAAATG    6012
TAAAGATCTC  AATTGGCTTT  ATCTGCGATT  CTGGAATCAG  GCAATACTCC  ATTTCATAAA    6072
ACAGAACTAG  TGCTCCAATG  AGCTGAGCAA  AAGGGGTTGT  TAGTTTTATA  GACAGAGAAG    6132
GACGGAAGAA  AGCAGAAATA  ACGAATGGAA  AGTAGATTGG  TCAAATTTAC  TTTCCTTTTA    6192
AGGCAGAAAA  ATAGAACAAT  AACTATTCAA  GTAATCTTAA  GGTTACTTCA  GGTTAAGGGT    6252
TAAAAACAGA  AGGAATTTTA  TCATCATGCT  TATTGAAGAT  TCAAACTGGC  CTGTTTAAGA    6312
AATTGGCTGT  TATCTCTTTC  TATCTTTTAT  TTTAAGAGGC  TTCCTCAGAT  ACCATGCTGG    6372
TGGAAGAAGG  GGAGTGCCAC  CTTTCTACGG  CCAGGTGGAC  ATAAATATCC  AAGTTCCCCA    6432
TTCAATCTCC  TTGCCATTCA  AGGCAAGGTA  CC                                    6464
```

( 2 ) INFORMATION FOR SEQ ID NO:5:

( i ) SEQUENCE CHARACTERISTICS:
        ( A ) LENGTH: 2768 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: exon
        ( B ) LOCATION: 2220..2320

( x i ) SEQUENCE DESCRIPTION: SEQ ID NO:5:

| | | | | | | |
|---|---|---|---|---|---|---|
| GGATCCTTGA | CTCTGGTCTT | ACTCTCCCTT | AGTCACAAGT | CTCCTCATCT | CATAGTTTCC | 60 |
| CATGACGGTT | CTTGCTGGAC | ATCCTCAAGG | ATCTCTGTCA | AACTGACAAT | AATTAGAGGC | 120 |
| AATCTCAGAA | TTACGCATGT | GCCAATCTGG | ATTGCAACAT | TTTAATCCCA | GGTGTCAGGT | 180 |
| TTCCAACAAT | CAAGGAGAAA | AATGACCATA | ATCCATTGAC | AATTCCTCTC | CCACACTCAG | 240 |
| TCAAAAATGG | TCCAGATCAC | AGTCCTACAT | GCTGGAATTA | TTTCCTCTGC | TTCTCTCTCA | 300 |
| CCCCACCTTG | GCCAAAGATT | TTCTAGCAAG | ATCTGAATTT | AATCCATCT | CTCTTCGCCT | 360 |
| GTGTGTCCCG | ACTAATTTGG | CAGAAGGAAT | TCTTTCTTAA | ACCTTGCCAT | TTAATTCACA | 420 |
| AATGGAAATG | TGAAGGGTCA | ATAGGTATGT | GAAGAACCTA | TTCACCCGTA | TTCACTGGGA | 480 |
| ATCAGAGAAG | TGAAAATGGA | AAAGAACACT | GAGCTATCAT | CTTAGATACA | CAAAACTGTC | 540 |
| AAACATTTGA | AGGTGGCTAA | CACCAAATGT | CAATCAGGAT | ATGAGGAAAG | TAGGAATTCT | 600 |
| TCTATACAAG | AGGACAGAAA | TCTGGCAGTG | CCAAAAGAAA | AACTACATCT | ATGATCTGCC | 660 |
| CCTCCGCAGA | TCCCATTCCT | AATACATATA | TCCCAGCGAG | TTCTGCTAAT | CTGCAGAGGA | 720 |
| TGTCTAGAAA | CGCATTCATC | ACATCAGTGT | TTATAATAAC | CAGGAGTAGG | AGGCAATCAA | 780 |
| ATGTCCTTCA | CAAGTGGAAC | TGGTAAGTTA | AAGAGACTTA | GGTTGGGTTT | CTCTAAAACC | 840 |
| AGGCCACAAG | ACAAAGATTT | GTATTCCAGT | GGCTTATTTT | GATTTAGGAG | ATGATTTAAG | 900 |
| GAATCACCAG | TGCGGGAGGT | GTAACAGTGA | ACCCAAGACA | CCTTGAGATC | AATAAAAGG | 960 |
| TGCATTGTTG | GCAGGCTGCC | TGCAAAGAAG | GGAGCATATC | CAGTAGACAC | ACCAGGAGGC | 1020 |
| AGTTTGTACA | TGCCTAAGAG | TAATCCCACC | TTAGCTGTAG | AACACAAGGA | TATTTAGTCT | 1080 |
| CCAGTTCCCA | TCATGTGGGC | TGAGTGGTGG | TCCCAGGTGC | TTTAATTTGT | AGTCCATCTG | 1140 |
| CCCAAGCACA | GGCCAAAAGA | AAGCCTTCCC | ACAGAGTCCC | GAGATCATGT | GGCAGCATGC | 1200 |
| CAGAGGTATG | TACTGGAACA | GTAGGTGCGA | AAGGCAACAA | TTACATCATG | AAAACTGCAC | 1260 |
| ATCTCACTCA | TATGTGGAAT | CTAAAGTAAT | TTAGCTCATA | GAAGTTAAGA | GTAGAATAGT | 1320 |
| TAGAGTAGTA | GAAAGTTAAG | AGTTGTTACT | GGAGAGAAAA | GAGGGTATGA | AGCTAGAAAA | 1380 |
| AAAGCTAGAA | GGAAGGATTT | TGAATGTTCT | CATGACAAAG | AGATGATAAA | TGTTTGAGGT | 1440 |
| GACAGACATG | CTAATTACCA | TGATTTGATC | TTTACACAAT | GTCTGCATGT | ATCAGAACAT | 1500 |
| CACACACTAC | CAAATAAATA | TATACAATTG | TTATGTGTCA | AAAAACATTA | TATACAATGT | 1560 |
| TTATATTTTA | TATTAATATT | AATGTAAATA | AAAATTTACA | CAAATCTTTT | CATTAAATAT | 1620 |
| GGTGTGGATA | ATTATATTAT | CTGATGATAC | CCATGCCACA | GGCTAGGAGA | AATAAAAATT | 1680 |
| TACATTAATG | TTAATGTCAA | AAAAGCAGAA | ACAAAGCCAT | ATGATACATG | TGACACTTAT | 1740 |
| ACCACATGCA | TAGAGTTATT | TCAGACACAT | TGTGTGTTAC | CTTTGGGTAG | AGAAGTGAAT | 1800 |
| GAGAGTGAGG | ATGAGAGATG | AAAAGAGGCA | GAAGAAAAA | GAGAGGCCTT | ATAGGAAGTG | 1860 |
| ATGAAAGTGT | GCCATAAACT | GAGAGTATGA | CTAAAACCTT | TCATCTTCCT | CTTCTGCCGC | 1920 |
| TTCTAAGTTA | TTGGTTCTGC | TGTTCCTTGA | CCTGTTTCAA | GCTCTCACCT | TCTATATCAC | 1980 |
| ACATGGGAAG | TCTGGCATCA | GACTTCCAGA | GAGCAAGAAC | TAGGTGAAAT | ACAAGGGCAC | 2040 |
| AGCTCTCCTA | GCCTGTGGCA | TGGGTATCAT | CAGATAATAT | AATTATCCAC | ACCATTTTTA | 2100 |
| ACGAAAAGAT | TTGCGTAAGA | GATTCACAGA | GGCAACCTGA | GGCCCTGCAA | CTACATTTCC | 2160 |
| CAGAGATCCC | TGAGGTGATC | CTAACTAGAC | TCTGGTGTCA | GGGTGATACG | GAATTCCAGT | 2220 |
| GAGATCACTT | CCCTTGCAGA | CTTTGGAAGG | GAGAGCACTT | TATTACAGAC | CTTGGAAGCA | 2280 |
| AGAGGATTGC | ATTCAGCCTA | GTTCCTGGTT | GCTGGCCAAA | GTAAGTAGAA | CTTTGTAAGT | 2340 |

-continued

```
AATTTGCAGT GTACTTTGAA AGTGGGGTAT AAATTAAAAA TAAAATCAAG TCCCCCTACT        2400

GACTGAATGG ATCCCCTCTT GTCCTAGGCG ACCCCAGAGA AACCTGGAAA ACTAAATTCC        2460

AGGCCATAAT GGAAAGGGAG GTCAGACACG CCTCATTATA CACACTCCCT TTTGGAGTTC        2520

AGGCACAACT GACCAGCATT AACATTGAAA CAGTGATCAT AAGACTGTCA AAATGGACTG        2580

TTTGTGGGAA TAAGATACCA AATTCCAATC TGACTCTGGT TTAGCATCAC ATGACAATAG        2640

CAGACCCTGA AGGAAATCAA TATATTTAAT CCCAAAATAT ATTTCTTTGA CACATATTGA        2700

ATGGTCTTGC AAACCATCTT TATGGGAATT TGCTGGTTTC TGGCTCTGCT CTGATTGAGG        2760

AGAGATAA                                                                2768
```

( 2 ) INFORMATION FOR SEQ ID NO:6:

( i ) SEQUENCE CHARACTERISTICS:
        ( A ) LENGTH: 6464 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 723..1595

( i x ) FEATURE:
        ( A ) NAME/KEY: exon
        ( B ) LOCATION: 717..1936

( i x ) FEATURE:
        ( A ) NAME/KEY: polyA_signal
        ( B ) LOCATION: 1794..1799

( i x ) FEATURE:
        ( A ) NAME/KEY: polyA_signal
        ( B ) LOCATION: 1800..1805

( x i ) SEQUENCE DESCRIPTION: SEQ ID NO:6:

```
GAATTCAGTG TCTCTCCCTG TGCACCCACT AACCCCTCTT TTTGTTTTCA CCAGGCACTT         60

ACCACAATCT AACAGACTGC ATGTTTTATC CATTTATTCA GTTTCCTATT TGTGTCCCTT        120

CAACTCCCAT TAAAATATAA TATTTTTGAG GGCAAGCAAG TACTAGAACA ATAGGAAACA        180

CATCAAGAGT ATTCTGTAAA CTATTTCTTG AATCAATCAG TGAATGAATG AATTAATCAA        240

TATATTTTTT GAGTGAGGAG CTTTGTGTTA GGTACAGCTA AATGGGAAAT CAAGTGGGTC        300

ATGTACCATG AATACCATAT ACTCTACTGT ATAATTCTCC TGCTTATATC AGAAACTGTT        360

TATAAGCCTA TTATAATTGA TACCAATTGG AATCTCTTTT TTACTCATCA CCAAGAACAC        420

CACAAACAAG TTGTTTACCA TTTGGCTCCT TATTTAATCT GGATTCCAA CTCCTCATGC         480

TTAAAGACG GAAGATACAA TAATACTTTC CTTACAGGGT TCTGAGACTA CTAAGAGAAC         540

TTATGCATGT AAAAGGGATT CATGCAGTAG AAATACTAAC AAAAGAATTA CTATGACAGA        600

TACTTATAAC CATTGTGTTT TTACGTATTT AAAATACGTT ATACCTATAA TTAGTCACAC        660

GAGGAAATCA AATGCTAAAG TATGATATGT TTTTATGTTT TGTTTTTCTT GCTTAGGGGA        720
```

```
TC ATG GAC ATT GAA GCA TAT TTT GAA AGA ATT GGC TAT AAG AAC TCT         767
   Met Asp Ile Glu Ala Tyr Phe Glu Arg Ile Gly Tyr Lys Asn Ser
   1               5                  10                  15

AGG AAC AAA TTG GAC TTG GAA ACA TTA ACT GAC ATT CTT GAG CAC CAG        815
Arg Asn Lys Leu Asp Leu Glu Thr Leu Thr Asp Ile Leu Glu His Gln
        20                  25                  30

ATC CGG GCT GTT CCC TTT GAG AAC CTT AAC ATG CAT TGT GGG CAA GCC        863
Ile Arg Ala Val Pro Phe Glu Asn Leu Asn Met His Cys Gly Gln Ala
```

|  |  |  |  |  |  |  |  |  |  |  |  |  |  |  |  |  |
|---|---|---|---|---|---|---|---|---|---|---|---|---|---|---|---|---|
| | | 35 | | | | | 40 | | | | | 45 | | | | |
| ATG | GAG | TTG | GGC | TTA | GAG | GCT | ATT | TTT | GAT | CAC | ATT | GTA | AGA | AGA | AAC | 911 |
| Met | Glu | Leu | Gly | Leu | Glu | Ala | Ile | Phe | Asp | His | Ile | Val | Arg | Arg | Asn | |
| | | 50 | | | | | 55 | | | | | 60 | | | | |
| CGG | GGT | GGG | TGG | TGT | CTC | CAG | GTC | AAT | CAA | CTT | CTG | TAC | TGG | GCT | CTG | 959 |
| Arg | Gly | Gly | Trp | Cys | Leu | Gln | Val | Asn | Gln | Leu | Leu | Tyr | Trp | Ala | Leu | |
| | | 65 | | | | | 70 | | | | | 75 | | | | |
| ACC | ACA | ATC | GGT | TTT | CAG | ACC | ACA | ATG | TTA | GGA | GGG | TAT | TTT | TAT | ATC | 1007 |
| Thr | Thr | Ile | Gly | Phe | Gln | Thr | Thr | Met | Leu | Gly | Gly | Tyr | Phe | Tyr | Ile | |
| 80 | | | | | 85 | | | | | 90 | | | | | 95 | |
| CCT | CCA | GTT | AAC | AAA | TAC | AGC | ACT | GGC | ATG | GTT | CAC | CTT | CTC | CTG | CAG | 1055 |
| Pro | Pro | Val | Asn | Lys | Tyr | Ser | Thr | Gly | Met | Val | His | Leu | Leu | Leu | Gln | |
| | | | 100 | | | | | 105 | | | | | 110 | | | |
| GTG | ACC | ATT | GAC | GGC | AGG | AAT | TAC | ATT | GTC | GAT | GCT | GGG | TCT | GGA | AGC | 1103 |
| Val | Thr | Ile | Asp | Gly | Arg | Asn | Tyr | Ile | Val | Asp | Ala | Gly | Ser | Gly | Ser | |
| | | | 115 | | | | | 120 | | | | | 125 | | | |
| TCC | TCC | CAG | ATG | TGG | CAG | CCT | CTA | GAA | TTA | ATT | TCT | GGG | AAG | GAT | CAG | 1151 |
| Ser | Ser | Gln | Met | Trp | Gln | Pro | Leu | Glu | Leu | Ile | Ser | Gly | Lys | Asp | Gln | |
| | | 130 | | | | | 135 | | | | | 140 | | | | |
| CCT | CAG | GTG | CCT | TGC | ATT | TTC | TGC | TTG | ACA | GAA | GAG | AGA | GGA | ATC | TGG | 1199 |
| Pro | Gln | Val | Pro | Cys | Ile | Phe | Cys | Leu | Thr | Glu | Glu | Arg | Gly | Ile | Trp | |
| | | 145 | | | | | 150 | | | | | 155 | | | | |
| TAC | CTG | GAC | CAA | ATC | AGG | AGA | GAG | CAG | TAT | ATT | ACA | AAC | AAA | GAA | TTT | 1247 |
| Tyr | Leu | Asp | Gln | Ile | Arg | Arg | Glu | Gln | Tyr | Ile | Thr | Asn | Lys | Glu | Phe | |
| 160 | | | | | 165 | | | | | 170 | | | | | 175 | |
| CTT | AAT | TCT | CAT | CTC | CTG | CCA | AAG | AAG | AAA | CAC | CAA | AAA | ATA | TAC | TTA | 1295 |
| Leu | Asn | Ser | His | Leu | Leu | Pro | Lys | Lys | Lys | His | Gln | Lys | Ile | Tyr | Leu | |
| | | | 180 | | | | | 185 | | | | | 190 | | | |
| TTT | ACG | CTT | GAA | CCT | CAA | ACA | ATT | GAA | GAT | TTT | GAG | TCT | ATG | AAT | ACA | 1343 |
| Phe | Thr | Leu | Glu | Pro | Gln | Thr | Ile | Glu | Asp | Phe | Glu | Ser | Met | Asn | Thr | |
| | | | | 195 | | | | | 200 | | | | | 205 | | |
| TAC | CTG | CAG | ACG | TCT | CCA | ACA | TCT | TCA | TTT | ATA | ACC | ACA | TCA | TTT | TGT | 1391 |
| Tyr | Leu | Gln | Thr | Ser | Pro | Thr | Ser | Ser | Phe | Ile | Thr | Thr | Ser | Phe | Cys | |
| | | 210 | | | | | 215 | | | | | 220 | | | | |
| TCC | TTG | CAG | ACC | CCA | GAA | GGG | GTT | TAC | TGT | TTG | GTG | GGC | TTC | ATC | CTC | 1439 |
| Ser | Leu | Gln | Thr | Pro | Glu | Gly | Val | Tyr | Cys | Leu | Val | Gly | Phe | Ile | Leu | |
| | | 225 | | | | | 230 | | | | | 235 | | | | |
| ACC | TAT | AGA | AAA | TTC | AAT | TAT | AAA | GAC | AAT | ACA | GAT | CTG | GTC | GAG | TTT | 1487 |
| Thr | Tyr | Arg | Lys | Phe | Asn | Tyr | Lys | Asp | Asn | Thr | Asp | Leu | Val | Glu | Phe | |
| 240 | | | | | 245 | | | | | 250 | | | | | 255 | |
| AAA | ACT | CTC | ACT | GAG | GAA | GAG | GTT | GAA | GAA | GTG | CTG | AAA | AAT | ATA | TTT | 1535 |
| Lys | Thr | Leu | Thr | Glu | Glu | Glu | Val | Glu | Glu | Val | Leu | Lys | Asn | Ile | Phe | |
| | | | | 260 | | | | | 265 | | | | | 270 | | |
| AAG | ATT | TCC | TTG | GGG | AGA | AAT | CTC | GTG | CCC | AAA | CCT | GGT | GAT | GGA | TCC | 1583 |
| Lys | Ile | Ser | Leu | Gly | Arg | Asn | Leu | Val | Pro | Lys | Pro | Gly | Asp | Gly | Ser | |
| | | | 275 | | | | | 280 | | | | | 285 | | | |
| CTT | ACT | ATT | TAGAATAAGG | AACAAAATAA | ACCCTTGTGT | ATGTATCACC | | | | | | | | | | 1632 |
| Leu | Thr | Ile | | | | | | | | | | | | | | |
| | | 290 | | | | | | | | | | | | | | |

| | |
|---|---|
| CAACTCACTA ATTATCAACT TATGTGCTAT CAGATATCCT CTCTACCCTC ACGTTATTTT | 1692 |
| GAAGAAAATC CTAAACATCA AATACTTTCA TCCATAAAAA TGTCAGCATT TATTAAAAAA | 1752 |
| CAATAACTTT TTAAAGAAAC ATAAGGACAC ATTTTCAAAT TAATAAAAAT AAAGGCATTT | 1812 |
| TAAGGATGGC CTGTGATTAT CTTGGGAAGC AGAGTGATTC ATGCTAGAAA ACATTTAATA | 1872 |
| TTGATTTATT GTTGAATTCA TAGTAAATTT TTACTGGTAA ATGAATAAAG AATATTGTGG | 1932 |
| AAAACTCACT GTCTCTAAAG TTTATGAAAA CATTGTTGGC TAATATATTG TGAATCAAAG | 1992 |
| TTTTTCTTTA GACGACTTAG GATATTATGG GGCTAGGCAT TTTTTCCTCA ATAGAGTCTT | 2052 |

-continued

```
CCTCTCATCC TCTTTCTTGT CTCCTAGTTA CATTCTTTTA CTTCCATCCA TACTTTGCCA     2112
CAAAAGAAGG AACATGAGCT TTATTGTGTA GATCTGATTT GAAATCCTGT GGACACGGGG     2172
TGAATTACTT TTAAAATCTG TGGCTCTGAT TCCTCAAAGA TAAAATGCAA ATAATATTTA     2232
TATAATTCAC TGCCAGATAT AAATTTTCAA ACTATTTGT TATATGGATG AATAACATCA      2292
TTAATATTGT GGTTGCTGGG CCAGCATTTG CCAAAAGTTC TCCTTCCATT TTGCTTTATT     2352
TTCCTGTAAC TTGAAATTCT GGTCCTACTG TCATCTGCCT GCTTCTTCCT TAATTAAATA     2412
TTGATAGGAT ATCAGATGTC TCGGATCTGA GAGTGTGCCT TGTGATTCAA AATCTGAATC     2472
TTTACTTATC CATAACTCAG ATTTTCTGTT TGTAAATTCC GGTATCAGGG CTATAGTTTA     2532
AACTGCAGAT TTGTTCTTAA CACTATTCTC CCTCTTCGAC TCGTGATGAC TATAATAATC     2592
TTAAGAGAAA AGCAGACATT AGAATGAATA AATATTCATT AGGAGAATAA ATTACATTGA     2652
AGCATCAGTA TTTTAGGCAG CAGTGTAATA GTTGGGAGAT ACTGGTGAGT GTAGATATCC     2712
TAGGAAGAGG TGGATAGGAG ATCTGGCCTC AGTGGGAAGG ACAAATGAAA GACATATAGC     2772
AATATTTGAG AGCTTGTCAT CTTTCTTACC TATTAGCCTT GTTCAGCTCT CCTGCTATCT     2832
TGTTGCAATG CCAGGTCACC ACTGGTGCTC CTAGGCAGAC CCAAGTTTCT CACATTCTGA     2892
GCAAGATCAC ATCACAGGAG GATGTGGTGG CAAAAACAA AAATGAAAAC AAAACAATCA      2952
AACAAAAAAC CAGATAAAAA TGTGGCTCAA GTATGAGATA CAGTTGTATC AATGAATCAA     3012
GTAAATTATA TTGCACACGA GTATCTGAAC CTAATTCAGT TGTTTGTTCT TGATTATATA     3072
TATGTACATA TGGAAAAAGC AAAAATATGT TCAGAGAGAT TCAGAAATAC ACAATTTCGC     3132
TTCCAGGTTG AAGCCTTCTG CCCTTATTAT GCAATGTTAC CTTTTCTCTA ATGAAATCTA     3192
AATGAGTGAA GAAGAATCTC GCCAATTGAT TTGCCCAGAG ATTTTAAGGT GCCTCTTAAT     3252
TGTTTGTGTT TGTCCAAACC CATGTCTCTG TTTTTGGTGG CCCCCTGGAG ACTAGGATGT     3312
GGCATATCTT GGTAGAACTC TGAGATAAGT AAGGTAGAAA CCAAACCTTC TAGACGTAAC     3372
TGGGAAGGTA GGATCTTGGA TGTATATTCC AGTTCTTCTA TTTTCAAGGT GAAGCTGAGT     3432
GTGTGTTTTT ATCTGCCACT CTCTCTGCTG AAAGCCAGGG AGATTATATG GGGCAAGTAC     3492
CCATACTGGT GTTCAGGCGG CAGCCTCTGA TCCTAGGAGA TACCTATTGA AGTAAGCCTA     3552
TGTCATATCC ACCTATTTGT TTTTTGTGGC CTAGGGACAT TCAGGAATGG AAAGCCCCAC     3612
TGATTCCCAG AGCTAGGTCA TTAAGAAGAC AGTGCCTTTG GTGGGAGCTA TATAAGTTGT     3672
GGCTCTTGGT GTGTGAACTA ACTCCTTCAA GGTAAATGAA TAGGCCTAGA TTTATTACTG     3732
GGGTGAGCTG GAAGAAGGC TCAGGAAGTG CCAAGCTGTG GCTCAGGTTA CTGGAGGGCT      3792
ACTATTTGCT CACCAATGCA AATGTATTAG AAGCAAGCTT GTCAAATAGT CATGGAAAGA     3852
ATGTGCAGGA AAATCCTTCT GGAGGGAAAA ATGGGAGCTG TGCATTCCAG AATTTTTTCT     3912
GCACTGCACC CAGAGGATGT AGCCCCTGGA AGTACTTAGA TGCCCATTGA AAACCACCTC     3972
TTTGTCCTAT AATCTAGAGA GACTCACATG TGCCTTCTTC CGTTCTTTGA GCTAGAAGGT     4032
ATTTAGGATT CAGTTAATCG TGGTTGCTAT AAAAGTTGCA GCACCTAATG TATGGCATAA     4092
ATAAATCCTT TCTGGGAAGA AACACGGAGC TGCATTTTTA GAGTTCCTTC TCCACACTCC     4152
TCCCATAGTA TGAAGTCTGT GGAAGTGCAT GCAGGCTCAT ATAACTGCCT TTTCCTGTGG     4212
CCTAGAGAGA CTTGCATACA CCTAGTCCCC TCTACCCCAG AGTTGGGAGG TTTAGGATGC     4272
AGTCCTAAGA GTGGAAAGAG TGGACAAACT CTTTTCAGGT CGGATTAATA GACCTGCAAT     4332
TATCACTGGG GTTAGGGGAG AAAGCACGGG AAGAGACAAT CTCCTTCTCA GGCTGCTAGT     4392
GGGATATTTG TCTCCTTTCT CCCCAGTGCA TGTTGGAAAC CAGGCCACCA AGTAGCCACT     4452
```

| | | | | | |
|---|---|---|---|---|---|
| GGAACAGTGT | GCCATAAACC | CATTCCGGAG | GAAGTGACAG | ACAGCTGCAT | TTTAAAGCCC | 4512 |
| CTTCTGTACA | TTGCTACTGG | GGGATAAGGC | TCCTGGAAAT | GCTATGCACC | TGTATAAAAT | 4572 |
| CACCTTTTTC | CTGTGGTCTA | GAGAGACTTG | CATATGTCTA | ATTCCCTCTA | CTTCAAGAGG | 4632 |
| TAGGAGGTTG | AGGATGTAGT | CTTAGGTGGA | AGCTGTAATA | GTGGGATGCT | CATCATGTGA | 4692 |
| ACAAACTCTA | GGAGGAATCA | GTAGACACAA | AATTATAGCT | GACTAGATTG | GGAGAGGCAG | 4752 |
| TTGTCTCATC | TAACATACAG | AAACTAACAC | AGAAAGTCAA | AGAAAATGAT | GAAACAGAGA | 4812 |
| TATATATTCC | AATTAAAAAA | CAAAATAAAT | TTCCGAAACT | GTACCCAAGT | GATGTGGAGA | 4872 |
| TATGCAATTT | ACCTGACAGG | GAATTAGAAT | AAGGTCATAA | AGATGCTCTC | TGATCAGGTG | 4932 |
| ACCAATGTAG | GAACAAAACT | GTGAATTTCA | ACAAAGAGAT | TTTTTAAAGT | TTTTAAAACA | 4992 |
| CCAGACGAAA | TTATAGAACT | GAAAATACT | CTGACTAAAA | AATCTAATAG | AGATGTTCAA | 5052 |
| CAGCAGGCTA | CATCAAACAG | AAGAAGAAT | CAGGGAACTC | AAAGAACAGG | TCATTGAAAG | 5112 |
| TTATCAAGTT | TCTGTTTCAA | GAACCAGAAA | TACCATTTGA | CCCAGCAATC | CATTACTGGG | 5172 |
| TATATACACA | AAGGAATATA | AATCATTCTG | TTCTAAAGAC | ACATACATGG | GTATGTTCAC | 5232 |
| TGCAGCACTA | TTCGCAATAG | CAAAGATGTG | GAATCAATCT | AAATGCCCAT | CAATGATACA | 5292 |
| CTGGATAAAG | AAAATGTGGT | ACACATACAC | CATGGAATAC | TATGCAGCTA | TAAGAAAGAA | 5352 |
| TGAGATCATG | TCCTTTGCAG | AAACATGGAT | GAAGCTGGAG | GCCATTATCC | TTAGCAAACC | 5412 |
| AATGCAGAAA | CAGAAAACCA | AATACCACAT | GTTCTTACTT | GTAAGTGGGA | GCTAAATGAT | 5472 |
| GAGAACACAT | GGACACATAG | AGGGGAACAA | CTCACACTGG | GGCCTACTGG | GGTGAAGAGT | 5532 |
| AGGAGGAGAG | AGAGAAGCAG | AAAAAATAAA | TAATGTGTAC | TAGGCTTACT | ACCTGCGTGA | 5592 |
| CAAAGTTAAT | CTGCAAAACA | ACCCCATGAC | ACGAGTTTAT | CTATATAACA | AACCTGCACA | 5652 |
| TGTTAGCCCC | TGAACTTAAA | ATAAAAATTA | AATTTAAAAA | ATAAGATTAA | TATCTGCATA | 5712 |
| TAAATCTTTG | TTTACAGCTT | GTTATATACT | GAATTATGTC | TGCTCCCCCA | ACATTCATAT | 5772 |
| GTTAAAGCCC | AAAGTTATTG | TGTTTGGAAA | TAGGGCTTTT | AGGAGATATT | TAAGGTTAAA | 5832 |
| TAAGGTTATA | AACGTGGAGT | CTTAATCTGA | TAGGATTGGT | GGCTTTATAA | GAAAAGAAA | 5892 |
| AGAGATTGCT | CTCTCCCCAG | TGCAGGTACC | AAGGAAAGGC | CATGTGAGAA | CATAGCAGGA | 5952 |
| AGGGCAGCCA | TCTGTAACCT | AAGGAAAGAG | ATCTGTCAAA | GGACAAAACT | ACAACAAATG | 6012 |
| TAAAGATCTC | AATTGGCTTT | ATCTGTGACT | CTGGAATCAG | GCAACACTCC | ATTTCATAAA | 6072 |
| ACAGAACTAG | TGCTCCAATG | AGCTGAGCAA | AAGGGGTTGT | TAGTTTTATA | GACAGAGAAG | 6132 |
| GACGGAAGAA | AGCAGAAATA | ACGAATGGAA | AGTAGATTGG | TCAAATTTAC | TTTCCTTTTA | 6192 |
| AGGCAGAAAA | ATAGAACAAT | AACTATTCAA | GTAATCTTAA | GGTTACTTCA | GGTTAAGGGT | 6252 |
| TAAAAACAGA | AGGAATTTTA | TCATCATGCT | TATTGAAGAT | TCAAACTGGC | CTGTTTCAGA | 6312 |
| AATTGGCTGT | TATCTCTTTC | TATCTTTTAT | TTTAAGAGGC | TTCCTCAGAT | ACCATGCTGG | 6372 |
| TGGAAGAAGG | GGAGTGCCAC | CTTTCTACGG | CCAGGTGGAC | ATAAATATCC | AAGTTCCCCA | 6432 |
| TTCAATCTCC | TTGCCATTCA | AGGCAAGGTA | CC | | | 6464 |

( 2 ) INFORMATION FOR SEQ ID NO:7:

( i ) SEQUENCE CHARACTERISTICS:
        ( A ) LENGTH: 290 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Met  Asp  Ile  Glu  Ala  Tyr  Phe  Glu  Arg  Ile  Gly  Tyr  Lys  Asn  Ser  Arg
 1              5                        10                       15

Asn  Lys  Leu  Asp  Leu  Glu  Thr  Leu  Thr  Asp  Ile  Leu  Glu  His  Gln  Ile
              20                        25                   30

Arg  Ala  Val  Pro  Phe  Glu  Asn  Leu  Asn  Met  His  Cys  Gly  Gln  Ala  Met
              35                        40                   45

Glu  Leu  Gly  Leu  Glu  Ala  Ile  Phe  Asp  His  Ile  Val  Arg  Arg  Asn  Arg
         50                        55                   60

Gly  Gly  Trp  Cys  Leu  Gln  Val  Asn  Gln  Leu  Leu  Tyr  Trp  Ala  Leu  Thr
 65                       70                        75                      80

Thr  Ile  Gly  Phe  Gln  Thr  Thr  Met  Leu  Gly  Gly  Tyr  Phe  Tyr  Ile  Pro
                   85                        90                       95

Pro  Val  Asn  Lys  Tyr  Ser  Thr  Gly  Met  Val  His  Leu  Leu  Leu  Gln  Val
             100                       105                      110

Thr  Ile  Asp  Gly  Arg  Asn  Tyr  Ile  Val  Asp  Ala  Gly  Ser  Gly  Ser  Ser
             115                       120                      125

Ser  Gln  Met  Trp  Gln  Pro  Leu  Glu  Leu  Ile  Ser  Gly  Lys  Asp  Gln  Pro
         130                       135                      140

Gln  Val  Pro  Cys  Ile  Phe  Cys  Leu  Thr  Glu  Glu  Arg  Gly  Ile  Trp  Tyr
145                      150                       155                     160

Leu  Asp  Gln  Ile  Arg  Arg  Glu  Gln  Tyr  Ile  Thr  Asn  Lys  Glu  Phe  Leu
                   165                       170                      175

Asn  Ser  His  Leu  Leu  Pro  Lys  Lys  His  Gln  Lys  Ile  Tyr  Leu  Phe
             180                       185                      190

Thr  Leu  Glu  Pro  Arg  Thr  Ile  Glu  Asp  Phe  Glu  Ser  Met  Asn  Thr  Tyr
         195                       200                      205

Leu  Gln  Thr  Ser  Pro  Thr  Ser  Ser  Phe  Ile  Thr  Thr  Ser  Phe  Cys  Ser
         210                       215                      220

Leu  Gln  Thr  Pro  Glu  Gly  Val  Tyr  Cys  Leu  Val  Gly  Phe  Ile  Leu  Thr
225                      230                       235                     240

Tyr  Arg  Lys  Phe  Asn  Tyr  Lys  Asp  Asn  Thr  Asp  Leu  Val  Glu  Phe  Lys
                   245                       250                      255

Thr  Leu  Thr  Glu  Glu  Glu  Val  Glu  Glu  Val  Leu  Lys  Asn  Ile  Phe  Lys
             260                       265                      270

Ile  Ser  Leu  Gly  Arg  Asn  Leu  Val  Pro  Lys  Pro  Gly  Asp  Gly  Ser  Leu
         275                       280                      285

Thr  Ile
290
```

( 2 ) INFORMATION FOR SEQ ID NO:8:

( i ) SEQUENCE CHARACTERISTICS:
        ( A ) LENGTH: 290 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Met  Asp  Ile  Glu  Ala  Tyr  Phe  Glu  Arg  Ile  Gly  Tyr  Lys  Asn  Ser  Arg
 1              5                        10                       15

Asn  Lys  Leu  Asp  Leu  Glu  Thr  Leu  Thr  Asp  Ile  Leu  Glu  His  Gln  Ile
              20                        25                   30

Arg  Ala  Val  Pro  Phe  Glu  Asn  Leu  Asn  Met  His  Cys  Gly  Gln  Ala  Met
              35                        40                   45

Glu  Leu  Gly  Leu  Glu  Ala  Ile  Phe  Asp  His  Ile  Val  Arg  Arg  Asn  Arg
         50                        55                   60
```

| Gly | Gly | Trp | Cys | Leu | Gln | Val | Asn | Gln | Leu | Leu | Tyr | Trp | Ala | Leu | Thr |
| 65 | | | | | 70 | | | | | 75 | | | | | 80 |

| Thr | Ile | Gly | Phe | Gln | Thr | Thr | Met | Leu | Gly | Gly | Tyr | Phe | Tyr | Ile | Pro |
| | | | | 85 | | | | | 90 | | | | | 95 | |

| Pro | Val | Asn | Lys | Tyr | Ser | Thr | Gly | Met | Val | His | Leu | Leu | Leu | Gln | Val |
| | | | 100 | | | | | 105 | | | | | 110 | | |

| Thr | Ile | Asp | Gly | Arg | Asn | Tyr | Ile | Val | Asp | Ala | Gly | Ser | Gly | Ser | Ser |
| | | 115 | | | | | 120 | | | | | 125 | | | |

| Ser | Gln | Met | Trp | Gln | Pro | Leu | Glu | Leu | Ile | Ser | Gly | Lys | Asp | Gln | Pro |
| | 130 | | | | | 135 | | | | | 140 | | | | |

| Gln | Val | Pro | Cys | Ile | Phe | Cys | Leu | Thr | Glu | Glu | Arg | Gly | Ile | Trp | Tyr |
| 145 | | | | | 150 | | | | | 155 | | | | | 160 |

| Leu | Asp | Gln | Ile | Arg | Arg | Glu | Gln | Tyr | Ile | Thr | Asn | Lys | Glu | Phe | Leu |
| | | | | 165 | | | | | 170 | | | | | 175 | |

| Asn | Ser | His | Leu | Leu | Pro | Lys | Lys | Lys | His | Gln | Lys | Ile | Tyr | Leu | Phe |
| | | | 180 | | | | | 185 | | | | | 190 | | |

| Thr | Leu | Glu | Pro | Arg | Thr | Ile | Glu | Asp | Phe | Glu | Ser | Met | Asn | Thr | Tyr |
| | | 195 | | | | | 200 | | | | | 205 | | | |

| Leu | Gln | Thr | Ser | Pro | Thr | Ser | Ser | Phe | Ile | Thr | Thr | Ser | Phe | Cys | Ser |
| 210 | | | | | 215 | | | | | 220 | | | | | |

| Leu | Gln | Thr | Pro | Glu | Gly | Val | Tyr | Cys | Leu | Val | Gly | Phe | Ile | Leu | Thr |
| 225 | | | | | 230 | | | | | 235 | | | | | 240 |

| Tyr | Arg | Lys | Phe | Asn | Tyr | Lys | Asp | Asn | Thr | Asp | Leu | Val | Glu | Phe | Lys |
| | | | | 245 | | | | | 250 | | | | | 255 | |

| Thr | Leu | Thr | Glu | Glu | Glu | Val | Glu | Glu | Val | Leu | Lys | Asn | Ile | Phe | Lys |
| | | | 260 | | | | | 265 | | | | | 270 | | |

| Ile | Ser | Leu | Gly | Arg | Asn | Leu | Val | Pro | Lys | Pro | Gly | Asp | Glu | Ser | Leu |
| | | 275 | | | | | 280 | | | | | 285 | | | |

| Thr | Ile |
| | 290 |

( 2 ) INFORMATION FOR SEQ ID NO:9:

( i ) SEQUENCE CHARACTERISTICS:
        ( A ) LENGTH: 290 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Met | Asp | Ile | Glu | Ala | Tyr | Phe | Glu | Arg | Ile | Gly | Tyr | Lys | Asn | Ser | Arg |
| 1 | | | | 5 | | | | | 10 | | | | | 15 | |

| Asn | Lys | Leu | Asp | Leu | Glu | Thr | Leu | Thr | Asp | Ile | Leu | Glu | His | Gln | Ile |
| | | | 20 | | | | | 25 | | | | | 30 | | |

| Arg | Ala | Val | Pro | Phe | Glu | Asn | Leu | Asn | Met | His | Cys | Gly | Gln | Ala | Met |
| | | 35 | | | | | 40 | | | | | 45 | | | |

| Glu | Leu | Gly | Leu | Glu | Ala | Ile | Phe | Asp | His | Ile | Val | Arg | Arg | Asn | Arg |
| | 50 | | | | | 55 | | | | | 60 | | | | |

| Gly | Gly | Trp | Cys | Leu | Gln | Val | Asn | Gln | Leu | Leu | Tyr | Trp | Ala | Leu | Thr |
| 65 | | | | | 70 | | | | | 75 | | | | | 80 |

| Thr | Ile | Gly | Phe | Gln | Thr | Thr | Met | Leu | Gly | Gly | Tyr | Phe | Tyr | Ile | Pro |
| | | | | 85 | | | | | 90 | | | | | 95 | |

| Pro | Val | Asn | Lys | Tyr | Ser | Thr | Gly | Met | Val | His | Leu | Leu | Leu | Gln | Val |
| | | | 100 | | | | | 105 | | | | | 110 | | |

| Thr | Ile | Asp | Gly | Arg | Asn | Tyr | Ile | Val | Asp | Ala | Gly | Ser | Gly | Ser | Ser |

|     |     |     | 115 |     |     |     |     | 120 |     |     |     |     | 125 |     |     |
| --- | --- | --- | --- | --- | --- | --- | --- | --- | --- | --- | --- | --- | --- | --- | --- |
| Ser | Gln | Met | Trp | Gln | Pro | Leu | Glu | Leu | Ile | Ser | Gly | Lys | Asp | Gln | Pro |
|     |     | 130 |     |     |     |     | 135 |     |     |     |     | 140 |     |     |     |
| Gln | Val | Pro | Cys | Ile | Phe | Cys | Leu | Thr | Glu | Glu | Arg | Gly | Ile | Trp | Tyr |
| 145 |     |     |     |     | 150 |     |     |     |     | 155 |     |     |     |     | 160 |
| Leu | Asp | Gln | Ile | Arg | Arg | Glu | Gln | Tyr | Ile | Thr | Asn | Lys | Glu | Phe | Leu |
|     |     |     |     | 165 |     |     |     |     | 170 |     |     |     |     | 175 |     |
| Asn | Ser | His | Leu | Leu | Pro | Lys | Lys | Lys | His | Gln | Lys | Ile | Tyr | Leu | Phe |
|     |     |     | 180 |     |     |     |     | 185 |     |     |     |     | 190 |     |     |
| Thr | Leu | Glu | Pro | Gln | Thr | Ile | Glu | Asp | Phe | Glu | Ser | Met | Asn | Thr | Tyr |
|     |     | 195 |     |     |     |     | 200 |     |     |     |     | 205 |     |     |     |
| Leu | Gln | Thr | Ser | Pro | Thr | Ser | Ser | Phe | Ile | Thr | Thr | Ser | Phe | Cys | Ser |
|     | 210 |     |     |     |     | 215 |     |     |     |     | 220 |     |     |     |     |
| Leu | Gln | Thr | Pro | Glu | Gly | Val | Tyr | Cys | Leu | Val | Gly | Phe | Ile | Leu | Thr |
| 225 |     |     |     |     | 230 |     |     |     |     | 235 |     |     |     |     | 240 |
| Tyr | Arg | Lys | Phe | Asn | Tyr | Lys | Asp | Asn | Thr | Asp | Leu | Val | Glu | Phe | Lys |
|     |     |     |     | 245 |     |     |     |     | 250 |     |     |     |     | 255 |     |
| Thr | Leu | Thr | Glu | Glu | Glu | Val | Glu | Glu | Val | Leu | Lys | Asn | Ile | Phe | Lys |
|     |     |     | 260 |     |     |     |     | 265 |     |     |     |     | 270 |     |     |
| Ile | Ser | Leu | Gly | Arg | Asn | Leu | Val | Pro | Lys | Pro | Gly | Asp | Gly | Ser | Leu |
|     |     | 275 |     |     |     |     | 280 |     |     |     |     | 285 |     |     |     |
| Thr | Ile |     |     |     |     |     |     |     |     |     |     |     |     |     |     |
|     | 290 |     |     |     |     |     |     |     |     |     |     |     |     |     |     |

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CTTAATTCTC ATCTCCTGCC                20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

TGTTGGAGAC GTCTGCAGGT                20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

ACAATACAGA TCTGGTCGAG                20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AGCATGAATC ACTCTGCTTC         20

METHODS AND KITS FOR IDENTIFYING HUMAN ARYLAMINE N-ACETYLTRANSFERASE GENES

This is a Continuation of application Ser. No. 08/038,667 filed 23 Mar. 1993, abandoned.

FIELD OF THE INVENTION

The present invention relates to polymorphic human arylamine N-acetyltransferase genes, a novel method of detecting said polymorphic genes, a novel diagnostic method of diagnosing or predicting an adverse effect or effects caused by an amino-containing aromatic substance or investigating the cause of such adverse effects, and a detection kit to be used in said detection method.

PRIOR ART

Exogenous and endogenous aromatic amino compounds are inactivated by N-acetylation mainly in the liver and arylamine N-acetyltransferase (NAT; EC 2.3.1.5) is known as an enzyme catalyzing said N-acetylation. Said enzyme is also called N-acetylating morphine.

The above-mentioned N-acetylating morphine is generally distributed in the liver. The first step toward the discovery of this enzyme was the genetic finding, obtained in a cumulative study of family histories in relation to isoniazid-induced neuropathy, that there are individuals high in the activity of said enzyme in the liver (rapid acetylators) and individuals low in said activity (slow acetylators) [Evans, D. A. P., et al., Br. Med. J., 2, 485–491 (1960); Evans, D. A. P., et al., Ann. N.Y. Acad. Sci., 123, 178–187 (1965)].

Later, a report suggested that N-acetyltransferase might be involved in the expression of toxicity of amine-containing drugs and in such diseases as bladder cancer and systemic lupus erythematosus (SLE) [Weber, W. W., Fed. Proc., 43, 2332–2337 (1984)].

The occurrence of the high and low N-acetyltransferase activity types mentioned above has been confirmed not only in humans but also in such mammals as rabbits, hamsters and mice. In humans, in particular, the incidence of an adverse effect of an amine-containing drug depends on the degree (rate) of initial stage acetylation in the liver, and those individuals in whom said acetylation proceeds slowly are called slow acetylators and those in whom the acetylation proceeds rapidly are rapid acetylators. So far these two types of acetylator have been discriminated by loading individuals with an amine-containing drug and determining the half-life of said drug [R. A. Knight, et al., Trans. Cong. Chemother. Tuberculosis, 18, 52–58 (1959); D. A. P. Evans, et al., Br. Med. J., 2, 485–491 (1960)].

Meanwhile, animal models have been constructed for both acetylator types and the relationship between drug metabolism and adverse effects or between carcino-genesis and N-acetyltransferase has been studied in said models [R. H. Tannen, et al., J. Pharmacol. Exp. Ther., 213, 480–484 (1980); D. W. Hein, et al., J. Pharmacol. Exp. Ther., 223, 40–44 (1982); D. W. Hein, et al., J. Pharmacol. Exp. Ther., 233, 584–587 (1985)].

At present, the drugs or other substances for which a correlation between the above-mentioned slow acetylator and rate of metabolism has been suggested include sulfamethazine, other sulfanoids, isoniazid, procainamide, hydrallazine, phenelzine, caffeine, nitrazepam, carcinogenic benzidine, 2-aminofluorenece and β-naphthylamine, among others [D. A. P. Evans, et al., J. Lab. Clin. Med., 63, 394–402 (1964); J. W. Jenne, et al., J. Clin. Invest., 44, 1992–2002 (1965); J. W. Jenne, et al., Am. Rev. Respir. Dis., 84, 371–378 (1961); J. H. Peters, et al., Life Sci., 4, 99–107 (1965); Weber, W. W., The Acetylator Genes and Drug Response, Oxford University Press, New York (1987)].

Recently, the occurrence of an autosomal recessive gene leading to the above-mentioned two acetylator phenotypes was demonstrated in humans, rabbits and other mammals [Weber, W. W. and Hein, D. W., Pharmacol. Rev., 37, 25–79 (1985)] and it was also established that there is monomorphic N-acetyltransferase in the liver in addition to the polymorphic type and that said N-acetyltransferase is commonly found in all people but shows some individual variations as compared with the polymorphic one [Weber, W. W. and Hein, D. W., Pharmacol. Rev., 37, 25–79 (1985)].

As for the gene for arylamine N-acetyltransferase (hereinafter referred to as "NAT" for short), O. A. Meyer et al. [Blum, M., et al., Nucleic Acids Res., 17, 3589 (1989)] isolated cDNA from mRNA of the liver of a rabbit showing the rapid acetylator phenotype in vitro using a oligonucleotide coding for a partial amino acid sequence of purified rabbit liver NAT [Andres, H. H., et al., Mol. Pharmacol., 31, 446–456 (1987)] and an NAT-specific antiserum, and D. M. Grant et al. prepared a cDNA probe specific for said rabbit liver NAT gene and successfully isolated a human NAT gene using said probe [D. M. Grant, et al., Nucleic Acids Res., 17, 3978 (1989)]. Reportedly, the coding or coding region of said human NAT gene comprises 1,981 bp (base pairs) with 82% and 61% homologies to the rabbit and chicken liver NAT genes, respectively. The cDNA coding region for chicken liver NAT has been isolated by Ohsako et al. [Ohsako, S., et al., J. Biol. Chem., 263, 7534–7538 (1988)].

The present inventors, too, made intensive investigations concerning human NAT genes. They prepared poly(A)$^+$ RNA from human livers obtained at autopsy, constructed human λgt10 cDNA libraries, isolated 24 positive clones from among $3 \times 10^6$ recombinant phages using the above-mentioned rabbit NAT cDNA as a probe, and successfully obtained three types of cDNA (designated as D-14, O-7 and D-24, respectively). With these types of NAT gene, they obtained the following findings [Ohsako, S. and Deguchi, T., J. Biol. Chem., 265 (8), 4630–4634 (1990)].

(1) The human liver NAT gene cDNAs D-14, O-7 and D-24 are 1,210 bp, 1,276 bp and 1,319 bp long, respectively; D-14 is 66 bases shorter than O-7 at the 5'-noncoding region.

(2) All the three cDNAs code for 290 amino acids.

(3) O-7 and D-14 differ from each other at two points (282nd and 857th bases); the mutation at position 282 is a silent mutation while the result of mutation at position 857 is glycine in O-7 and glutamic acid in D-14.

(4) O-7 and D-14 are 80% homologus to D-24 on the amino acid level.

(5) The calculated molecular weights are 33,542 for O-7, 33,787 for D-14 and 33,614 for D-24.

(6) In all the three types of cDNA, the 3'-noncoding region ends in an EcoRI site.

(7) In view of the NAT activity levels obtained upon expression of the genes in CHO cells, O-7 and D-14 are polymorphic NAT genes while D-24 is a monomorphic NAT gene.

(8) The NAT activity produced by D-14 is 9–17% of the activity produced by O-7 and these activities are different. O-7 can be considered to be of the rapid type and D-14 of the slow type and this difference can be detected at the BamHI site. This activity difference is presumably due to the difference in a single amino acid among the amino acids constituting the enzyme proteins.

Further, to elucidate the polymorphism involved in the above genes, the present inventors investigated the acetylator polymorphism among Japanese people by studying the differences in restriction endonuclease cleavage pattern in Southern blotting through an isoniazid loading test and, as a result, detected and confirmed three types of NAT gene at the EcoRI-KDnI recognition site including a 3'-noncoding region. The first type is a type 1 gene containing a 5.3 kb DNA fragment resulting from KpnI digestion and having a BamHI site; the second type is a type 2 gene containing a 5.3 kb DNA fragment resulting from Kpn. I digestion and having no such restriction site, and the third type is a type 3 gene containing a 4.9 kb DNA fragment resulting from KpnI digestion and having a BamHI site. Based on the combinations of these genes, five polymorphic types could be distinguished, and the acetylator polymorphism could be elucidated based on the results of the isoniazid test mentioned above. As a result, 29 healthy Japanese subjects tested could be divided into three phenotypes, namely rapid acetylators (10 subjects), slow acetylators (3 subjects) and intermediate acetylators (16 subjects). Thus, it was found that the above-mentioned rapid acetylators are type 1 gene homozygotes, the intermediate acetylators are heterozygotes of the type 1 and type 2 genes or of the type 1 and type 3 genes and the slow acetylators are heterozygotes of the type 2 and type 3 genes, or type 3 gene homozygotes. These results indicate that the type 1 gene is associated with high NAT activity and the type 2 and type 3 genes lead to low NAT activity [Deguchi, T., et al., J. Biol. Chem., 265 (22), 12757–12760 (1990)].

As mentioned above, the method of detecting NAT gene DNA polymorphism as previously proposed by the present inventors comprises cleaving the genomic DNA with a restriction endonuclease or endonucleases, performing Southern hybridization with a specific sequence as a probe, and separating and detecting restriction fragments of that region of the genome which contains said sequence, according to the lengths of the fragments. Thus, said method is an RFLP (restriction fragment length of polymorphism) analysis method which utilizes the occurrence of polymorphism at the restriction site(s) or of insertion or loss of a DNA in the fragments and detects genetic polymorphism by the changes in motility of related bands. However, this method is to detect the type 3 gene by polymorphism at the KpnI site in the noncoding region, although the type 2 gene can be detected by polymorphism at the BamHI site. Hence, said method cannot be said to be a direct method for detecting sites possibly related to enzyme activity. A more direct method for active site detection is desired in the art.

As other methods of detecting genetic polymorphism, there are known, for example, the method comprising detecting one-base substitution by utilizing the fact that DNA rendered partially single-stranded shows substantially zero motility in modified gradient gel electrophoresis and that the mismatched portion of DNA tends to become single-stranded rapidly [Meyers, R. M., et al., Nature, 313, 495–498 (1985)] and the methods which use ligase, RNase, etc. However, these methods are complicated and are disadvantageous in dealing with large amounts of DNA simultaneously. Although the development of the PCR (polymerase chain reaction) method [Science, 239, 487–491 (1988)] has caused development of a technique for amplifying small amounts of DNA with efficiency and within a short time (cf. Japanese Patent Publication (Kokai) No. 62-214355), research and development works are still required in search of an analytical method of such kind which is simple and easy and can be mechanized.

Accordingly, it is an object of the invention to develop a mechanizable method, earnestly desired in the art, of detecting the NAT activity site more directly in a simple and easy manner using DNA samples in small amounts.

The present inventors made further intensive investigations to accomplish the above object and, as a result, found that only using the base sequence information concerning the coding region of NAT genes (genotypes 1 and 2) as reported previously be the present inventors, does not allow any detection method which utilizes the NAT activity site to achieve the above object. They, however, could newly identify the base sequences of the noncoding and coding regions of a type 3 NAT gene. They found that, using said base sequences, the polymorphic DNAs can be typed based newly on the combinations of restriction sites respectively contained in the NAT genes type 1 to 3 and that said polymorphic genes can thus be detected with efficiency and in a simple and rapid manner directly utilizing the coding region of each NAT gene DNA by using the restriction endonucleases BamHI and TaqI and the PCR-RFLP method. The present inventors further confirmed the occurrence of a novel fourth type of NAT gene by analysis and found that when this type 4 gene is utilized, more polymorphic NAT genes can be detected. The above findings have now led to completion of the present invention.

SUMMARY OF THE INVENTION

The invention thus provides a type 1 human NAT gene which contains a base sequence coding for the amino acid sequence of SEQ ID NO:7, more particularly a type 1 human NAT gene which contains the 5'-noncoding region base sequence of SEQ ID NO:1 and the coding region segment-containing base sequence of SEQ ID NO:2; a type 2 human NAT gene which contains a base sequence coding for the amino acid sequence of SEQ ID NO:8, more particularly a type 2 human NAT gene which contains the 5'-noncoding region base sequence of SEQ ID NO:3 and the coding region segment-containing base sequence of SEQ ID NO:4; and a type 3 human NAT gene which contains a base sequence coding for the amino acid sequence of SEQ ID NO:9, more particularly a type 3 human NAT gene which contains the 5'-noncoding region base sequence of SEQ ID NO:5 and the coding region segment-containing base sequence of SEQ ID NO:6.

The invention also provides a base sequence containing the type 3 human NAT gene coding region segment of SEQ ID NO:6.

The invention further provides a method of detecting the polymorphic human NAT gene which comprises detecting any of the above-mentioned type 1 to 3 human NAT genes by RFLP analysis, and a method of diagnosing an adverse effect or effects to be caused by an amino-containing aromatic substance which comprises detecting a polymorphic human NAT gene according to said detection method using a human body fluid or hair as a sample and thereby diagnosing, predicting or investigating said adverse effect or effects.

In the present specification, amino acid sequences and base sequences are represented by those abbreviations or symbols that are recommended by the IUPAC-IUB Commission on Biochemical Nomenclature or conventionally used in the art.

The NAT genes of the present invention are detailedly described in the following. In using genetic engineering techniques, it is a general practice to extract and purify the desired protein and determine the amino acid sequence of a part of said protein or to search for a cDNA for the protein in question and determine the DNAs using said cDNA as a probe. Therefore, in the present specification, the sequence determination of NAT cDNAs is first described and the extraction, screening and sequencing of genomic DNAs for NAT are then described.

The genes of the invention each can be obtained by extracting total human RNA, separating and purifying mRNA from said RNA, transcribing the mRNA to cDNA to construct a cDNA library, selecting the desired cDNA from among said library, introducing said cDNA into host cells for transformation thereof and cultivating the cells.

The cells from which the total RNA is to be separated may be liver cells obtained from human livers at biopsy, peripheral leukocyte cells, cultured cells derived from these, and the like. They can be prepared, for example by the method of Hermann et al. [Hermann, B. G. and Frischauf, A. M., Methods Enzymol., 152, 180–183 (1987)]. The cells obtained in the above manner can be grown in a conventional medium, for example RPMI-1640 medium, CEM medium, CMRL-10 medium, DM-160 medium, Dulbecco's modification of Eagle's minimum essential medium (MEM), Fischer medium, F-10 medium, or any of these media supplemented with a serum such as fetal calf serum (FCS) or a serum component such as albumin. The amount of cells relative to the above medium is not critical but is generally and recommendably about $1 \times 10^4$ to $10^{10}$ cells/ml. The cultivation can be carried out in the conventional manner, for example in the manner of cultivation under carbon dioxide gas, at a temperature of about 30° to 40° C., preferably around 37° C., for a period of 5 to 17 days, preferably about 8 to 11 days.

The total RNA extraction from the cultured cells or tissue obtained in the above manner is recommendably carried out at that time when the production and accumulation of the desired human NAT in the culture supernatant is maximal. The extraction procedure can be conducted by such a conventional method as the guanidine thiocyanate-cesium chloride density gradient centrifugation method (T. Maniatis, et al., Molecular Cloning, page 194, Cold Spring Harbor Laboratory, 1982). In said procedure, the above cells are partly or completely disrupted and solubilized by the use of a guanidine thiocyanate mixed solution or an appropriate detergent such as SDS, NP-40, Triton X-100 or deoxycholic acid or with a homogenizer or by some physical method such as the freeze-thaw method. The chromosomal DNA is sheared to some extent using a Polytron or like mixer or a syringe, or by pipetting. A nucleic acid fraction is then separated from proteins. For this procedure, the cesium chloride isodensity method using ultracentrifugation at about 100,000×g [Chirgwin, J. M. et al., Biochemistry, 18, 5294 (1979)] or the phenol-chloroform extraction method is generally employed. To prevent the degradation of RNA induced by RNase, the above method or procedure can be carried out in the presence of an RNase inhibitor, such as heparin, polyvinyl sulfate, diethyl pyrocarbonate, vanadium complex, bentonite or macaloid, as added. The NAT protein contained in the protein fraction separated from the nucleic acid fraction by the above procedure can be isolated by conventional methods for separating proteins, for example by a chromatographic procedure.

The isolation and purification of mRNA from the RNA obtained by the above procedure can be effected by an adsorption column method or batchwise method using, for example, oligo-dT-cellulose (Collaborative Research Inc.), poly-U-Sepharose (Pharmacia), Sepharose 2B (Pharmacia) or the like.

The purification of the desired mRNA from the thus-obtained mRNA and the concentration and identification thereof can be effected by fractionating the mRNA obtained in the above manner by sucrose density gradient centrifugation, for instance, subjecting each fraction to a process of translation into a protein or proteins in a protein translation system, for example in oocytes of Xenopus laevis or a rabbit reticulocyte lysate or in a cell-free system such as wheat germ, and examining the activity of the protein. The presence of the desired mRNA can thus be confirmed. The desired mRNA can also be identified by using, in lieu of the above activity determination method, an immunologic method using an antibody to NAT.

The thus-obtained purified mRNA, which is usually unstable, is reversely transcribed to give the corresponding, stable complementary DNA (cDNA), which is then inserted into a replicon derived from a microorganism for the amplification of the desired gene. Generally, in vitro transcription of the mRNA to the cDNA, i.e. synthesis of the cDNA, can be realized by first preparing poly(A)$^+$ RNA using oligo(dT)-cellulose or the like and then following the method of Gubler and Hoffman [Gubler, U. and Hoffman, B., Gene, 25, 263–268 (1983)], as follows.

Thus, using oligo(dT) as a primer (which may be either free oligo dT or oligo dT already joined to a vector primer) and the mRNA as a template, a single-stranded DNA complementary to the mRNA is synthesized in the presence of dNTPs (dATP, dGTP, dCTP and dTTP) and a reverse transcriptase. The next step differs as follows depending on whether oligo dT or an oligo dT-tailed vector primer is used.

In the former case, the mRNA used as template is removed by decomposition by alkaline hydrolysis or the like, and a double-stranded DNA is synthesized using the single-stranded DNA as a template in the presence of a reverse transcriptase or DNA polymerase. Then, both ends of the double-stranded DNA are treated with exonuclease to render them blunt-ended, a suitable linker DNA or a combination of bases amenable to annealing is attached to each end, and the resulting DNA is inserted into a suitable vector. For this purpose, various known methods, for example the method of Gubler and Hoffman, can be used depending on the vector employed. The cDNA synthesis mentioned above may be carried out using a commercial cDNA synthesizing kit. The vector to be used is not limited to any particular species but may be selected, depending on the host, from among phage vectors, such as λgt phage vectors, and plasmid vectors, which may be used either singly or in combination. As typical examples of the phage vector, there may be mentioned λgt10, λgt11, etc. When λgt10 or λgt11 is used, the method of Young et al. [Young, R. A., et al., DNA Cloning, 1, 49 (1985) may be followed.

In the latter case, the mRNA used as template as such, an opened plasmid provided with the same linker as mentioned above and a linker DNA (frequently used as such is a DNA fragment containing a region autonomously replicable in animal cells and a transcriptional promoter region for mRNA) are annealed into a circular form and then the mRNA is replaced by the corresponding DNA strand in the presence of dNTPs and of RNase H and DNA polymerase I, whereby a complete plasmid DNA can be constructed.

The DNA thus obtained is introduced into a host to the vector for transformation of said host. A typical example of the host is *Escherichia coli* but the host is not limited to this species. Thus, *Bacillus subtilis* and *Saccharomyces cerevisiae*, for instance, may also be used.

For the introduction of the above-mentioned DNA into a host microorganism for transformation thereof, any of various methods in common use can be employed. For instance, a phage is used as the vector, mere infection of host cells can result in efficient integration of the DNA into the host. When a plasmid is used, cells in the logarithmic growth phase are collected and treated with $CaCl_2$ to render them ready for spontaneous uptake of DNA. This method for plasmid uptake is advantageous. Each of the above methods may be practiced in the presence of $MgCl_2$ or RbCl, as is generally known to achieve an improved transformation efficiency. The host cells may be converted to spheroplasts or protoplasts prior to transformation. These modifications are detailedly described by Gubler and Hoffman in the above-cited report [Gubler, U. and Hoffman, B., Gene, 25, 263–268 (1983)].

The screening of the desired gene from among the thus-obtained human cDNA library can be performed by any of conventional methods or a combination thereof, for example the method comprising using an NAT-specific antibody against the protein produced by the cDNA and selecting the corresponding cDNA clone by Western blotting, the Southern blotting method which uses a probe capable of selectively binding to the desired cDNA sequence, the Northern blotting method, the plaque hybridization method, or the colony hybridization method. The probe to be used here is generally a DNA sequence chemically synthesized based on the information concerning the desired DNA or RNA sequence or the amino acid sequence encoded thereby but a DNA or RNA prepared from a natural source may also be used. Since the human NAT genes show particularly high homology to the rabbit and chicken NAT genes, a labeled modification of the corresponding component cDNA of rabbits, for example, or of a part thereof may be used as the above probe. Furthermore, a labeled modification of the known human NAT O-7 cDNA or D-14 cDNA or of a part thereof may be used as said probe.

The NAT genes of the present invention can be obtained by extracting the genomic DNA for human NAT, purifying the same and integrating the same into an appropriate vector, constructing a genomic DNA library by in vitro packaging, for instance, screening out the desired genomic DNA from said library by hybridization using a human NAT cDNA as a probe, and isolating the desired clone.

The genomic DNA for human NAT to be used in the above process can be separated in the same manner as in the total RNA separation using, as a source, liver tissues obtainable from humans at autopsy, liver cells obtainable from human liver tissues at biopsy, peripheral leukocyte cells, or cultured cells derived therefrom. The source cells mentioned above can be cultivated by a conventional method.

For genomic DNA extraction from the above-mentioned source tissue, the tissue is disrupted in an appropriate buffer solution, such as Tris-hydrochloride buffer supplemented with NaCl, EDTA, etc., with ice cooling, and then solubilized using an appropriate detergent such as SDS, NP-40 or the like, proteins are digested using a proteolytic enzyme such as proteinase K, nucleic acids are extracted by following the phenol-chloroform extraction procedure, RNA is digested using ribonuclease, phenol-chloroform extraction is again conducted, and DNA is concentrated using ethanol. The desired DNA can thus be obtained. When the DNA source contains large amounts of cytoplasm and intercellular substances of liver etc., the nucleus should preferably be subjected to centrifugation, for example by the sucrose density gradient method. When cultured cells are used as the source, they are suspended in an appropriate buffer solution, as in the case of tissue, and subjected to centrifugation to give a pellet of cells and, thereafter, the desired DNA can be extracted under ice cooling in the same manner as in the case of tissue mentioned above. The above-mentioned DNA extraction and the construction of the library mentioned below are detailedly described in Haruo Ozeki et al.: "Bunshi Idenshigaku Jikkenho (Experiments in Molecular Genetics)", pages 94–110, Kyoritsu Shuppan, 1983, to which reference may be made.

A genomic DNA library can be constructed by the Southern hybridization method, for instance, using the DNA obtained above. The phage vector and restriction enzyme or enzymes to be used on that occasion can suitably be selected based on the information at the time of cDNA preparation. Thus, for instance, EMBL3, EMBL4, λFIXII, Charon 4A, λgt10, λgt11 and the like can be used as the phage vector, and pWE15, pWE16, Charomid 9–20 and the like vectors as cosmid vectors. These vectors are commercially available and can be readily obtained. Usable as the restriction enzymes are, for example, EcoRI, BamHI, Sau3AI, AluI, HaeIII, etc.

The genomic DNA for recombination is partially digested by restriction endonuclease digestion to a length allowing insertion thereof into the phage DNA employed, followed by fractionation. Said fractionation can be carried out by recovering from agarose gel electrophoresis or by sucrose density gradient centrifugation, for instance. The phage vector is subjected to restriction enzyme digestion and fractionation in the same manner. The phage vector DNAs and said desired DNA fragment are subjected to ligation using T4 DNA ligase, followed by in vitro packaging, whereby the desired genomic DNA library can be constructed. Said packaging can be performed using such a commercially available kit as Gigapack II Plus, Gigapack Gold or Gigapack XL (each obtainable from Stratagene).

The desired DNA can be detected from among the genomic DNA library, for example in the following manner. Thus, a labeled probe is first prepared from the cDNA, a part of the gene DNA, a synthetic oligonucleotide or the like by the nick translation method or by using a random primed method. Said probe labeling can be performed, for example by using a multiprime DNA labeling system (Amersham) which uses the multiprime DNA labeling method [Feinberg, A. P. et al., Anal. Biochem., 137, 266–267 (1984)]. The desired DNA can be screened out using the above labeled probe according to the plaque hybridization method developed by Benton and Davis [Benton, W. and Davis, R., Science, 196, 383–394 (1977)].

For searching in the above NAT genomic DNA library, a $^{32}P$-labeled probe derived from the 311-base-pair DNA fragment at the BamHI-EcoRI site in the coding region of the type 1 NAT gene (O-7) or the whole cDNA (O-7) can be used.

To identify all recombinant-containing gene clones following the above searching, further screening is performed with positive clones utilizing cDNAs in the 5'- and 3'-terminal regions thereof. The NAT gene-containing clones obtained can be subcloned in an appropriate plasmid such as pUC18 following cleavage with an appropriate restriction enzyme or enzymes in the conventional manner, as in general cDNA cloning.

The base sequence of each NAT gene of the invention can be determined by the dideoxy method using a T7 Sequencing™ kit (Pharmacia), for instance. When necessary, sequence primers can be synthesized using Gene Assembler Plus (Pharmacia LKB Biotechnology) or the like.

The various procedures employable in the above processes, for example chemical synthesis of certain DNAs, enzymatic treatment for the purpose of DNA cleavage, paring, addition or joining, DNA isolation, purification, replication and selection, can be carried out in the conventional manner.

For constructing the above-mentioned genomic DNA library, it is also possible to prepare giant DNAs by pulse field gel electrophoresis, for instance, to use a yeast artificial chromosome (YAC) or, further, to excise a particular chromosome portion from a sample chromosome and use the same for direct cloning by the PCR (polymerase chain reaction) method [Saiki, R. K., et al., Science, 230, 1350–1354 (1985)]. The NAT genes can be analyzed also by selecting and preparing an appropriate primer, as previously reported by the present inventors, and performing the PCR method with the DNA extracted as mentioned above.

The NAT genes of the invention can each be cloned into various plasmids in a conventional method. This cloning can be effected, for example by inserting a fragment containing any of the genes of the invention as obtained by cleavage with EcoRI followed by purification into a cloning vector, such as pUC18 or pUC19, cleaved in the same manner with EcoRI, at the cleavage site, whereby the desired recombinant vector can be obtained. For introducing said recombinant vector into a host and amplifying and separating the recombinant vector, the various methods mentioned above can be employed.

Among the procedures to be employed in the above-mentioned processes, the DNA isolation and purification procedure, for instance, can be carried out in the manner of agarose gel electrophoresis, among others. The DNA sequence of each of the genes of the invention can be determined, for example by the dideoxy method [Sanger, F., et al., Proc. Natl. Acad. Sci. U.S.A., 74, 5463–5467 (1977)] or the Maxam-Gilbert method [Maxam, A. M. and Gilbert, W., Methods in Enzymology, 65, 499–560 (1980)]. The above-mentioned DNA base sequence can also be determined readily by using a commercially available sequencing kit or the like. For amplifying a specific region of DNA, the PCR method [Saiki, R. K., et al., Science, 230, 1350–1354 (1985)] can be used in accordance with the method of Kawasaki and Wang [Kawasaki and Wang, PCR Technology, H. A. Erlich, ed., Stockton Press, New York, pages 89–98 (1989)]. Pulse field gel electrophoresis is a relatively new experimental technique the prototype of which was published by Schwarts et al. in 1982 and, in recent years, it has become a standard method of analyzing giant DNAs and is in frequent use in the fields of molecular genetics, molecular biology and the like. This technique can be used as a method of analyzing the genes of the present invention.

As a method of selecting the desired genes, the technique of Southern hybridization [Southern, E. M., J. Mol. Biol., 98, 503–517 (1975)] or dot hybridization (ditto) can also be used. In said method, DNA fragments resulting from restriction endonuclease cleavage are fractionated by agarose gel electrophoresis and transferred from the gel to a nitrocellulose or nylon filter, a probe prepared by labeling a DNA corresponding to the desired gene is hybridized with DNA fragments having a complementary base sequence on the filter to give hybrids, and the hybrid-forming DNA fragments are detected by autoradiography, for instance.

The base sequences of the thus-obtained three types (types 1 through 3) of NAT gene of the present invention and the corresponding amino acid sequences are as follows.

The type 1 NAT gene comprises the 5'-noncoding region base sequence (2768 bp) of SEQ ID NO:1 and the coding region segment-containing base sequence (6464 bp) of SEQ ID NO:2 as joined together via a base sequence of about 6.4 kb. The amino acid sequence corresponding to the coding region of said type 1 gene consists of the 290 amino acids of SEQ ID NO:7.

The type 2 NAT gene comprises the 5'-noncoding region base sequence (2768 bp) of SEQ ID NO:3 and the coding region segment-containing base sequence (6464 bp) of SEQ ID NO:4 as joined together via a base sequence of about 6.4 kb. The amino acid sequence corresponding to the coding region of said type 2 gene consists of the 290 amino acids of SEQ ID NO:8.

The type 3 NAT gene comprises the 5'-noncoding region base sequence (2768 bp) of SEQ ID NO:5 and the coding region segment-containing base sequence (6464 bp) of SEQ ID NO:6 as joined together via a base sequence of about 6.4 kb. The amino acid sequence corresponding to the coding region, which comprises 873 bases, of said type 3 gene consists of the 290 amino acids of SEQ ID NO:9.

In the 9232-base region sequenced as mentioned above, the type 1 NAT gene were found cleavable with the restriction enzyme BamHI at three sites, with KpnI at two sites and with TaqI at four sites. In the sequences of the type 2 and type 3 genes, 13 and 23 point mutations were found, respectively. In the type 2 gene, one of the two point mutations in the coding exon, which is close to the C terminus, is a point mutation from G to A, replacing the amino acid glycine by glutamine, with loss of a BamHI site. The other mutation in the coding region is a silent mutation from C to T. In the type 3 gene, a point mutation from T to G was found at 3982nd base downstream from the second exon, creating a new KpnI site. Another KpnI site was found at 542nd base downstream from said novel KpnI site in all the type 1, type 2 and type 3 genes. The occurrence of these two KpnI sites was confirmed by a different fragment length found in the KpnI digest. While the type 1 and type 2 genes contain a fragment of about 5.3 kb, the type 3 gene contains a 4.7 kb fragment. In the coding region of the type 3 gene, there are two point mutations, the mutation from G to A replacing arginine by glutamine, with loss of a TaqI site, and the other mutation from C to T being located at the same position as in the type 2 gene, without any amino acid substitution, however.

The results obtained by further screening using the whole cDNA as a probe confirmed the presence of a novel type 4 NAT gene different from the above-mentioned genotypes 1, 2 and 3. In said type 4 gene, there are three point mutations in the coding region thereof. One is the mutation from the 1063rd base T in the type 1 NAT gene of the present invention to C, causing the corresponding amino acid substitution of isoleucine by threonine. The second mutation is from the 1203rd base C in the type 1 NAT gene to T, without any amino acid substitution. The third mutation is from the 1525th base A in the type 1 NAT gene to G, replacing lysine by arginine. The length from the BamHI site in the first exon of said type 4 to the KpnI site occurring downstream from the second exon was confirmed to be not less than 15 kb.

When all or part of the genes of the present invention are used, novel other polymorphic NAT genes may be isolated and purified. The genes of the invention can be amplified and detected by the above PCR method and, therefore, part of the genes of the invention can be used efficiently as primers for gene amplification. Thus the present invention also provides the NAT genes and partial fragments thereof as DNA probes or primers for PCR.

Furthermore, the NAT genes of the invention can be used in producing and purifying NATs readily and in large amounts by utilizing the so-far known general recombinant DNA technology [cf. e.g. Science, 224, 1431 (1984); Biochem. Biophys. Res. Commun., 130, 692 (1985); Proc. Natl. Acad. Sci., U.S.A., 80, 5990 (1983); EP Laid-Open Specification No. 187991]. More specifically, said NAT production by genetic engineering can be performed, for example, by the method comprising causing expression of the type 3 NAT gene of the invention in appropriate animal cells such as CHO (Chinese hamster ovary) cells, and this can be carried out by the method previously reported by the present inventors [Ohsako, S. and Deguchi, T., J. Biol. Chem., 265 (8), 4630–4634 (1990)].

The NAT proteins obtainable by the above-mentioned recombinant DNA technology can be used also in determining NAT activity in various amine-containing drugs or foods. Said proteins can further be used in producing antibodies specific to NAT proteins. In this antibody production, genetically engineered components may be used as antigens and the antibodies include polyclonal antibodies as well as monoclonal antibodies. Epitope-specific antibodies can also be obtained from polyclonal antibodies to NAT protein complexes by the method of Weinberger et al. [Science, 228, 740–742 (1985)], for instance. The thus-obtained antibodies can be used also in purifying, assaying or identifying NAT proteins or identifying a possibly occurring NAT gene or genes other than the type 1, type 2, type 3 and type 4 NAT genes.

While the above-mentioned NAT proteins basically have the specific amino acid sequences shown under SEQ ID NO: 7, SEQ ID NO: 8 and SEQ ID NO: 9, the recombinant DNA technology can give mutant polypeptides derived therefrom, for example those polypeptides in which the N-terminal methionine of the respective amino acid sequences has been deleted, and those having an additional amino acid sequence, for example the whole or part of the signal peptide sequence for the NAT genes, at the N terminus, and those in which part of these amino acid sequences is missing. These polypeptides can be produced by post coding modification or by using mutated genes. Said mutated genes can be synthesized, for example by site-specific mutagenesis of the natural-type genes or by chemical synthesis, for example by the phosphotriester method. Therefore, it is to be noted that the NAT genes of the invention include such various mutant genes obtainable in the conventional manner as well.

In the following, the method of detecting polymorphic NAT DNAs by using the genes of the invention is described in detail. For said detection method, the Southern hybridization method or dot hybridization method, for instance, can be employed. As a specific example thereof, the method previously reported by the present inventors [Deguchi, T., et al., J. Biol. Chem., 265 (22), 12757–12760 (1990)] can be utilized effectively. More specifically, this NAT DNA polymorphism detection or human acetylator phenotype determination using the genes of the invention is carried out by the PCR-RFLP (PCR-restriction fragment polymorphism analysis) method, the PCR-single strand higher-order structure polymorpohism analysis method [Orita, M. et al., Proc. Natl. Acad. Sci., U.S.A., 86, 2766 (1989)], the PCR-SSO (PCR-specific sequence oligonucleotide) method, or the allele specific oligomer (ASO) method [Saiki, R., et al., Nature, 324, 163–166 (1986)] based on the PCR-SSO and dot hybridization techniques.

When the sample is human blood or hair, the above PCR-RFLP method is carried out as follows. In the case of a human blood sample, for instance, nucleated cells are collected from said human blood by an usual method and, after phenol treatment, DNA is extracted. First, a 5'-primer and a 3'-primer are synthesized so that the DNA fragment to be amplified by PCR has a length of 100 bp to 500 bp including the intended restriction site. Then, the extracted DNA sample, a PCR reaction buffer, a mixed solution of the four deoxynucleotides, the synthetic 5'-primer and 3'-primer, and Taq polymerase are mixed up, the mixture is distributed, mineral oil is layered, and the PCR is carried out. Said PCR is performed by subjecting the above reaction mixture to one cycle of heating at 94° C. for 3 minutes, at 54° C. for 2 minutes and then at 72° C. for 3 minutes, then to 29 cycles consist of heating at 94° C. for 1 minute, at 54° C. for 2 minutes and at 72° C. for 3 minutes, and finally to heating at 72° C. for 10 minutes, to attain DNA amplification.

Then, the mineral oil is removed from the above reaction mixture, and the mixture is electrophoresed on a 3% agarose gel. Band identification is based on staining with the above-mentioned ethidium bromide.

Further, a restriction endonuclease or endonucleases capable of recognizing the intended restriction site or sites are added to the amplification reaction mixture, then digestion is conducted overnight at 37° C., and 3% agarose gel electrophoresis is performed in the same manner as above, followed by band identification by ethidium bromide staining.

The genotype of the chromosomal DNA can be determined based on the band pattern obtained in the above manner. Based on said pattern, the following phenotypes can be distinguished: rapid type comprising genotype 1 and genotype 1, intermediate type comprising genotype 1 and genotype 2, intermediate type comprising genotype 1 and genotype 3, slow type comprising genotype 2 and genotype 2, slow type comprising genotype 2 and genotype 3, and slow type comprising genotype 3 and genotype 3. When the PCR-RFLP method is used, NAT gene polymorphism detection can be achieved in an easy and simple manner within a short period of time, without using any radioactive substance or any of various labeled, type-specific oligonucleotide probes.

By using the PCR-RFLP method according to the invention, it is possible to perform polymorphic NAT gene detection and phenotype judgment using, as a sample, a body fluid of a mammal, such as human, for example blood, marrow fluid, semen, peritoneal cavity fluid or urine, or tissue cells such as liver cells, or body hair such as hair of head.

The use of the NAT genes provided by the invention makes it possible to perform polymorphic NAT gene detection more easily and more rapidly with smaller amounts of DNA as compared with the polymorpohic NAT gene detection by the prior art RFLP method. Furthermore, a kit for polymorpohic NAT gene detection can be provided. By said polymorphic NAT gene detection, it is possible to diagnose or predict the manifestation of an adverse effect or effects by an amino-containing aromatic substance and/or investigate the causes of said adverse effect or effects, among others.

A particularly convenient method to be employed in the practice of the invention uses a kit for NAT gene detection. It is important that said kit includes two reaction solutions for PCR for the site 01 and site 02, respectively, mentioned later in the example section. Said solutions contain a 5'-primer and a 3'-primer for site 01 and site 02. The PCR reaction solutions themselves may be any known ones. As typical examples of the PCR reaction solutions for the above-mentioned kit of the invention, there may be mentioned PCR reaction solutions for site 01 and site 02 which comprise each 100 μl of a reaction system containing 1 μM each of a 5'-primer and a 3'-primer for site 01 and site 02, 0.2 mM dATP, 0.2 mM dCTP, 0.2 mM dGTP, 0.2 mM dTTP, 10 mM Tris, 1.5 mM $MgCl_2$, 50 mM KCl, 1 mg/ml gelatin and 25 U/ml Taq polymerase for use per 0.5 μg of sample DNA.

As a further example, there may be mentioned a kit for polymrophic NAT gene detection which comprises a mixed solution containing the restriction enzymes TaqI, BamHI and KpnI (15 U each), for use per 10 μl of the above amplification reaction mixture. Thus, the whole kit may comprise, for example, the kit I for site 01 PCR, kit II for site 02 PCR and mixed restriction enzyme solution respectively mentioned above.

The following examples and reference examples illustrate the present invention in further detail but are by no means limitative of the scope of the invention.

In the examples, the accompanying drawings are referred to, wherein:

BRIEF DESCRIPTION OF THE DRAWINGS

FIGS. 10A and 10B show the results of PCR-RFLP analysis of the site 01 and site 02 as performed in Example 3.

EXAMPLE 1

(1) Preparation of probes for NAT gene

The BamHI-EcoRI site of the 3'-coding region of the NAT gene type 1 [cf. Ohsako, S and Deguchi, T., J. Biol. Chem., 265 (15), 4630–4634 (1990); Deguchi, T. et al., J. Biol. Chem., 265 (22), 12757–12760 (1990)] was digested with the restriction endonucleases BamHI (Takara Shuzo) and EcoRI (Takara Shuzo) and a DNA fragment of about 308 base pairs was obtained.

The full-length cDNA mentioned above was also used as a probe. While the use of the above BamHI-EcoRI fragment is useful in polymorphic NAT gene detection, the full-length cDNA, when used as a probe, can detect not only polymorphic NAT genes but also monomorphic NAT genes.

For use as a probe, the above BamHI-EcoRI fragment was labeled using α-$[^{32}P]$-dCTP by the multiprime DNA labeling system (Amersham) in which the multiprime DNA labeling method [Feinberg, A. P., et al., Anal. Biochem., 137, 266–267 (1984)] is employed.

The specific activity of the probe was 5–10×$10^8$ cpm/μg.

Figure 1:
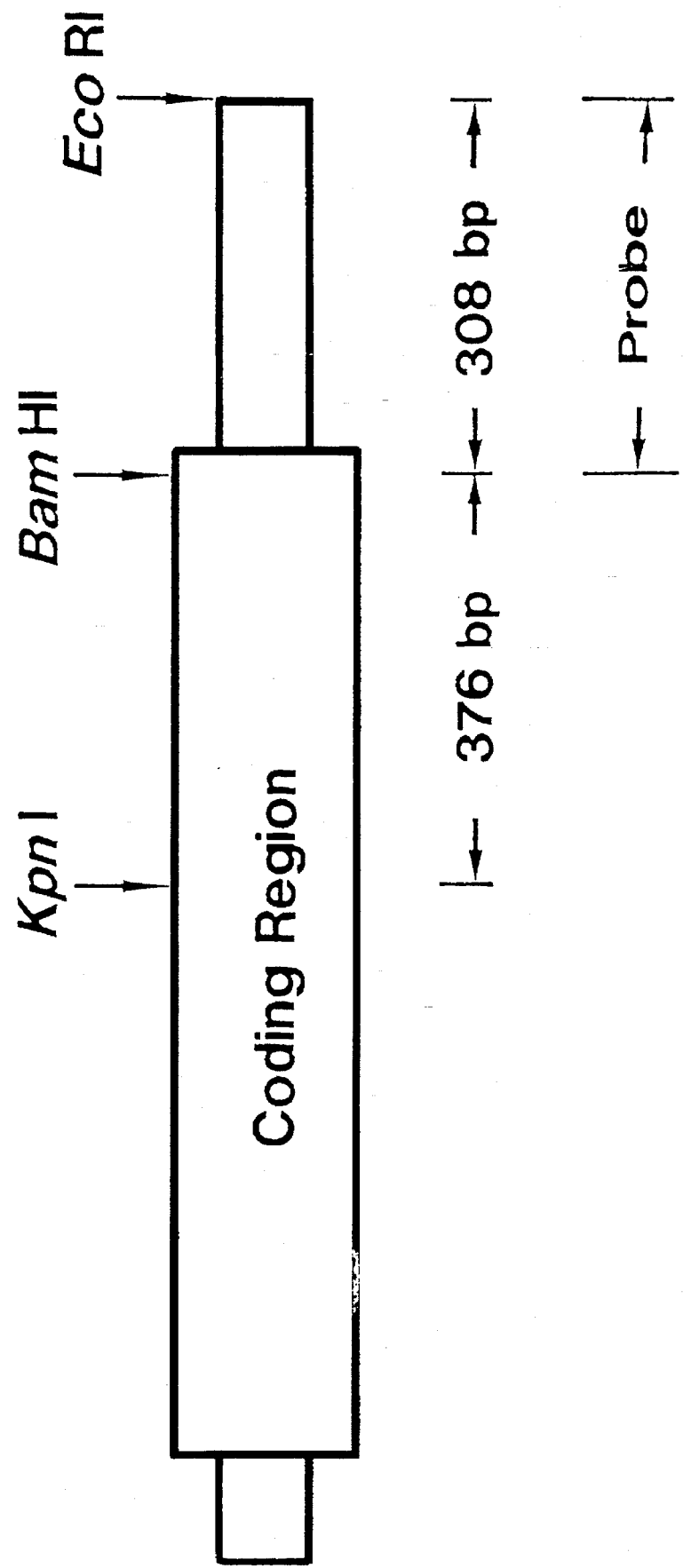
FIG. 1 shows the restriction enzyme map of a NAT gene probe.
Figure 2A:
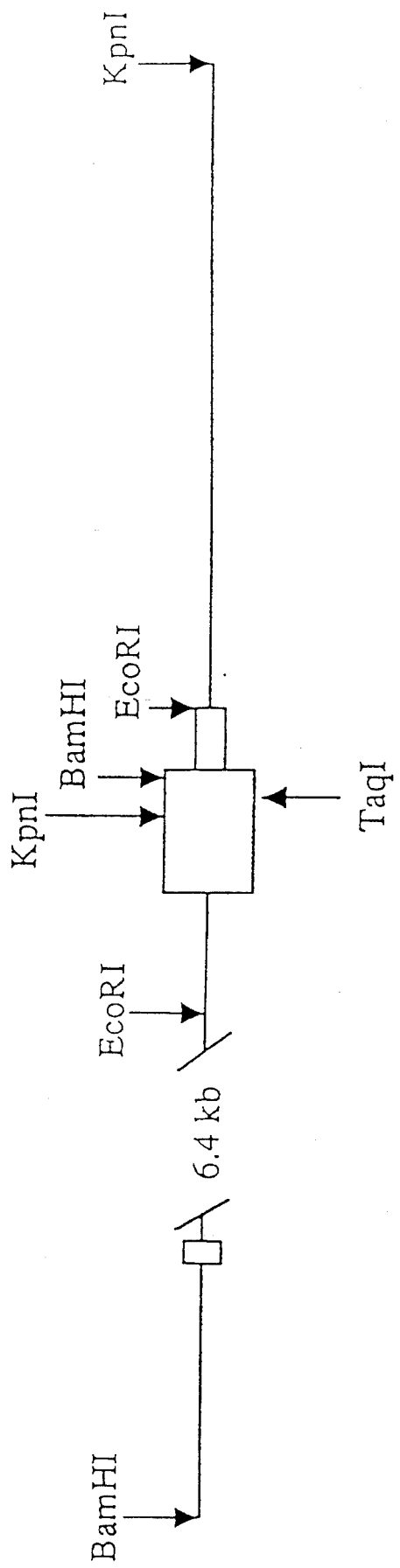
FIGS. 2A–2C show the restriction enzyme maps of various types of NAT gene as revealed by restriction enzyme analysis of genomic DNAs for human NAT.
Figure 2B:
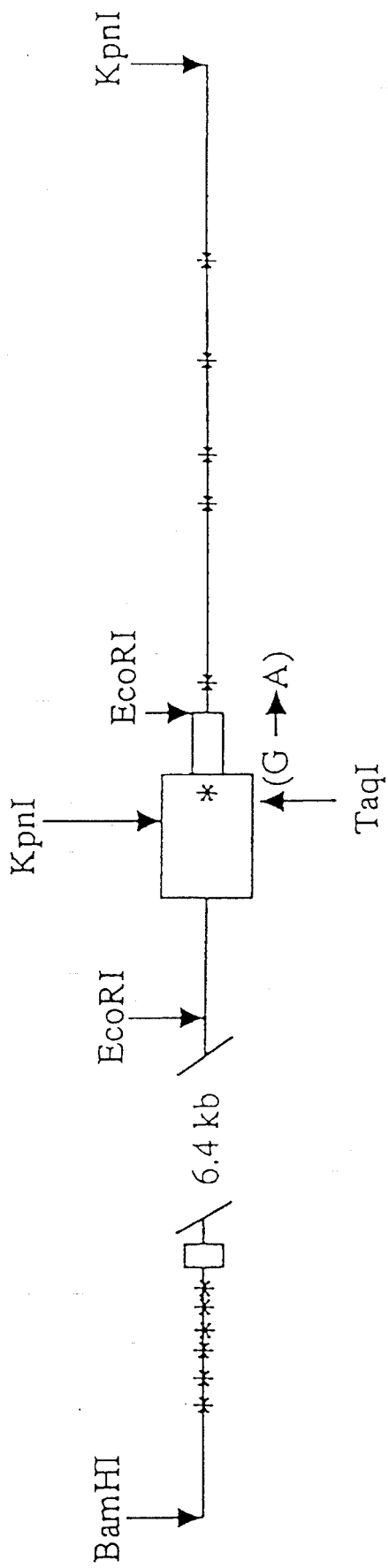
Figure 2C:
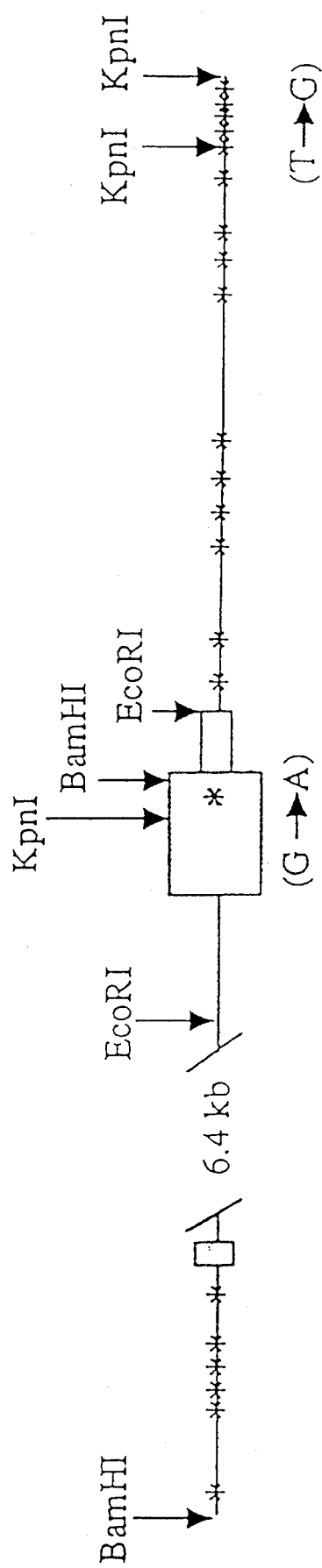

The restriction enzyme map of said probe is shown in FIG. 1.

(2) Isolation of NAT genes

A 1- to 5-g portion of each of human livers obtained at autopsy was converted into a powder by treatment with a whirling blender in the presence of liquefied nitrogen, and then homogenized after addition of 10 to 40 ml of a cytolytic solution [0.32M saccharose, 1% (v/v) Triton X-100, 5 mM $MgCl_2$, 10 mM Tris-hydrochloride (pH 7.5)] ice-cooled beforehand. A nuclear fraction was separated by centrifugation (2,500 rpm, 4° C. 20 minutes), 5 ml of an extractant solution (10 mM Tris-hydrochloride, 0.1M EDTA, 20 μg/ml RNase, 0.5% SDS, pH 8.0) was added thereto, and the mixture was incubated at 37° C. for 1 hour. Proteinase K was added to said mixture to a concentration of 100 μg/ml, and protein digestion was effected at 50° C. for 3 hours. Then, after phenol-chloroform extraction, precipitation was effected with ethanol and the precipitate obtained was dissolved in TE buffer.

About 100 μg of the DNA obtained in the above manner was partially digested with the restriction endonuclease Sau3AI and, after two times of extractions with phenol-chloroform (1:1), ethanol precipitation was carried out. The precipitate was dissolved in 200 μl of TE buffer (10 mM Tris-hydrochloride, 1 mM EDTA, pH 8.0). Sucrose was dissolved in 10 mM Tris-hydrochloride (pH 8.0) containing 10 mM NaCl and 1 mM EDTA to produce a 10–40% sucrose density gradient in a Beckman SW40 Polyallomer centrifuge tube. The partial digest of the DNA extracted as described above was warmed at 68° C. for 10 minutes, then cooled to 20° C. and gently layered on said sucrose density gradient. The centrifuge tube contents were centrifuged at 22,000 rpm and 20° C. for 22 hours using a Beckman SW40 rotor (Backman ultracentrifuge L8M-65). After centrifugation, the bottom of the centrifuge tube was pierced through with a gauge 19 injection needle and the tube contents were fractionally drawn out in about 350-μl portions beginning from the lowermost layer using a peristaltic pump. A 5-μl portion of each fraction thus obtained was subjected to 0.5% agarose gel electrophoresis for DNA size confirmation. Fractions of about 20 kb were pooled and subjected to ethanol precipitation, and the precipitate was dissolved in TE buffer.

EMBL3 was added, as a vector, to the thus-obtained partially digested genomic DNA fragment fraction and the mixture was incubated at 15° C. overnight with T4 DNA ligase. The thus-produced recombinant DNAs were allowed to be taken up by phage particles by in vitro packaging, the phage particles were then allowed to absorbed on *Eschierichia coli* LE392 cells, the cells were sowed, together with a topagar medium, on a plate, and the titer was determined.

In the above manner, a human genomic DNA library containing the desired DNA and comprising at least 1.5 to 3×$10^6$ plaques can be constructed.

(3) Screening by plaque hybridization

Screening was performed by the plaque hybridization technique developed by Benton and Davis [Benton, W. and Davis, R., Science, 196, 383–394 (1977)] using the EMBL3-genomic DNA library obtained as described above in (2) and the probes for screening as prepared above in (1), as follows.

Thus, the library prepared as described above in (2) by incubating the EMBL3-genomic DNA library and *E. coli*

LE392 at 37° C. for 20 minutes to cause phage adsorption on the indicator strain LE392 was sowed on a molten LB soft agar medium [1% Bacto-tryptone, 0.5% yeast extract, 1% sodium chloride, 1.5% Bacto-agar, pH 7.5] containing 50 μg/ml of ampicillin in an inoculum size of about $3 \times 10^5$ cells per culture plate and incubated at 37° C. for 7 to 9 hours for plaque formation. A total of 10 culture plates were used. The plates were then cooled at 4° C. for at least 1 hour. A nitrocellulose filter (20 cm×20 cm; German Science) was placed on the agar plate surface and after 10 minutes of standing at room temperature, the filter was peeled off. The ten filters thus treated were serially numbered and subjected, as master filters, again to the same procedure.

The above filters were each placed on a filter paper (Whatman 3 MM; Whatman) impregnated with 0.5M NaOH and 1.5M NaCl solution, with the plaque-contacting surface at the top and allowed to stand for 10 minutes for alkali treatment of phage DNAs. Each filter was then placed on a filter paper impregnated with 1M Tris-hydrochloride (pH 7.5) and 1.5M NaCl solution and allowed to stand for 10 minutes for neutralization and further placed on a filter paper impregnated with 2×SSC [1×SSC=0.15M NaCl and 0.015M sodium citrate (pH 7.4)] solution and allowed to stand for 5 minutes. The filters were air-dried at room temperature and further dried and baked by heating in a vacuum drier at 80° C. for 2 hours for fixation of phage DNAs on the filters. The baked filters were immersed in 2×SSC, transferred into a prewashing solution [50 mM Tris-hydrochloride (pH 8.0), 0.1M NaCl, 1 mM EDTA, 0.1% SDS] and washed by shaking at 42° C. for 1 hour for removing colonies on the filters.

Further, the filters were shaken in a prehybridization solution [5×SSC, 30% formamide, 50 mM sodium phosphate (pH 7.4), 5×Denhardt's solution {1×Denhardt's =0.02% bovine serum albumin, 0.02% Ficoll, 0.02% polyvinylpyrrolidone}, 0.1% SDS, 100 μg/ml thermally denatured salmon sperm DNA] at 42° C. for 1 hour for prehybridization. The solution was then discarded and, again, 100–200 ml (10–20 ml per filter) of the same prehybridization solution was added. Then, 10–20 ml, per filter, of a solution of the full-length NAT cDNA probe obtained as described above in (1) by labeling with $\alpha$-[$^{32}$P]-dCTP was added to a radioactivity level of 5 to $10 \times 10^5$ cpm/ml, and hybridization was carried out at 42° C. for 24 hours. After completion of the hybridization, the filters were taken out and washed at room temperature for 30 minutes using 2×SSC and 0.1% SDS solution. After two repetitions of washing in that manner, the filters were further washed twice in 0.5×SSC and twice in 0.1% SDS, each time at 56° C. for 30 minutes, and then air-dried at room temperature. The air-dried filters were affixed to a filter paper and, after marking with a [$^{32}$P]-containing ink, placed in a cassette, together with an X-ray film [Kodak XAR5; Kodak] and a sensitizing paper sheet, followed by overnight exposure at −70° C. After development and fixation treatment of the film, signals showing overlapping between two filters were searched for and a plurality of plaques corresponding to the loci of such signals as found were scratched off together with the top agar medium, suspended in SM buffer [50 mM Tris-hydrochloride, pH 7.5, 10 mM MgSO$_4$, 100 mM NaCl, 0.01% gelatin], diluted, this time to an extent such that there was no overlapping between one and another, and sowed on a nirocellulose filter. This filter was subjected to rehybridization for secondary screening, and pure phage clones were isolated.

Twenty-four positive clones were obtained from among $3 \times 10^6$ clones in the above manner. They were subjected to secondary screening and, from among the thus-obtained positive clones, three clones respectively corresponding to the NAT genotypes 1, 2 and 3 were selected. The clones selected were each subjected to agarose gel electrophoresis for isolation and purification. The recombinant phage clones obtained from the EMBL3-genomic DNA library and respectively containing the transcriptional regions of the NAT gene types 1 to 3 were designated as "λhNAT1", "λhNAT2" and "λhNAT3", respectively.

The clones λhNAT1, λhNAT2 and λhNAT3 contain the transcriptional regions of genotype 1, genotype 2 and genotype 3, respectively, as inserts. Said regions contain an exon containing a 5'-noncoding region about 7,000 bp upstream from the coding region, and the 3'-noncoding region and coding region are contained in the second exon.

(4) Production of transformant stains harboring the phNAT plasmids

The DNAs of λhNAT1 to λhNAT3 were each digested with the restriction endonuclease EcoRI (Takara Shuzo) to give a DNA fragment about 1.3 kb in size. Separately, the plasmid vector pUC18 (Takara Shuzo) was digested with the same restriction endonuclease EcoRI. Both the fragments were joined together by means of a ligation kit (Takara Shuzo) using T4 DNA ligase (Takara Shuzo), and the resultant plasmids phNAT1 through phNAT3 were respectively used for the transduction of competent cells of E. coli HB101 (Amersham) therewith.

(5) Base sequence determination of phNAT clones

The gene DNA of each of the clones λhNAT1, λhNAT2 and λhNAT3 was cleaved at specific sites with various restriction endonucleases to give fragments of about 0.3 to 0.7 kb. These fragments were inserted into the cloning vector pUC18 (Takara Shuzo) for subcloning, and the base sequence of each DNA region was determined using a T7 Sequencing kit (Pharmacia) by the dideoxy chain termination method [Sanger, F., et al., Proc. Natl. Acad. Sci., U.S.A., 74, 5463–5467 (1977)] using [$^{32}$P]dCTP.

The gene sequences whose base sequence was determined comprised 9232 bp, 2768 bp of which were included in the 5'-noncoding region of the NAT genes type 1, type 2 and type 3 and 6464 bp of which were included in the coding region and 3'-noncoding region of the NAT genes type 1, type 2 and type 3.

Said base sequences and amino acid sequences deducible therefrom are as shown in SEQ ID NO:1 through SEQ ID NO:6 and SEQ ID NO:7 through SEQ ID NO:9, respectively.

As shown in the sequence listing, the following findings were obtained: The type 1 human NAT gene comprises the DNA sequence of SEQ ID NO:1, a 5'-end 6.4 kb region whose base sequence has not been determined and the DNA sequence of SEQ ID NO:2, with a total of 1321 bases, including the 5'-noncoding region, coding region and 3'-noncoding region. The coding region has a length of 870 bases corresponding to a protein composed of 290 amino acid residues. Based on this deduced sequence, the molecular weight was calculated to be 33541.

The type 2 human NAT gene comprises the DNA sequence of SEQ ID NO:3, a 5'-end 6.4 kb region whose sequence has not been determined and the DNA sequence of SEQ ID NO:4, with a total of 1321 bases including the 5'-noncoding region, coding region and 3'-noncoding region. The coding region has a length of 870 bases corresponding to a protein composed of 290 amino acid residues. Based on this deduced sequence, the molecular weight was calculated to be 33613.

The type 3 human NAT gene comprises the DNA of SEQ ID NO:5, a 5'-end 6.4 kb region whose sequence has not been determined and the DNA sequence of SEQ ID NO:6, with a total of 1321 bases including the 5'-noncoding region, coding region and 3'-noncoding region. The coding region has a length of 870 bases corresponding to a protein composed of 290 amino acid residues. Based on this deduced sequence, the molecular weight was calculated to be 33513.

Among the above sequences, the coding regions of the type 1 and type 2 NAT genes are already known in the art [Ohsako, S. and Deguchi, T., et al., J. Biol. Chem., 265 (8), 4630–4634 (1990)].

As far as the above 9232 bases are concerned, the homology between the type 1 NAT gene and type 2 NAT gene is such that there are point mutations involving 13 base pairs. In the coding region, the 1004th base is C in type 1 NAT gene and, in type 2 NAT gene, it is T. The 1579th base is G in type 1 NAT gene while, in type 2 NAT gene, it is A. As regards the corresponding amino acid changes, the base change at position 1004 is not accompanied by any amino acid substitution but the base change at position 1579 results in substitution of the 286th amino acid (glycine in the case of type 1 NAT gene and glutamic acid in the case of type 2 NAT gene).

For said 9232 bases, the homology between the type 1 NAT gene and type 3 NAT gene is such that there are point mutations involving 23 base pairs. In the coding region, the 1004th base is C in type 1 NAT gene while it is T in type 3 NAT gene. The 1312th base in type 1 NAT gene is G and, in type 3 NAT gene, it is A. As regards the corresponding amino acid changes, the base change at position 1004 is not accompanied by any amino acid substitution but the base change at position 1312 causes substitution of the 197th amino acid (arginine in the case of type 1 NAT gene and glutamine in the case of type 3 NAT gene). Furthermore, the 5918th base downstream from the second exon is G in the type 3 NAT gene in lieu of T in the type 1 NAT gene.

In view of the foregoing, it is seen that, in the type 1 NAT gene, a 6-base sequence including the 1579th base constituted a BamHI restriction site and a 4-base sequence including the 1312th base affords a TaqI restriction site while any 6-base sequence including the 5918th base does not serve as a KpnI restriction site.

On the contrary, in the type 2 NAT gene, a 4-base sequence including the 1312th base serves as a TaqI recognition site but any 6-base sequence including the 1579th base does not constitute a BamHI recognition site. Any 6-base sequence including the 5918th base does not constitute a KpnI recognition site, either.

In the type 3 NAT gene, a 6-base sequence including the 1579th base constitutes a BamHI recognition site and a 6-base sequence including the 5918th base serves as a KpnI recognition site whereas any 4-base sequence including the 1312th base does not serve as a TaqI recognition site.

REFERENCE EXAMPLE 1

Determination of human acetylator phenotypes

Human acetylator phenotypes were determined by the following test. Thus, healthy human volunteers were ordered a rest for 12 hours before and 3 hours after drug administration. Blank blood samples were collected at 9 o'clock in the morning, and then a single dose of 10 mg/kg body weight of isoniazid (INH) in powder form (Daiichi Seiyaku) was administered together with 150 ml of water. At 1, 2 and 3 hours after drug administration, blood samples were collected in heparinized tubes and immediately subjected to centrifugation (3000 rpm, 10 minutes) for plasma separation. Plasma INH levels and plasma acetylisonizid (acetyl-INH) levels were determined by HPLC (high-performance liquid chromatography) according to the method of Hutching et al. [Hutching, A., et al., J. Chromatogr., 277, 385–390 (1983)].

Acetylator phenotypes were distinguished based on the half-life of INH and the acetyl-INH/INH ratio at hour 3 as determined by plasma INH level analysis at 3 hours after drug administration. Individuals showing an acetyl-INH/INH ratio of not more than 0.4 were classified as slow acetylators, individuals in whom said ratio was not lower than 4.4 as rapid acetylators, and individuals in whom said ratio was therebetween as intermediate acetylators.

REFERENCE EXAMPLE 2

Gene typing by restriction fragment length polymorphism analysis

The types of the NAT genes were determined by the method of Deguchi et al. for analyzing band patterns in Souther hybridization as resulting from differences in restriction site distribution [Deguchi, T., et al., J. Biol. Chem., 265 (22), 12757–12760 (1990)], as follows.

Thus, 8 ml of blood was drawn from each of 6 healthy volunteers into an anticoagulant blood-preserving solution (ACD-A solution) and centrifuged (1000×g, 10 minutes) to give leukocytes. The leukocytes were recovered into a polypropylene tube and washed with 5 ml of STE buffer [10 mM Tris-hydrochloride, 100 mM NaCl, 1 mM EDTA, pH 8.0]. The cells were collected by centrifugation (1,000×g, 10 minutes) and 4 ml of a cytolyzing solution [10 mM Tris-hydrochloride, 10 mM EDTA, 0.1% SDS, pH 8.0] was added for suspending the cells therein and, after further addition of 100 µg/ml of proteinase K (Kanto Chemical), protein digestion was caused to proceed overnight at 37° C. Then, 4 ml of phenol saturated with Tris buffer was added and, after gentle stirring, the resulting mixture was centrifuged in the same manner as above, and the aqueous phase was separated. To this aqueous phase was added 4 ml of a mixture of equal volumes of phenol and chloroform, followed by gentle stirring. The resultant mixture was centrifuged in the same manner, and the aqueous phase was separated. Further, 4 ml of chloroform was added to this aqueous phase, the mixture was gently stirred and then centrifuged in the same manner, and the aqueous phase was separated. To this aqueous phase were added 0.4 ml of 3M sodium acetate (pH 5.2) and 8 ml of ethanol, followed by thorough stirring. The mixture was allowed to stand at −80° C. for 1 hour and then centrifuged (2500×g, 30 minutes) and the sediment DNA was recovered. The sediment was washed with 80% ethanol, dried and then dissolved in 0.3 ml of TE buffer. About 300 µg of DNA could be recovered from each blood sample by the above procedure.

To 8 µg of each DNA thus obtained was added 50 units each of restriction endonucleases either alone or in combination, namely KpnI, KDnI+BamHI, EcoRI, or EcoRI+BamHI (each obtained from Takara Shuzo) and enzymatic digestion was allowed to proceed overnight at 37° C. The reaction mixture was electrophoresed on a 0.8% agarose gel at 25 volts for 16 hours. After electrophoresis, bands were transferred to a Hybond N$^+$ nylon filter (Amersham). This filter was placed in a plastic bag, a prehybridization solution [6×SSPE, 5×Denhardt's, 0.5% SDS, 100 µg/ml thermally denatured salmon sperm DNA] was added, and prehybridization was carried out at 65° C. for 2 hours. The compositions of the above-mentioned 6×SSPE and 5×Denhardt's are as follows:

6×SSPE=0.9M NaI, 60 mM sodium phosphate, 6 mM EDTA, pH 7.4;

5×Denhardt's =0.1% Ficoll, 0.1% polyvinylpyrrolidone, 0.1% bovine serum albumin.

Then, a 308 base-pair fragment covering the 3'-noncoding region-containing BamHI-EcoRI region as derived from the type 1 NAT gene cDNA was obtained in the same manner as in Example 1-(1). A probe was prepared therefrom by labeling with [$^{32}$p] using a multiprime DNA labeling system.

Said labeled cDNA probe (specific activity: $1\times10^8$ cpm/μg) was added to the prehybridization mixture to a concentration of $10^6$ cpm/ml and the mixture was incubated overnight at 65° C. After incubation, the nylon membrane was taken out of the bag and washed twice at room temperature for 5 minutes with 2×SSPE [0.3M NaCl, 20 mM sodium phosphate, 2 mM EDTA, pH 7.4] containing 0.5% SDS, further washed at 65° C. for 2 hours with 1×SSPE (pH 7.4) containing 0.5% SDS and again washed at 65° C. for 10 minutes with 2×SSPE containing 0.5% SDS. Then, after further 5-minute washing at room temperature with 2×SSPE, the membrane was air-dried and then subjected to autoradiography (−80° C., 6 days) for exposure of an X-ray film.

Figure 3A:
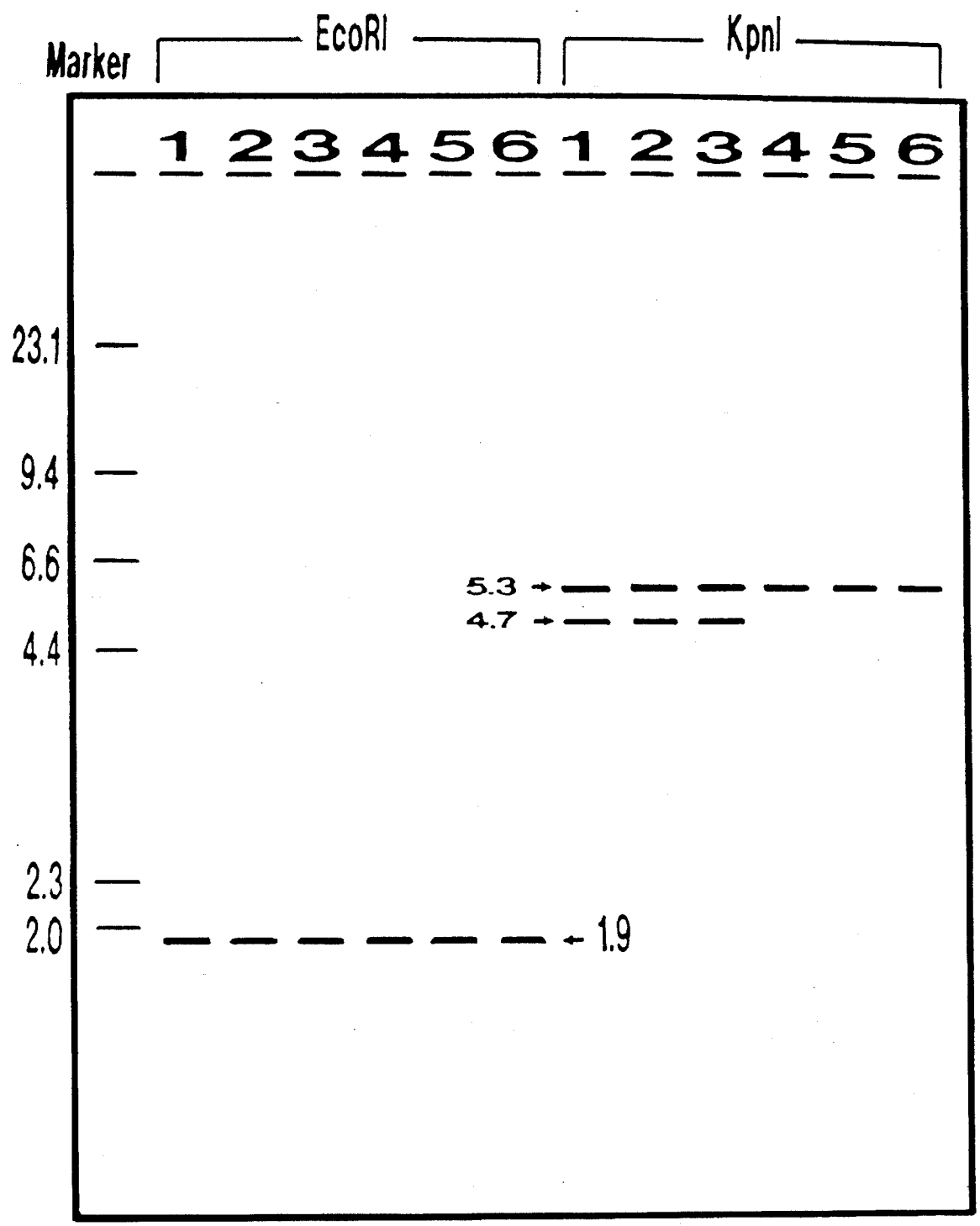
FIGS. 3A and 3B shows the band patterns in Southern hybridization for genotype determination by RFLP.
Figure 3B:
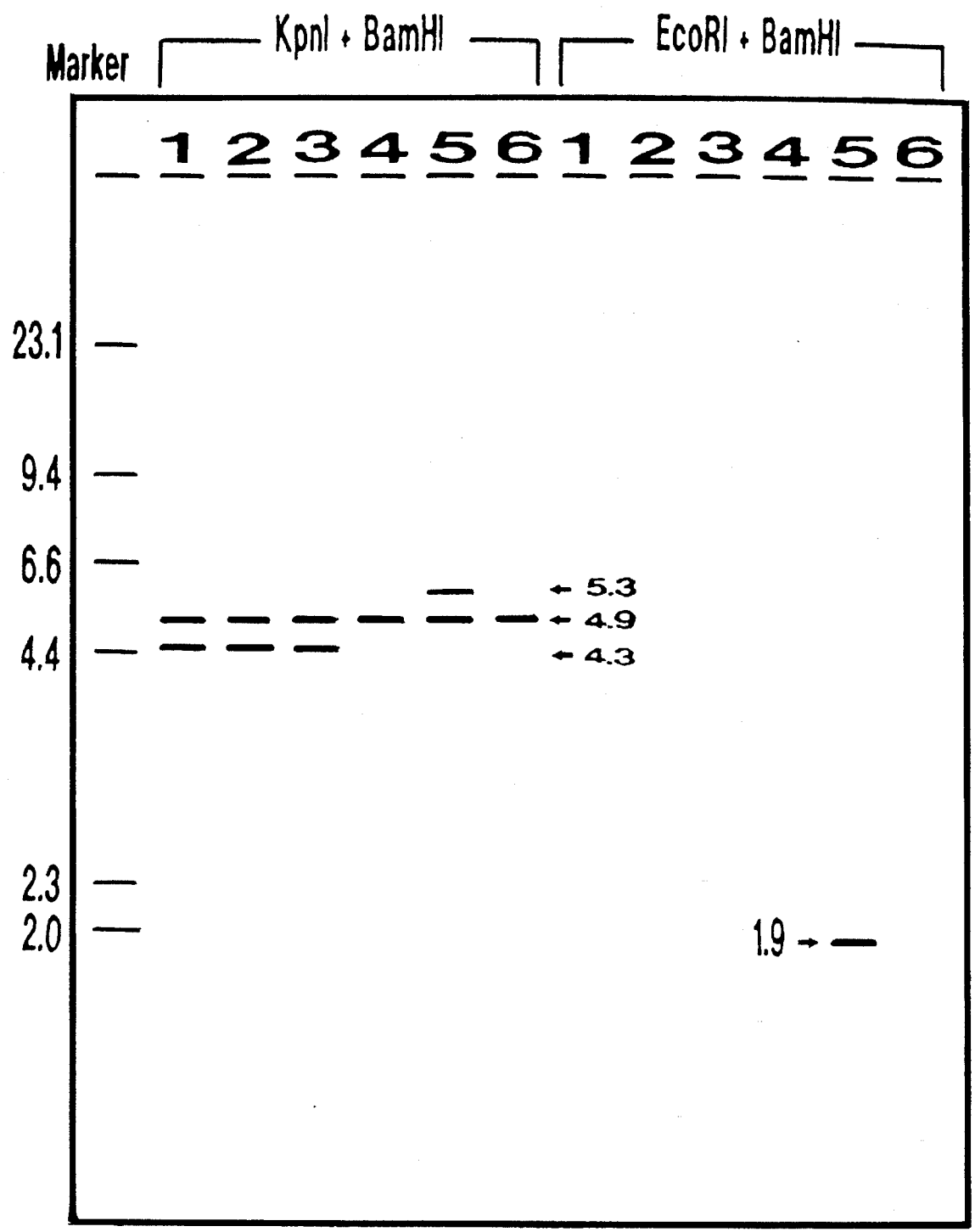

The results obtained in the above manner are shown in FIGS. 3A and 3B.

Referring to human NATs, the NAT gene type 1 contains the base sequence GGATCC, as shown in SEQ ID NO:2. BamHI recognizes the base sequence GGATCC occurring in positions 1578-1583 and cleaves the chromosomal DNA at this site. KpnI does not recognize the base sequence GTTACC occurring in positions 5917-5922 in the subsequent base sequence of said gene as shown under SEQ ID NO:2 and, therefore, the chromosomal DNA will not be cleaved at this site with KpnI. Accordingly, in Southern hybridization following KpnI digestion, the NAT gene type 1 is detected as a band of 5.3 kb and, following KpnI+BamHI digestion, as a band of 4.9 kb.

The NAT gene type 2 contains the base sequence GAATCC, as shown in SEQ ID NO:4. Said seqence is not recognizable, hence will not be cleaved, with BamHI. The sequence GTTACC will not be cleaved with KpnI, either. Therefore, this type 2 is detected as a band of 5.3 kb in Southern hybrodization following KpnI digestion as well in Southern hybridization following KpnI+BamHI digestion.

The NAT type 3 contains the base sequence GGATCC, as shown in SEQ ID NO:6, and this sequence is cleanable with BamHI. Said type contains the sequence GGTACC as well and this sequence is cleanable with KpnI. Therefore, in Southern hybridization following KpnI digestion, said type is detected as a band of 4.7 kb and, in Southern hybridization following KpnI+BamHI digestion, as a band of 4.3 kb.

Based on the band patterns mentioned above, the polymorphism of human NAT gene can include 6 types, as shown below in Table 1.

TABLE 1

| Genotype | Phenotype I Type 1/type 1 | Phenotype II Type 1/type 2 | Phenotype III Type 1/type 3 |
|---|---|---|---|
| KpnI | 5.3 kb | 5.3 kb | 5.3 kb 4.7 kb |
| KpnI + BamHI | 4.9 kb | 5.3 kb 4.9 kb | 4.9 kb 4.3 kb |
| EcoRI | 1.9 kb | 1.9 kb | 1.9 kb |
| EcoRI + BamHI | 1.6 kb | 1.9 kb 1.6 kb | 1.6 kb |

| Genotype | Phenotype IV Type 2/type 2 | Phenotype V Type 2/type 3 | Phenotype VI Type 3/type 3 |
|---|---|---|---|

TABLE 1-continued

| KpnI | 5.3 kb | 5.3 kb 4.7 kb | 4.7 kb |
| KpnI + BamHI | 5.3 kb | 5.3 kb 4.3 kb | 4.3 kb |
| EcoRI | 1.9 kb | 1.9 kb | 1.9 kb |
| EcoRI + BamHI | 1.9 kb | 1.9 kb 1.6 kb | 1.6 kb |

Based on the typing modes shown above in Table 1 and the results shown in FIGS. 3A and 3B, the results for the healthy volunteers used in the present test performed by following the test procedure of Reference Example 1 as mentioned hereinbefore as well as the results of the above-mentioned RFLP analysis were summarized as shown in Table 2.

TABLE 2

| No. | Kpn I | Kpn I + Bam HI | Eco RI | Eco RI + Bam HI | Genotype | Phenotype |
|---|---|---|---|---|---|---|
| 1 | 5.3 4.7 | 4.9 4.3 | 1.9 | — | Type 1 Type 3 | Intermediate |
| 2 | 5.3 4.7 | 4.9 4.3 | 1.9 | — | Type 1 Type 3 | Intermediate |
| 3 | 5.3 4.7 | 4.9 4.3 | 1.9 | — | Type 1 Type 3 | Intermediate |
| 4 | 5.3 | 4.9 | 1.9 | — | Type 1 Type 1 | Rapid |
| 5 | 5.3 | 5.3 4.9 | 1.9 | 1.9 | Type 1 Type 2 | Intermediate |
| 6 | 5.3 | 4.9 | 1.9 | — | Type 1 Type 1 | Rapid |

As shown in Table 2, two were found to be NAT gene type 1/NAT gene type 1 rapid acetylators, one was found to be a NAT gene type 1/NAT gene type 2 intermediate acetylator, and three were found to be NAT gene type 1/NAT gene type 3 intermediate acetylators.

EXAMPLE 2

Gene typing by the PCR-RFLP method
(1) DNA extraction and primer preparation

The following was followed using the DNA samples from 6 healthy volunteers in the same manner as in Reference Example 2. Thus, after phenol extraction as in Reference Example 2, a 0.5-μg portion of each DNA was used as a sample for PCR. Said PCR was carried out using an automatic DNA amplification system (Perkin Elmer Cetus) employing the method of Saiki et al. [Saiki, R., et al., Science, 239, 487–491 (1988)], as follows.

First, a 117-bp segment including TaqI restriction site as found in the coding region of each NAT gene was designated as coding region site 01, and a 393-bp segment including BamHI site in the coding region as coding region site 02. In the same manner as in Example 1-(1), two 5'-primers and two 3'-primers for PCR for site 01 and site 02 were synthesized from four β-cyanoethylphosphoamidite derivatives by the solid-phase method using an automated DNA synthesizer [Gene Assembler Plus (Pharmacia)]. For the synthesis of these oligonucleotide primers, the method of Sinha et al. [Nucl. Acids Res., 5, 397 (1987)] was followed.

The thus-synthesized oligonucleotides were each warmed at 55° C. in concentrated aqueous ammonia for 1 hour, for protective group elimination and oligonucleotide release from the solid carrier. The thus-prepared synthetic oligonucleotides were purified by reversed-phase HPLC and the desired oligonucleotides were obtained as 5'-primers or 3'-primers. The thus-obtained purified oligonucleotides were each dissolved in TE buffer and stored at −20° C.

Figure 4:
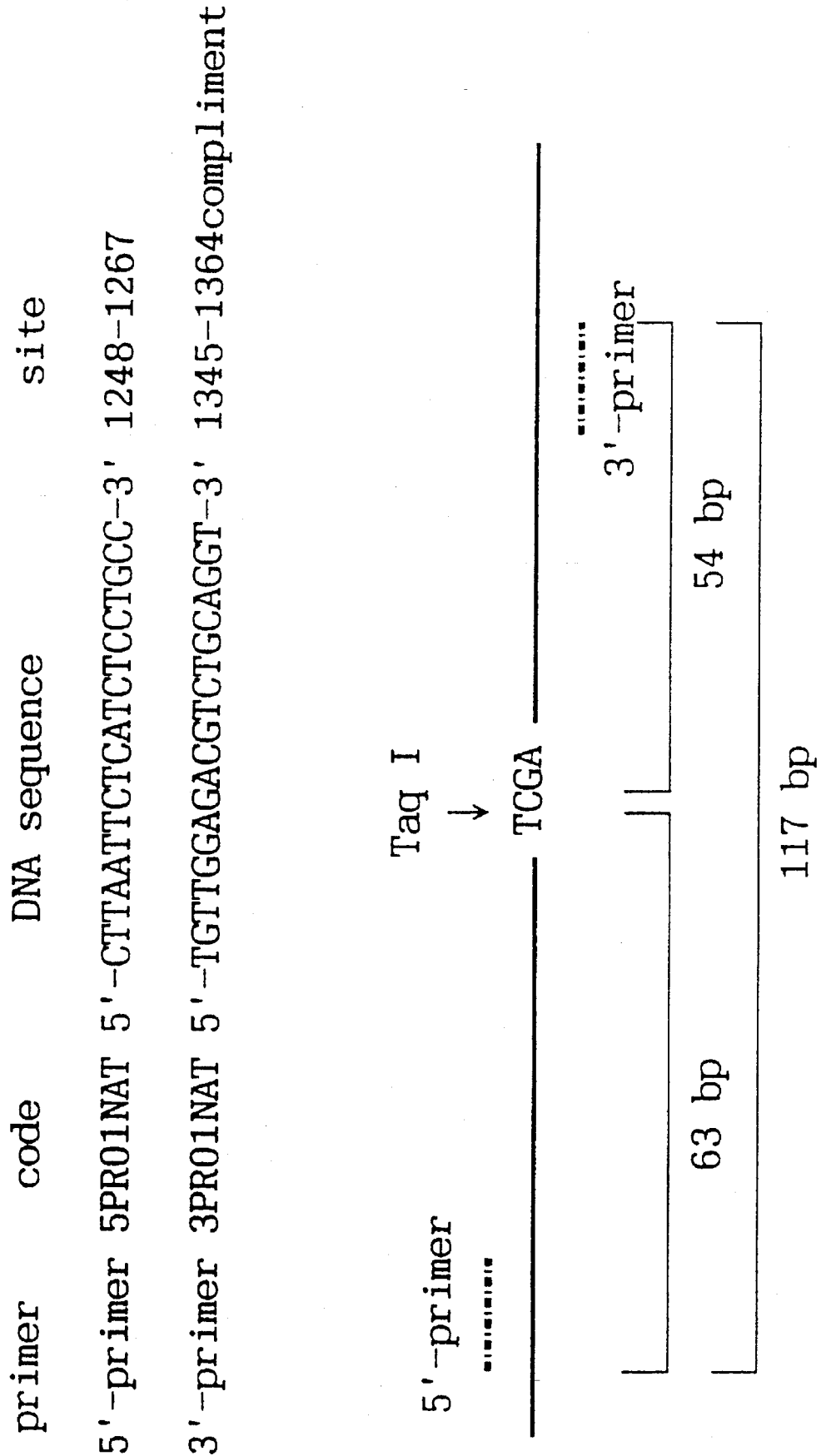
FIG. 4 shows the site 01 amplification region in the coding region of NAT gene and primers for said site 01 (SEQ ID NOS:10 and 11)
Figure 5:
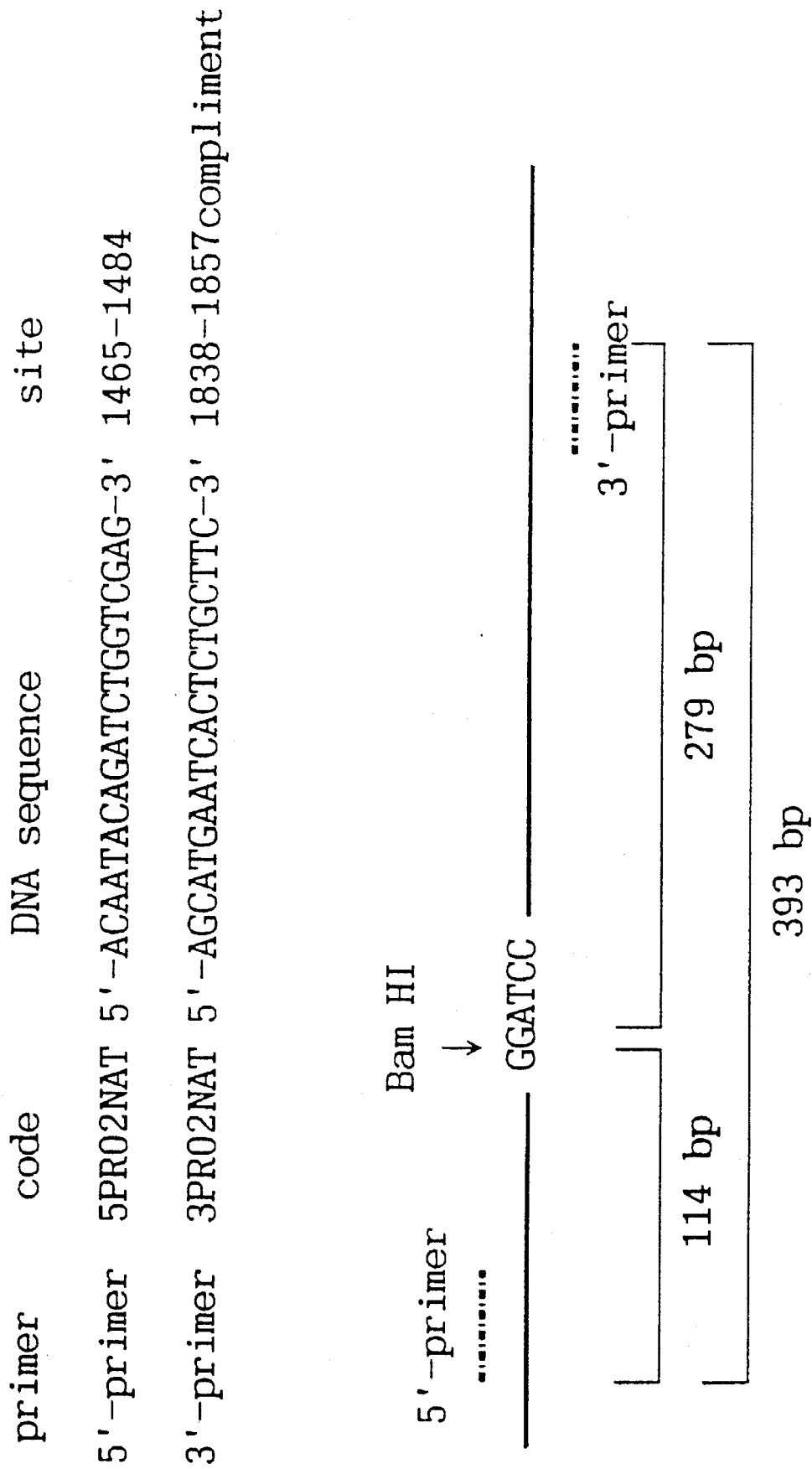
FIG. 5 shows the site 02 amplification region in the coding region of NAT gene and primers for said site 02 (SEQ ID NOS:12 and 13)
Figure 6B:
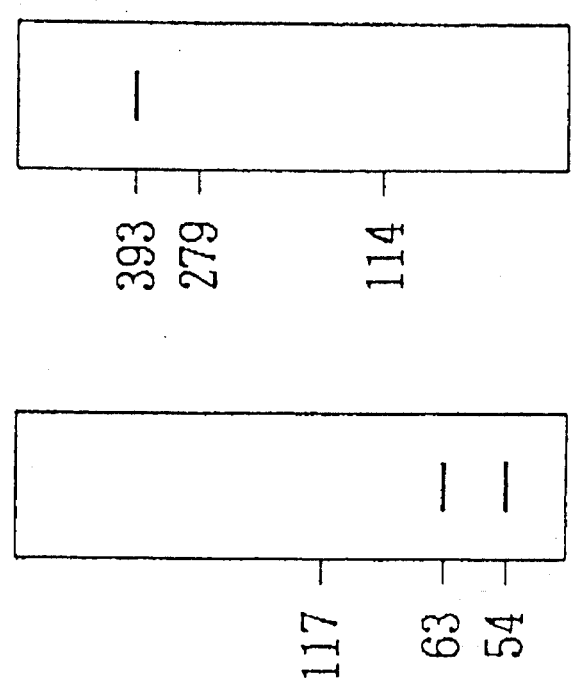
FIGS. 6A–6F show the correlationship between the electrophoretic pattern in PCR-RFLP and the gene polymorphism/acetylator phenotype.
Figure 6A:
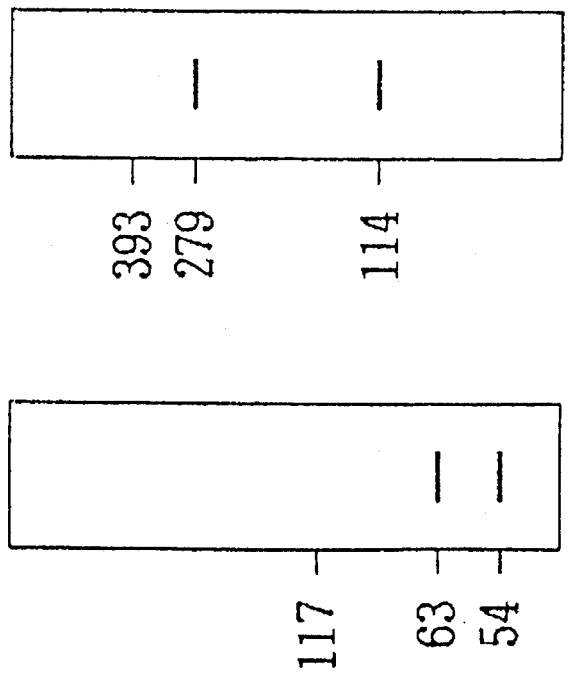
Figure 6D:
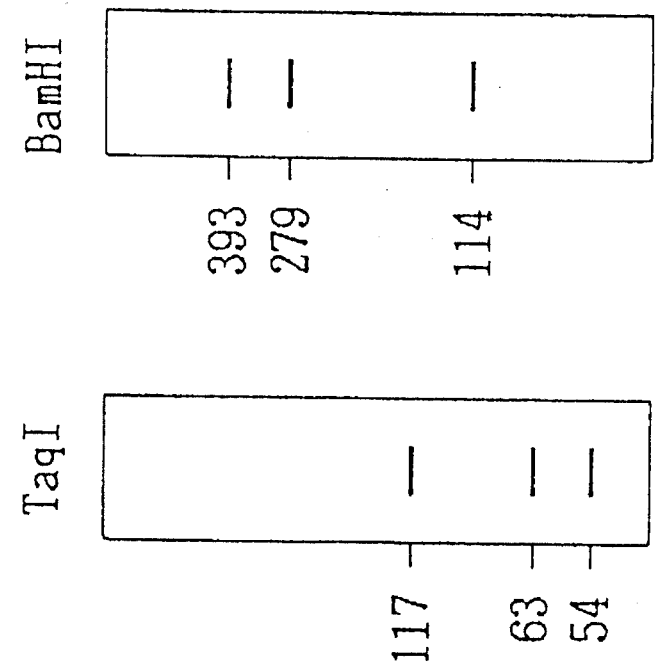
Figure 6C:
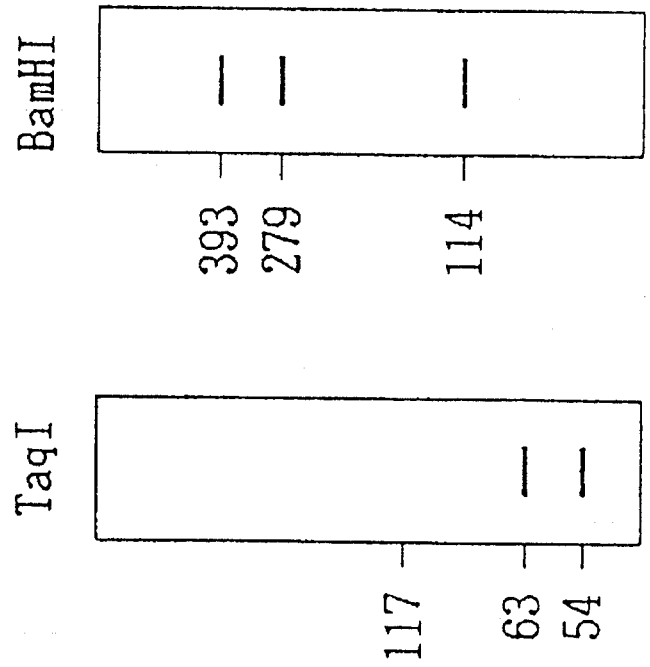
Figure 6E:
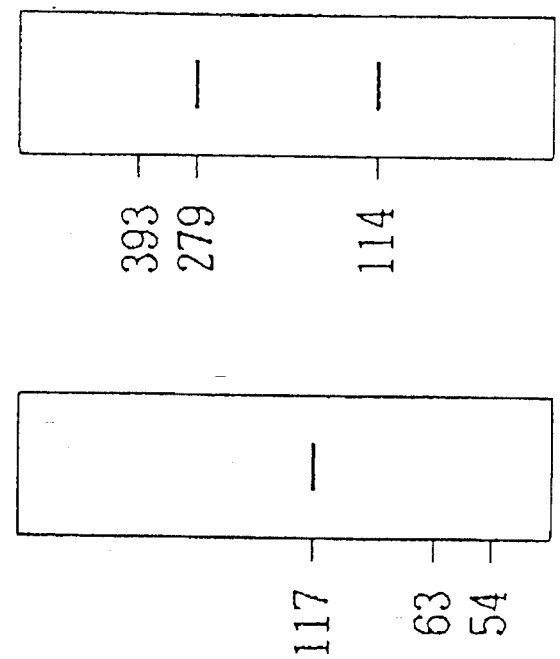
Figure 6F:
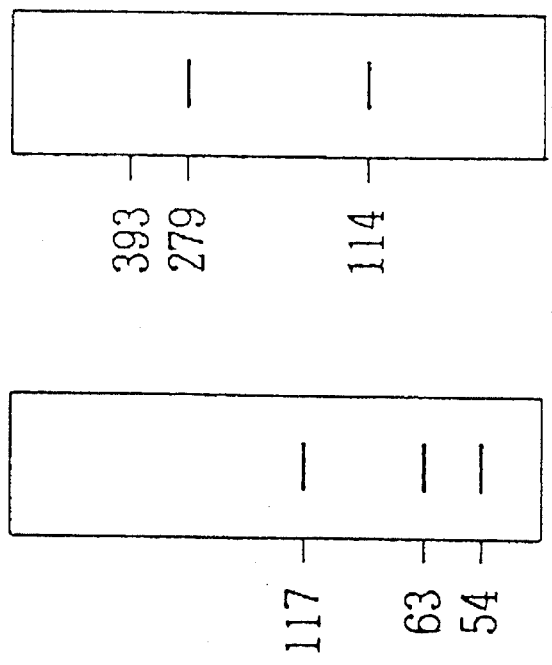

The synthesized primers for site 01 are shown in FIG. 4, and those for site 02 in FIG. 5.

In FIG. 4, the notation "117 bp" indicates the site 01 amplification region in the coding region of the NAT gene, and "TCGA" indicates the site at which said 117-bp region is cleaved into two fragments (63 bp and 54 bp) by the restriction endonuclease TaqI. The 5'-primer is a 20-mer primer comprising the 1248th to 1267th bases [site 01; 5'-primer (1248–1267)], while the 3'-primer is a 20-mer primer comprising the 1345th to 1364th bases [site 02; 3'-primer (1345–1364)].

In FIG. 5, the notation "393 bp" indicates the site 02 amplification region in the coding region of the NAT gene, and "GGATCC" indicates the site at which said 393-bp region is cleaved into two fragments (114 bp and 279 bp) by the restriction endonuclease BamHI. The 5'-primer is a 20-mer primer comprising the 1465th to 1484th bases [site 01; 5'-primer (1465–1484)] and the 3'-primer is a 20-mer primer comprising the 1838th to 1857th bases site 02; 3'-primer (1838–1857)].

Therefore, it is possible to investigate the gene polymorphism in question by amplifying, by the PCR method, those two regions each containing a restriction endonuclease recognition site indicative of the gene polymorphism that lie in the coding region of each of the three NAT genes, subjecting these amplified DNA fragments to restriction endonuclease digestion and forming a judgment based on the combination of the electrophoretic patterns for site 01 and site 02.

The relationship between the electrophoretic patterns in PCR-RFLP and the gene polymorphism is illustrated in FIGS. 6A–6F. In the figure, "Gene 1" stands for type 1, "Gene 2" for type 2 and "Gene 3" for type 3, and "RAPID", "SLOW" and "INTERMEDIATE", each parenthesized and given for a combination of said types stand for rapid acetylator, slow acetylator and intermediate acetylator, respectively.

Thus, in the case of type 1 NAT gene, the electrophoretic patterns for the DNA fragments resulting from amplification by means of the primers for PCR-RFLP and restriction enzyme cleavage show two detectable bands corresponding to 63 bp and 54 bp for site 01 (since the restriction endonuclease TaqI recognizes and cleaves the base sequence TCGA in the site 01 DNA fragment amplified) and two recognizable bands corresponding to 279 bp and 114 bp for site 02 (since BamHI recognizes and cleaves GGATCC).

In the case of type 2 NAT gene, the DNA fragment amplified at site 01 is cleaved with TaqI, whereby two bands corresponding to 63 bp and 54 bp are detected. However, in site 02, the base sequence GAATCC is not cleaved with BamHI, hence the amplified 393-bp DNA fragment is detected as such.

Further, in the case of type 3 NAT gene, the sequence AATC in the amplified site 01 DNA fragment is not cleaved with TaqI, hence said amplified 117-bp DNA fragment is detected as such. For site 02, on the other hand, BamHI recognizes and cleaves GGATCC, giving two detectable bands corresponding to 279 bp and 114 bp.

In view of the above facts, each combination of polymorphic NAT genes can be determined based on the electrophoretic patterns for site 01 and site 02, as illustrated in FIGS. 6A–6F.

(2) Amplification of gene fragments by PCR

A 0.5-μg portion of each DNA obtained in Example 2-(1) was added to 100 μl of the reaction system, followed by further addition of the pair of primers for site 01 or site 02 (1 μM each) together with dATP (0.2 mM), dCTP (0.2 mM), dGTP (0.2 mM), dTTP (0.2 mM), Tris-hydrochloride (10 mM), $MgCl_2$ (1.5 mM), KCl (50 mM), gelatin (1 mg/ml) and 2.5 units of Taq polymerase (all obtained from Perkin Elmer Cetus). After 100 μl of mineral oil was layered on the above mixture, each DNA fragment of site 01 and site 02 was amplified by one cycle of treatment at 94° C. for 3 minutes, at 54° C. for 2 minutes and at 72° C. for 3 minutes, then 29 cycles of treatment at 94° C. for 1 minute, at 54° C. for 2 minutes and at 72° C. for 3 minutes and, lastly, 10 minutes of treatment at 72° C.

The mineral oil was carefully removed from the reaction mixture obtained in the above manner, a 5-μl portion of the remaining reaction mixture was taken and subjected to 3% agarose gel electrophoresis with MspI-digested pUC19 DNA fragments (pUC19/MspI) as markers, followed by ethidium bromide staining for band identification.

Figure 7A:
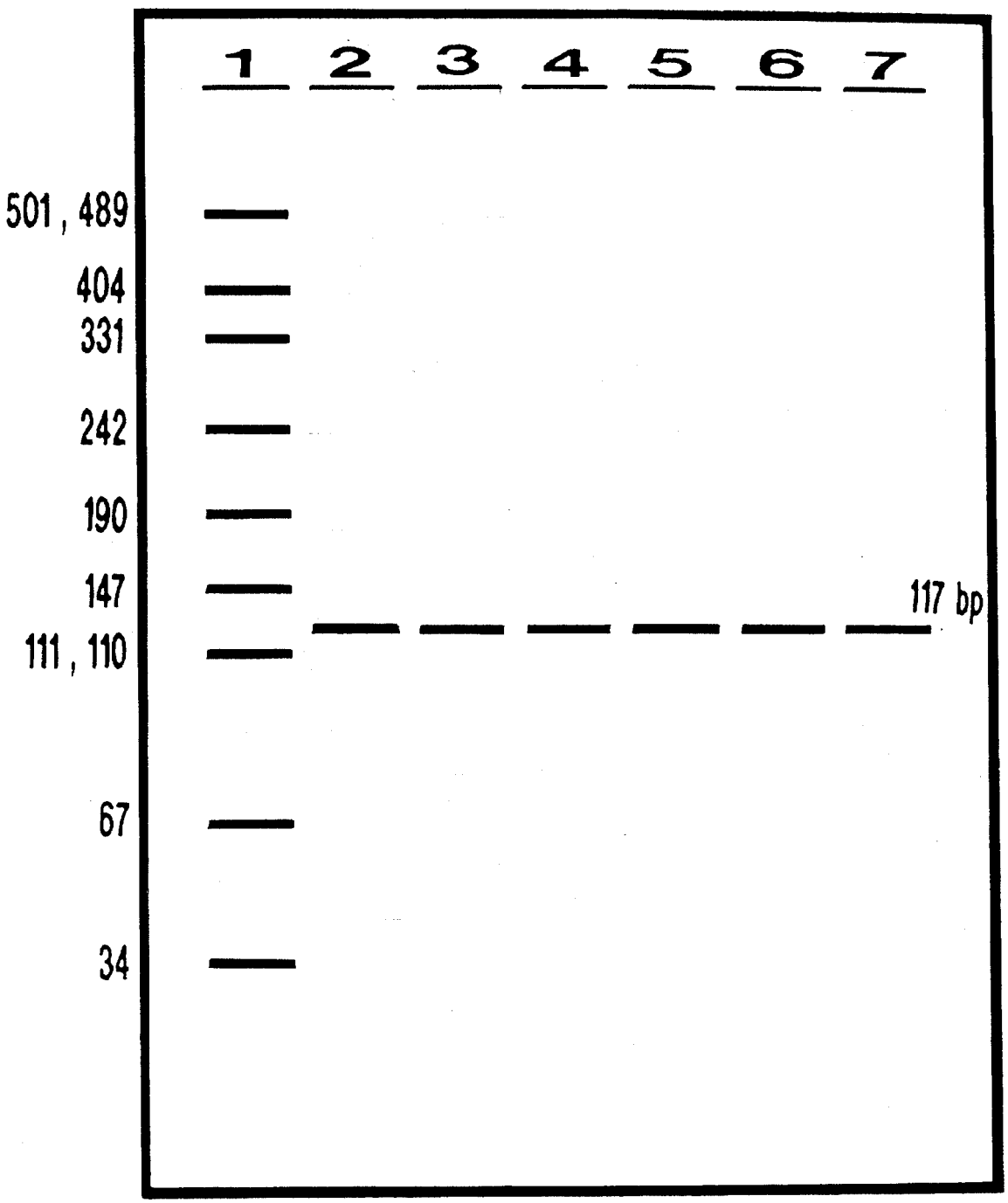
FIGS. 7A and 7B show the results of amplification of the site 01 and site 02 DNA fragments by PCR as performed in Example 2.
Figure 7B:
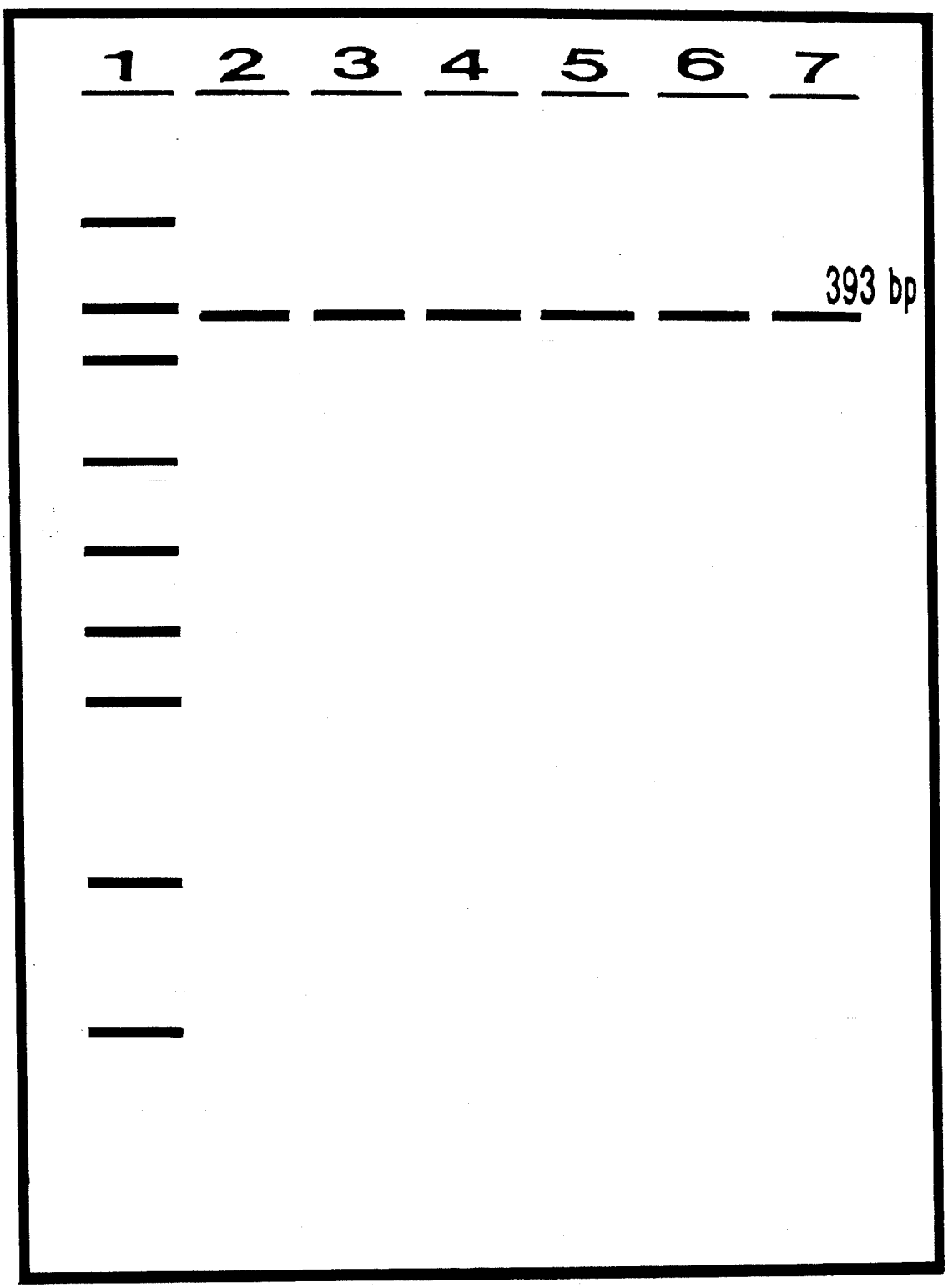

The results of site 01 and site 02 DNA fragments by PCR are shown in FIGS. 7A and 7B; and In the figure, lane 1 is for the pUC19/MspI markers, lane 2 for sample No. 1, lane 3 for sample No. 2, lane 4 for sample No. 3, lane 5 for sample No. 4, lane 6 for sample No. 5 and lane 7 for sample No. 6.

As is clear from the figure, a 117-bp band and a 393-bp band were detected for site 01 and site 02, respectively, with all the samples. Therefore, 10 μl of each amplification reaction mixture was digested with 15 units each of TaqI and BamHI overnight at 37° C. and then subjected to 3% agarose gel electrophoresis, followed by ethidium bromide staining for band detection, as mentioned above.

Figure 8A:
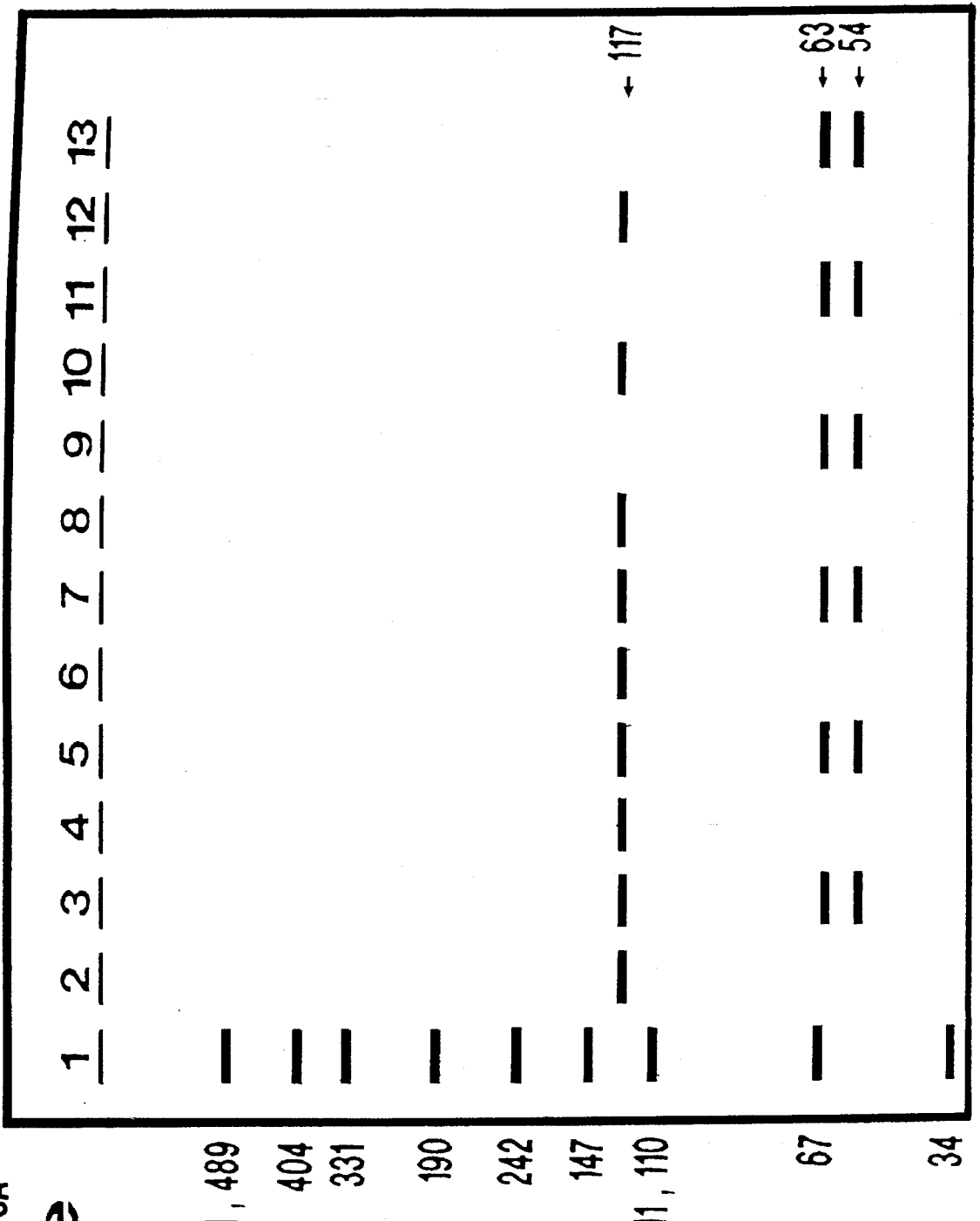
FIGS. 8A and 8B show the results of PCR-RFLP analysis of the site 01 and site 02 as performed in Example 2.
Figure 8B:
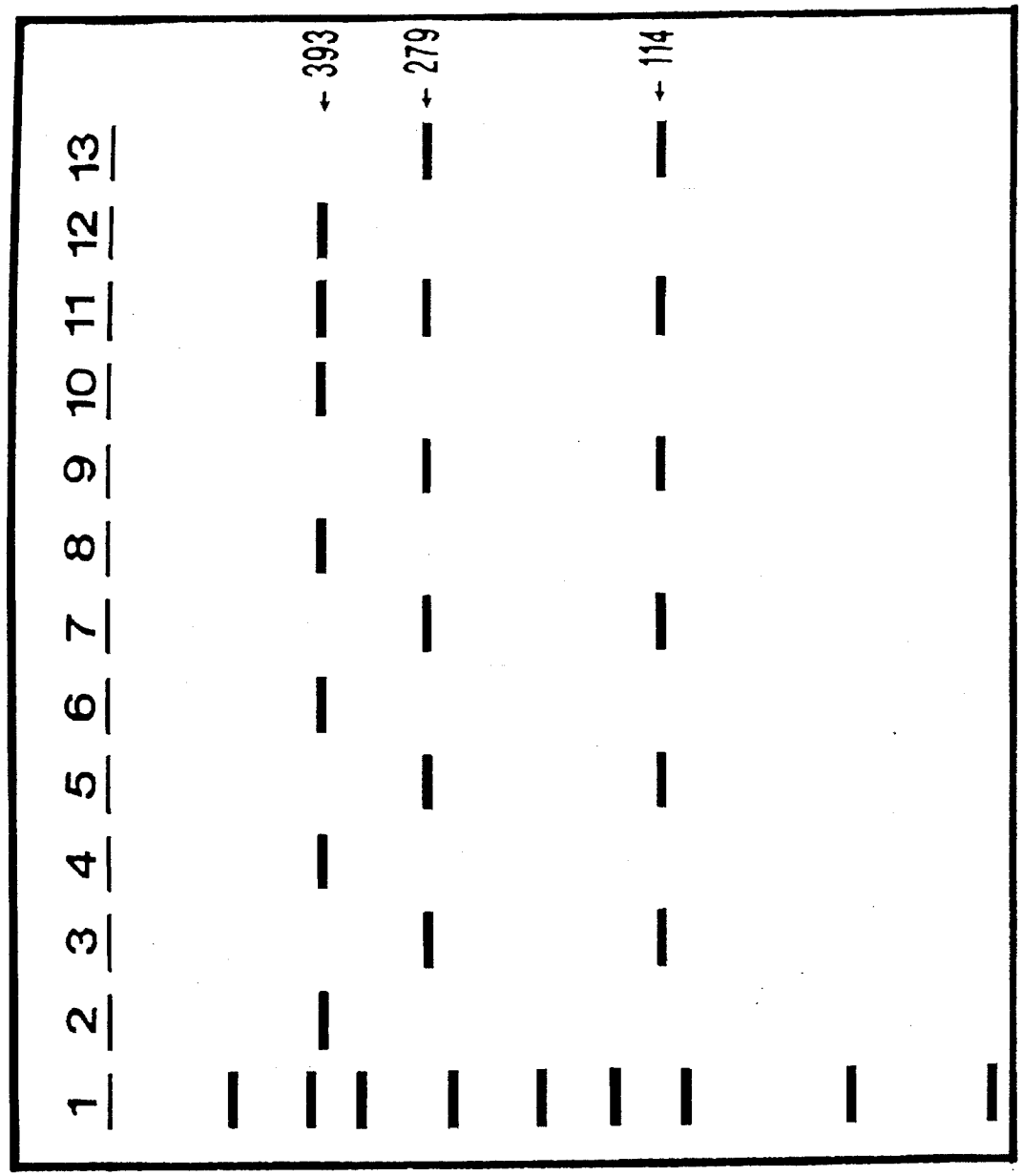

The results of said PCR-RFLP analysis are shown in FIGS. 8A and 8B.

In the figure, lane 1 is for the pUC19/MspI markers, lane 2 for sample No. 1 before digestion, lane 3 for sample No. 1 after digestion, lane 4 for sample No. 2 before digestion, lane 5 for sample No. 2 after digestion, lane 6 for sample No. 3 before digestion, lane 7 for sample No. 3 after digestion, lane 8 for sample No. 4 before digestion, lane 9 for sample No. 4 after digestion, lane 10 for sample No. 5 before digestion, lane 11 for sample No. 5 after digestion, lane 12 for sample No. 6 before digestion and lane 13 for sample No. 6 after digestion.

The data shown in FIG. 8 indicate that, for site 01, samples No. 4 to No. 6 underwent complete digestion, without any traces of the original 117-bp band. Therefore, none of these samples No. 4 to No. 6 contains the type 3 NAT gene. For samples No. 1 to No. 3, three bands, namely the original 117-bp band and two bands (63-bp band and 54-bp band) resulting from digestion, are observed. This presumably means that the chromosome containing one of the alleles contains the type 3 NAT gene which is not recognizable by TaqI.

For site 02, all the samples except sample No. 5 underwent digestion, leaving no trace of the original 393-bp band. Therefore, it is supposed that none of samples No. 1 through No. 4 and sample No. 6 contains the type 2 NAT gene. For sample No. 5, three bands, namely the original 393-bp band and two digestion product bands (279 bp and 114 bp), are observed. This means that the chromosome containing one of the alleles contains the type 2 NAT gene which is not recognizable by BamHI.

Phenotype determination based on the combinations of site 01 and site 02 behaviors as mentioned above identified sample No. 1 as an NAT gene type 1/NAT gene type 3 intermediate acetylator, sample No. 2 as an NAT gene type 1/NAT gene type 3 intermediate acetylator, sample No. 3 as an NAT gene type 1/NAT gene type 3 intermediate actylator, sample No. 4 as an NAT gene type 1/NAT gene type 1 rapid acetylator, sample No. 5 as an NAT gene type 1/NAT gene type 2 intermediate acetylator, and sample No. 6 as an NAT gene type 1/NAT gene type 1 rapid acetylator. These results are in agreement with those of the previous RFLP analysis.

EXAMPLE 3

Analysis of hair samples by PCR-RFLP

The use of the PCR technique makes it possible to analyze samples in trace amounts. Therefore, this possibility was explored using hair samples that can be collected in uninvaded state. DNA extraction from hair samples was performed essentially by the method of Higuchi et al. [Nature, 332, 543 (1988)], as follows.

Thus, 3 to 10 hairs each with the hair root were plucked out from 6 healthy volunteers (4 males and 2 females). The hairs were washed with sterile distilled water and with ethanol, then air-dried and cut to a length of 5–10 mm. Each cut hair sample was recovered in a polypropylene tube, followed by addition thereto 0.5 ml of BCL buffer [10 mM Tris-hydrochloride, 5 mM magnesium chloride, 0.32M saccharose, 1% Triton X-100, pH 7.5], proteinase K (Kanto Chemical) at a final concentration of 100 μg/ml, and SDS at a final concentration of 0.5%, and protein digestion was effected at 70° C. for 1 hour. Then, 0.6 ml of an equivolume mixture of phenol and chloroform and, after gentle stirring, the mixture was centrifuged (10000×g, 15 minutes), and the aqueous phase was separated. To this aqueous phase was further added 0.5 ml of chloroform and, after gentle stirring, the mixture was centrifuged in the same manner, and the aqueous phase was separated. To this aqueous phase were added 50 μl of 3M sodium acetate (pH 5.2) and 1 ml of ethanol. After sufficient stirring, the mixture was allowed to stand at −80° C. for 10 minutes and then centrifuged (10,000×g, 20 minutes) for recovering the DNA precipitate. Said precipitate was washed with 70% ethanol, then dried, and dissolved in 150 μl of sterile distilled water. A 70-μl portion of each DNA solution obtained by the above procedure was submitted to site 01 PCR and to site 02 PCR.

Figure 9:
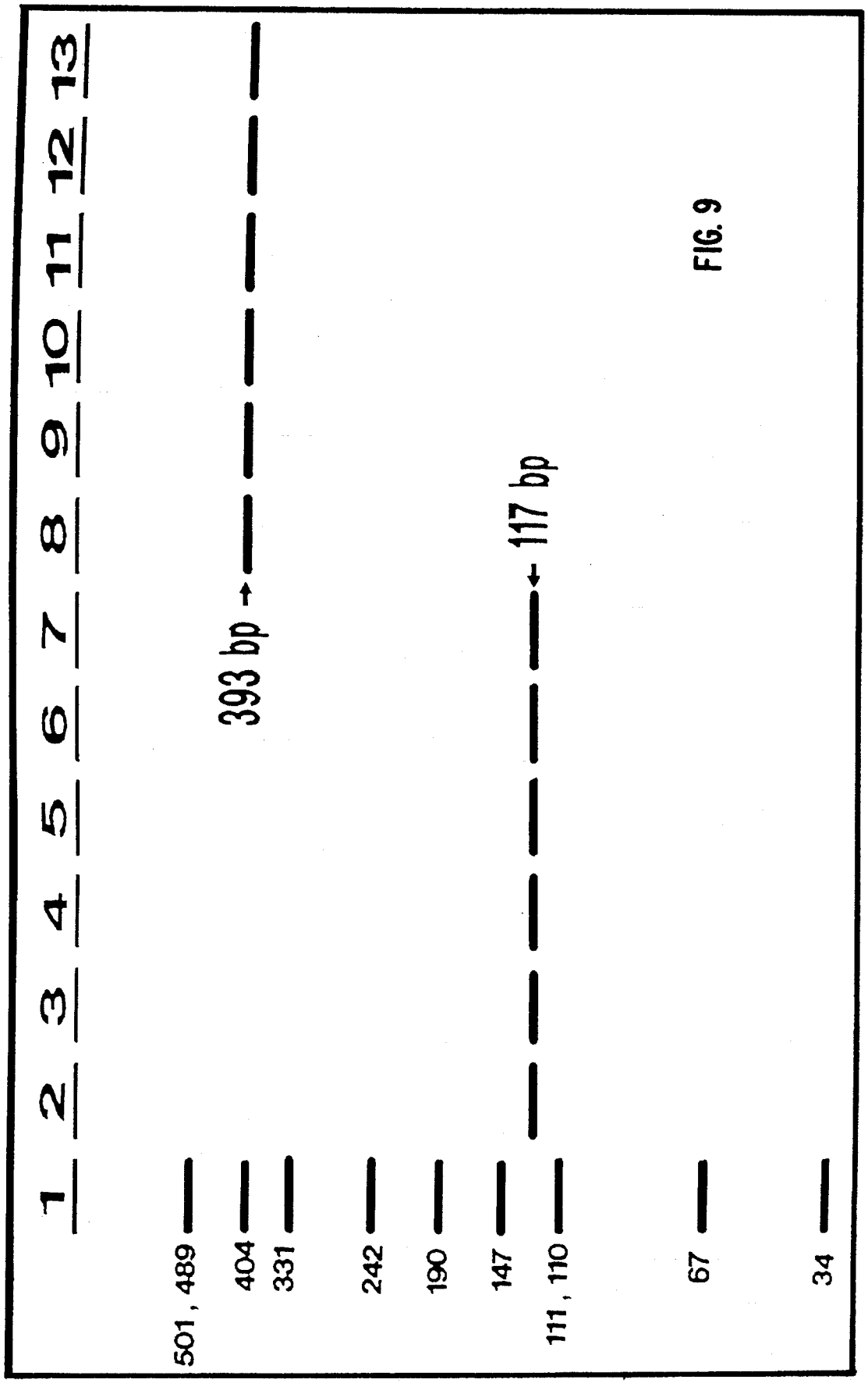
FIG. 9 shows the results of amplification of the site 01 and site 02 DNA fragments by PCR as performed in Example 3.

The hair samples submitted to PCR were as shown in Table 3. The results of PCR are shown in FIG. 9.

TABLE 3

| Sample No. | Sex | Number of hairs collected |
| --- | --- | --- |
| 1 | Female | 3 |
| 2 | Male | 4 |
| 3 | Male | 10 |
| 4 | Male | 6 |
| 5 | Male | 4 |
| 6 | Female | 3 |

In the figure, lane 1 is for the pUC19/MspI markers, lane 2 through lane 7 are for DNA fragment amplification by PCR at site 01 with samples No. 1 through No. 6, respectively, and lane 8 through lane 13 for DNA fragment amplification at site 02 with samples No. 1 through No. 6, respectively.

From FIG. 9, it was noted that the amount of the amplified DNA fragment derived from sample No. 3 which consisted of 10 hairs collected was great while the amount of the sample No. 4-derived DNA fragment was small. These were considered to be reflecting the differences in the amount of DNA collected and extracted, not due to any PCR-related difference. Accordingly, the sample sizes were adjusted so that the amounts of amplified DNA fragments were substantially identical to one another, and digestion with the restriction endonucleases TaqI and BamHI was performed.

Figure 10B:
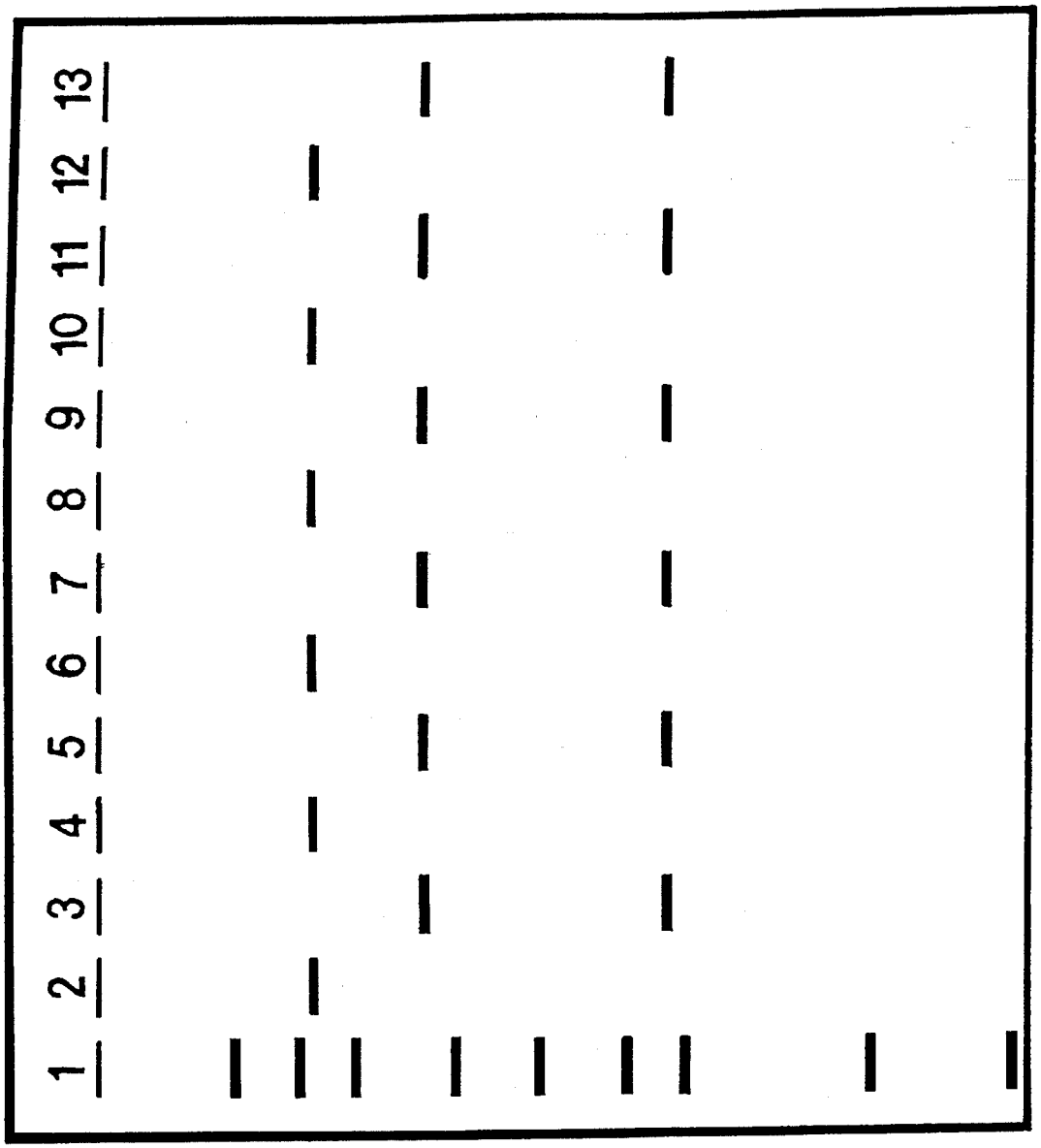

The results thus obtained are shown in FIG. 10A and 10B.

From said figure, it was found that, as regards site 01, sample No. 6 alone gave three bands and, hence, had the type 3 NAT gene. For all other samples, the 117-bp DNA fragment had been digested, hence said samples were supposed to contain no type 3 NAT gene. As regards site 02, all samples gave no 393-bp band, hence were considered to contain no type 2 NAT gene. In view of these, the gene polymorphism-based phenotype were determined as follows: samples No. 1 through No. 5 as NAT gene type 1/NAT gene type 1 rapid acetylators and sample No. 6 as an NAT gene type 1/NAT gene type 3 intermediate acetylator.

Further, hair samples were collected also from those volunteers used for blood sampling in Reference Example 2 (RFLP) and Example 2 (PCR-RFLP) and analyzed in the same manner as mentioned above, to give results agreeing with the previous results.

---

What is claimed is:

1. A kit for determining human arylamine N-acetyltransferase phenotype, comprising component I for site 01 and component II for site 02, wherein component I comprises 100 µl of a reaction solution containing 1 µM each of a 5'-primer of SEQ ID NO:10 and a 3'-primer of SEQ ID NO:11 for site 01, 0.2 mM dATP, 0.2 mM dCTP, 0.2 mM dGTP, 0.2 mM dTTP, 10 mM Tris, 1.5 mM $MgCl_2$, 50 mMKCl, 1 mg/ml gelatin and 25 U/ml Taq polymerase and component II comprises 100 µl of a reaction solution containing 1 µM each of a 5'-primer of SEQ ID NO:12 and a 3'-primer of SEQ ID NO:13 for site 02, 0.2 mM dATP, 0.2 mM dCTP, 0.2 mMd GTP, 0.2 mM dTTP, 10 mM Tris, 1.5 mM $MgCl_2$, 50 mM KCl, 1 mg/ml gelatin and 25 U/ml Taq polymerase, and a solution containing 15 U each of restriction enzymes Taq I and Bam HI.

2. A method for identifying human arylamine N-acetyltransferase genes type 1, 2 or 3 by restriction fragment length polymorphism analysis, comprising the steps of:

(a) amplifying a DNA fragment of extracted sample DNA using a DNA polymerase, a primer which hybridizes to the 5' end of said fragment, wherein said 5' end primer has sequence SEQ ID NO:10 or SEQ ID NO:12, and a primer which hybridizes to the 3' end of said fragment, wherein said 3' end primer has sequence SEQ ID NO:11 or SEQ ID NO:13, said DNA fragment having at least 100–500 base pairs and including a restriction site of Taq I and of Bam HI of human arylamine N-acetyltransferase coding region, said DNA fragment including a polymorphic restriction enzyme site which is diagnostic of types 1, 2 and 3 human arylamine N-acetyltransferase;

(b) cleaving the amplified DNA fragment of step (a) with Bam HI and Taq I restriction endonuclease;

(c) obtaining a band pattern based on size for the cleaved DNA fragments obtained in step (b); and (d) analyzing said band pattern so as to detect presence of human arylamine N-acetyltransferase genes type 1, 2 or 3.

3. A method for identifying human arylamine N-acetyltransferase phenotype, comprising analyzing the band pattern obtained in the method for identifying human arylamine N-acetyltransferase genes type 1, 2 or 3 of claim 2 and correlating the pattern to rapid, intermediate or slow acetylator activity.

4. The method of detecting human arylamine N-acetyltransferase genes type 1, 2 or 3 of claim 2, wherein said DNA fragment is obtained from a sample selected from the group consisting of human blood, human marrow, human semen, human peritoneal cavity fluid, urine, a human tissue cell and human hair.

5. The method of detecting human arylamine N-acetyltransferase phenotype of claim 3, wherein said DNA fragment is obtained from a sample selected from the group consisting of human blood, human marrow, human semen, human peritoneal cavity fluid, urine, a human tissue cell and human hair.

\* \* \* \* \*